(12) United States Patent
Gerber et al.

(10) Patent No.: US 7,666,189 B2
(45) Date of Patent: Feb. 23, 2010

(54) LESS INVASIVE SURGICAL SYSTEM AND METHODS

(75) Inventors: David Gerber, West Chester, PA (US);
Shaun Hanson, West Chester, PA (US);
Xiaoping Hu, Oreland, PA (US);
Douglas Scott Kephart, Glen Mills, PA (US); Kyle Kuntz, West Chester, PA (US); Andrew Max Lee, Oreland, PA (US)

(73) Assignee: Synthes USA, LLC, West Chester, PA (US)

( * ) Notice: Subject to any disclaimer, the term of this patent is extended or adjusted under 35 U.S.C. 154(b) by 875 days.

(21) Appl. No.: 10/957,888

(22) Filed: Sep. 29, 2004

(65) Prior Publication Data

US 2006/0074445 A1 Apr. 6, 2006

(51) Int. Cl.
*A61B 17/58* (2006.01)

(52) U.S. Cl. .................. 606/104; 606/99; 606/86 A; 81/453

(58) Field of Classification Search ............... 606/86 A, 606/99, 914, 104, 279; 81/452–458
See application file for complete search history.

(56) References Cited

U.S. PATENT DOCUMENTS

| 915,770 | A | * | 3/1909 | Jacobs | ............... | 81/453 |
|---|---|---|---|---|---|---|
| 4,449,532 | A | | 5/1984 | Storz | | |
| 4,862,891 | A | | 9/1989 | Smith | | |
| 4,903,692 | A | * | 2/1990 | Reese | ............... | 606/99 |
| 5,071,410 | A | | 12/1991 | Pazell | | |
| 5,092,866 | A | | 3/1992 | Breard et al. | | |
| 5,357,983 | A | | 10/1994 | Mathews | | |
| 5,480,440 | A | | 1/1996 | Kambin | | |
| 5,618,260 | A | | 4/1997 | Caspar et al. | | |

(Continued)

FOREIGN PATENT DOCUMENTS

AU  A-13672/95  9/1995

(Continued)

OTHER PUBLICATIONS

Kevin T. Foley, M.D., "CD Horizon® Sextant™: Rod Insertion System Surgical Technique," Medtronic Sofamor Danek (2002).

(Continued)

*Primary Examiner*—Thomas C Barrett
*Assistant Examiner*—James L. Swiger
(74) *Attorney, Agent, or Firm*—Stroock & Stroock & Lavan LLP

(57) ABSTRACT

A system for performing a less invasive surgical procedure and, in particular, devices and methods for spinal fixation. The system comprises dilation tool(s), at least one working/insertion cannula, a plurality of screws, at least one fixation rod for connecting the screws, and a rod inserter. The dilation tool(s) may be used to dilate an incision made in a patient to form an opening. An insertion cannula may be attached to a screw and inserted into the opening. The screws may be polyaxial screws and may be inserted into the vertebrae using a screwdriver. An operator may then move the insertion cannula to manipulate a head portion of the screws such that the head portions may be aligned to receive a fixation rod. A rod inserter may be used to insert a fixation rod into the head portions.

40 Claims, 43 Drawing Sheets

U.S. PATENT DOCUMENTS

| | | | |
|---|---|---|---|
| 5,643,274 A | 7/1997 | Sander et al. | |
| 5,667,513 A | 9/1997 | Torrie et al. | |
| 5,681,265 A | 10/1997 | Maeda et al. | |
| 5,720,751 A | 2/1998 | Jackson | |
| 5,728,046 A | 3/1998 | Mayer et al. | |
| 5,741,261 A * | 4/1998 | Moskovitz et al. | 606/79 |
| 5,785,648 A | 7/1998 | Min | |
| 5,885,210 A | 3/1999 | Cox | |
| 5,885,300 A * | 3/1999 | Tokuhashi et al. | 606/99 |
| 5,931,777 A | 8/1999 | Sava | |
| 5,964,761 A | 10/1999 | Kambin | |
| 6,099,547 A * | 8/2000 | Gellman et al. | 606/198 |
| 6,123,707 A | 9/2000 | Wagner | |
| 6,139,549 A | 10/2000 | Keller | |
| 6,175,758 B1 | 1/2001 | Kambin | |
| 6,183,472 B1 * | 2/2001 | Lutz | 606/86 A |
| 6,196,969 B1 | 3/2001 | Bester et al. | |
| 6,200,322 B1 * | 3/2001 | Branch et al. | 606/96 |
| 6,206,826 B1 * | 3/2001 | Mathews et al. | 600/210 |
| 6,235,028 B1 | 5/2001 | Brumfield et al. | |
| 6,302,842 B1 | 10/2001 | Auerbach et al. | |
| 6,309,349 B1 | 10/2001 | Bertolero et al. | |
| 6,360,750 B1 | 3/2002 | Gerber et al. | |
| 6,415,693 B1 * | 7/2002 | Simon et al. | 81/453 |
| 6,440,133 B1 | 8/2002 | Beale et al. | |
| 6,520,907 B1 | 2/2003 | Foley et al. | |
| 6,530,929 B1 | 3/2003 | Justis et al. | |
| 6,575,899 B1 | 6/2003 | Foley et al. | |
| 6,648,888 B1 * | 11/2003 | Shluzas | 606/86 A |
| 6,660,006 B2 * | 12/2003 | Markworth et al. | 606/86 A |
| 6,663,562 B2 | 12/2003 | Chang | |
| 6,743,231 B1 | 6/2004 | Gray et al. | |
| 6,746,454 B2 * | 6/2004 | Winterbottom et al. | 606/99 |
| 6,790,209 B2 | 9/2004 | Beale et al. | |
| 6,793,656 B1 | 9/2004 | Mathews | |
| 6,800,084 B2 | 10/2004 | Davison et al. | |
| 6,811,558 B2 | 11/2004 | Davison et al. | |
| 6,849,064 B2 | 2/2005 | Hamada | |
| 2002/0020255 A1 | 2/2002 | Simon et al. | |
| 2002/0161368 A1 * | 10/2002 | Foley et al. | 606/61 |
| 2003/0060826 A1 | 3/2003 | Foley et al. | |
| 2003/0191370 A1 | 10/2003 | Phillips | |
| 2003/0191371 A1 | 10/2003 | Smith et al. | |
| 2003/0199871 A1 | 10/2003 | Foley et al. | |
| 2003/0208203 A1 | 11/2003 | Lim et al. | |
| 2003/0216768 A1 | 11/2003 | Gitis et al. | |
| 2003/0229347 A1 | 12/2003 | Sherman et al. | |
| 2003/0236447 A1 | 12/2003 | Ritland | |
| 2004/0002629 A1 | 1/2004 | Branch et al. | |
| 2004/0024291 A1 | 2/2004 | Zinkel | |
| 2004/0034351 A1 | 2/2004 | Sherman et al. | |
| 2004/0039384 A1 | 2/2004 | Boehm et al. | |
| 2004/0059339 A1 | 3/2004 | Roehm et al. | |
| 2004/0138662 A1 | 7/2004 | Landry et al. | |
| 2004/0143265 A1 | 7/2004 | Landry et al. | |
| 2004/0147928 A1 | 7/2004 | Landry et al. | |
| 2004/0147937 A1 | 7/2004 | Dunbar, Jr. et al. | |
| 2004/0172022 A1 | 9/2004 | Landry et al. | |
| 2004/0176763 A1 | 9/2004 | Foley et al. | |
| 2004/0215190 A1 | 10/2004 | Nguyen et al. | |
| 2004/0267275 A1 | 12/2004 | Cournoyer et al. | |
| 2005/0004593 A1 | 1/2005 | Simonson | |
| 2005/0010220 A1 | 1/2005 | Casutt et al. | |
| 2005/0021031 A1 | 1/2005 | Foley et al. | |
| 2005/0038432 A1 | 2/2005 | Shaolian et al. | |
| 2005/0043742 A1 | 2/2005 | Bruneau et al. | |
| 2005/0065517 A1 | 3/2005 | Chin | |
| 2005/0070765 A1 | 3/2005 | Abdelgany et al. | |
| 2005/0080418 A1 | 4/2005 | Simonson et al. | |
| 2005/0080443 A1 | 4/2005 | Fallin et al. | |
| 2005/0085813 A1 * | 4/2005 | Spitler et al. | 606/61 |
| 2005/0090824 A1 | 4/2005 | Shluzas et al. | |
| 2005/0090899 A1 * | 4/2005 | DiPoto | 623/17.11 |
| 2005/0113644 A1 | 5/2005 | Obenchain et al. | |
| 2005/0131408 A1 | 6/2005 | Sicvol et al. | |
| 2005/0131419 A1 | 6/2005 | McCord et al. | |
| 2005/0131420 A1 | 6/2005 | Techiera et al. | |
| 2005/0131421 A1 | 6/2005 | Anderson et al. | |
| 2005/0131422 A1 | 6/2005 | Anderson et al. | |
| 2005/0149035 A1 | 7/2005 | Pimenta et al. | |
| 2005/0154389 A1 | 7/2005 | Selover et al. | |
| 2005/0159651 A1 | 7/2005 | Raymond et al. | |
| 2005/0165281 A1 | 7/2005 | Ravikumar et al. | |
| 2005/0192570 A1 | 9/2005 | Jackson | |
| 2005/0192589 A1 | 9/2005 | Raymond et al. | |
| 2005/0215999 A1 | 9/2005 | Birkmeyer et al. | |
| 2005/0228380 A1 | 10/2005 | Moore et al. | |
| 2005/0234449 A1 | 10/2005 | Aferzon | |
| 2006/0036244 A1 | 2/2006 | Spitler et al. | |
| 2006/0036255 A1 | 2/2006 | Pond, Jr. et al. | |
| 2006/0036260 A1 | 2/2006 | Runco et al. | |
| 2006/0074418 A1 * | 4/2006 | Jackson | 606/61 |
| 2006/0079894 A1 | 4/2006 | Colleran et al. | |

FOREIGN PATENT DOCUMENTS

| | | |
|---|---|---|
| EP | 0455282 A2 | 11/1991 |
| EP | 0951868 A1 | 10/1999 |
| JP | 11076247 | 3/2003 |
| WO | WO9421179 A2 | 9/1994 |
| WO | WO 98/44858 | 10/1998 |
| WO | WO9844858 A1 | 10/1998 |
| WO | WO03017847 A1 | 3/2003 |
| WO | WO 2005/058386 | 6/2005 |

OTHER PUBLICATIONS

Charles L. Branch, Jr., M.D., Kevin T. Foley, M.D., "Tangent™: Posterior Impacted Instrument Set Technique," Medtronic Sofamor Danek (2002).

Donald I. Hilton, Jr., M.D., Sylvain Palmer, M.D., "METR$_x$: Microdisectomy Surgical Technique" Medtronic Sofamor Danek (2001).

Atavi™: Atraumatic Spine Fusion System—Endoscopic Posterolateral Fusion, Endius (2001).

Aperture™ Spinal Access System, DePuy AcroMed (2003).

\* cited by examiner

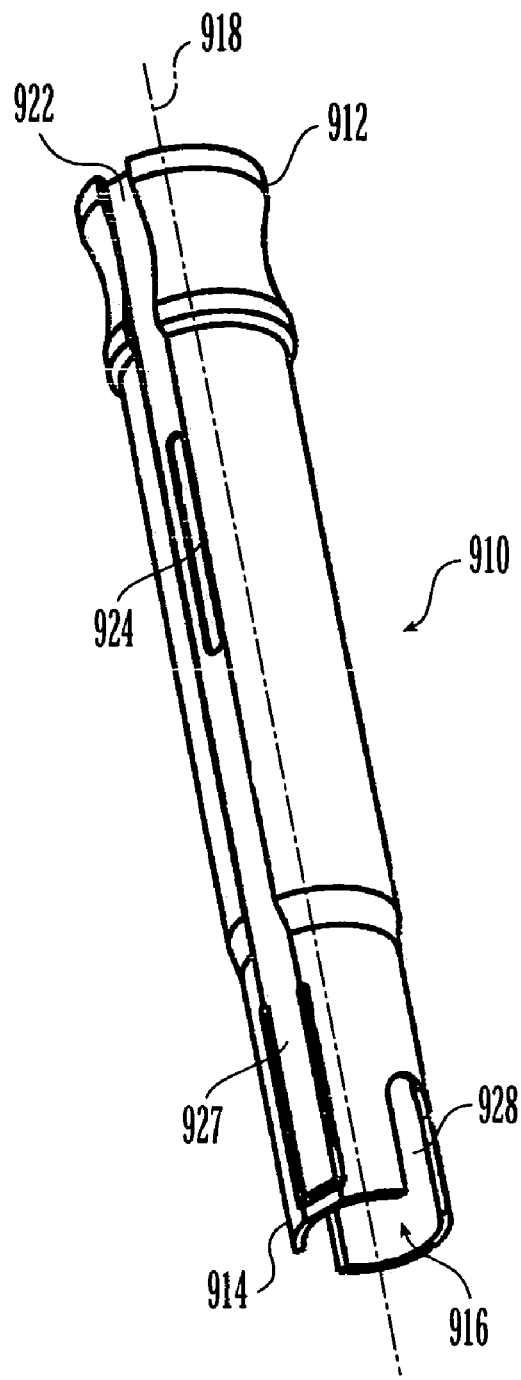
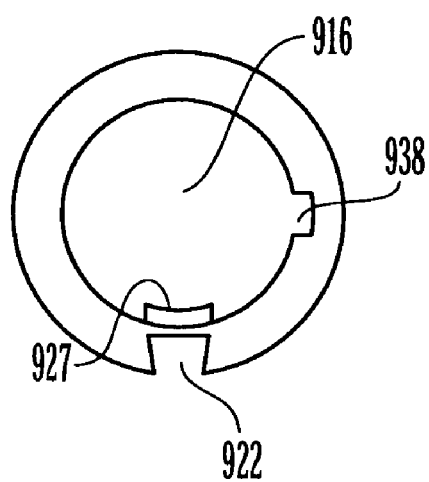
Fig. 9C
Fig. 9B

LESS INVASIVE SURGICAL SYSTEM AND METHODS

FIELD OF THE INVENTION

The present invention is directed to surgical instruments and, in particular, surgical instruments for less invasive procedures for spinal fixation and methods for using the same. Specifically, the less invasive surgical instruments enable an operator to affix a plurality of screws to the spine and introduce a spinal fixation rod therebetween.

BACKGROUND OF THE INVENTION

Spinal fixation systems used to correct spinal deformities generally consist of a series of bone fasteners anchored to the pedicles, lamina or transverse process of the vertebrae. The bone fasteners are interconnected to one another by one or more elongated spinal rods or plates. In order to access the spinal area for implantation of these spinal fixation systems and their individual components, open approach surgical techniques have historically been employed. These open procedures generally involve large skin incisions and extensive tissue retraction and resection, all which may result in considerable post-operative pain and prolonged hospital stays.

More recently, surgeons have used minimally invasive techniques to reduce the post-operative effects of spinal fixation procedures. A paraspinal approach is one form of minimally invasive technique and involves muscle splitting or muscle sparing in order to gain access to the posterior elements of the spine. Such a technique minimizes trauma to tissues adjacent the spine. Unlike open approaches where muscles and other soft tissue are cut, split, stripped and dissected, the paraspinal approach involves separation or splitting of the muscles along their fibers.

To perform a paraspinal surgical procedure, a midline skin incision is made and followed by bi/unilateral fascia incisions. The muscles are then separated to allow bilateral access to the spine via a single skin incision. Additionally, one or more off-midline skin incisions may be made to allow for a more direct approach.

Implanting a spinal rod fixation system generally involves at least two steps: (i) placing implants (e.g., screws) into the spine and (ii) inserting a rod between the implants. Proper placement of the implants requires correctly positioning the implants in the spine. The starting insertion point, the trajectory of the implants and the implants' size are crucial to implant placement.

The spinal implant generally comprises a screw portion and a body portion. The screw portion is inserted into the spine. And, the body portion generally has a channel into which a spinal rod is inserted and secured. The rod insertion procedure requires insertion of the rod through an incision in the skin, which may be separate and distinct from the incision through which the implant(s) is placed. In other embodiments, the rod is inserted through the same incision as the implant(s). The rod connects the implants together.

There exists a need for a less invasive spinal implant and rod introduction system that improves direct visualization, enables a rod to be connected to an implant anchored at varying depths in the body and is generally simple to use.

SUMMARY OF THE INVENTION

The present invention generally relates to instruments for less invasive surgical procedures and, in particular, a less invasive system that may be used for inserting bone screws into the vertebrae and connecting a fixation rod therebetween. The present invention also relates to methods of performing less invasive surgical procedures using these instruments.

The less invasive system may comprise dilation tools, one or more insertion/working cannulas, a plurality of screws, at least one rod for connecting the screws, and a rod inserter. After a surgeon determines an insertion location, an incision may be made in a patient. Dilation tools may then be inserted into the incision to enlarged the incision so that tools may be inserted therethrough. In one embodiment, a guide wire may be inserted down into a vertebra. In an embodiment incorporating a guide wire, the tools used to perform the procedure may be cannulated to receive the guide wire. A series of sequentially larger dilators may be positioned over the guide wire until the incision has been dilated a desirable amount to form an opening in the patient. A retractor may then be inserted over the dilators in a closed position. The dilators may be removed and the retractor may be opened to enlarge the incision to form an opening. Such a method may expose a plurality of vertebrae for fixation. With the incision enlarged, insertion cannulas, bone screws, fixation rod(s) and various surgical tools may be positioned within the opening formed by the retractor.

In one embodiment, a dilation mechanism may be used for increasing the size of an incision to form an opening. The dilation mechanism may comprise at least one dilator having a elongated cylindrical shape with a channel passing therethrough. In addition, the dilation mechanism may comprises a retractor having at least two blades for being inserted through the incision. The at least two blades may have an opened position and a closed position. The blades may be configured to be inserted over the at least one dilator in the closed position and may be configured to move to the opened position to create the opening. Moreover, the dilation mechanism may comprises an inserter, which may have an elongated portion, a proximal end, a distal end and an enlarged portion on the distal end of the elongated portion. The at least one dilator may be configured to receive the inserter therein.

In another embodiment, one or more incisions may be made in a patient and multiple dilators of increasing size may be used to expand the incisions. A working cannula may be positioned over the largest dilator. In one embodiment, the working cannula may have a proximal end, a distal end, and a channel extending from the proximal end to the distal end. The channel of the working cannula may be sized and configured to receive at least one dilator. Once the working cannula(s) are in place, the dilators may be removed. An insertion cannula, bone screws, fixation rod(s) and various surgical tools may be positioned within the working cannula. In an embodiment where the working cannula may be large enough (e.g., where two or more vertebrae may be exposed), multiple insertion cannulas may be inserted through the same working cannula.

In other embodiments, sequential dilators and/or a retractor may be unnecessary. An insertion cannula may be operatively connected to an inserter having a bullet-shaped head and inserted as a single unit into an incision. The inserter may be removed after insertion, leaving the insertion cannula remaining in a patient, through which a procedure may be performed. In one embodiment, the inserter may have an elongated portion, a proximal end, a distal end and an enlarged portion on the distal end of the elongated portion. The inserter may be sized and configured to be received within the passageway of an insertion cannula.

A cavity forming device, such as a drill may be used to form a cavity within each vertebra involved in the procedure. The drill may be passed through the working cannula, retractor and/or the insertion cannula. In other procedures, an awl, probe and/or tap may be used to create a cavity in the vertebrae. However, any means of creating a cavity is envisioned. Once a cavity has been made in a vertebra, screw(s) may then be inserted into the vertebrae. The screws may be polyaxial screws having a shank portion and a head portion. The head portion may have a channel therethrough for receiving a fixation rod and may be connected to the shank portion so that the head portion may pivot about the shank portion. Other procedures may use screws where the shank and head portions may be one piece and fixed with respect to each other.

The screws may be attached to the insertion cannula and inserted as a single unit into the working cannula and/or retractor. With the insertion cannula and screw positioned in the working cannula and/or retractor, an implantation mechanism such as a screwdriver may be inserted in the insertion cannula and engage the screw to drive the screw into bone. In another embodiment, a screwdriver may be inserted in the insertion cannula and engage the screw prior to insertion into a patient. These devices may then be inserted as a single unit into the working cannula and/or retractor. In other embodiments, the insertion cannula may be inserted into the working cannula and/or retractor and, subsequently, a screw and screwdriver may be inserted down into the insertion cannula. In all embodiments, the insertion cannula may be used to manipulate the head portion for enabling insertion of a fixation rod. The implantation mechanism may be used to insert the screw into bone.

In one embodiment, the insertion cannula may have a proximal end, a distal end, a passageway from the proximal end to the distal end, and at least one slot intersecting the passageway. In such an embodiment, the insertion cannula may also comprise a surface and the distal end may comprise a threaded portion on the surface for engaging a spinal fixation device.

In another embodiment, the insertion cannula may comprise a proximal end, a distal end, a passageway from the proximal end to the distal end, at least one slot intersecting the passageway and a flexible portion for engaging a spinal fixation device. The at least one slot may be sized and configured to receive an elongated fixation device. The flexible portion may be a pair of arms defined by two diametrically opposed slots. In such an embodiment, the pair of arms may be configured to snap onto the spinal fixation device. In another embodiment, the flexible portion may comprise at least one flexible member having a first end portion and a second end portion. The first end portion may be operably connected to the insertion cannula and the second end portion may be freely moveable with respect the insertion cannula. The second end portion may be sized and configured to engage the spinal fixation device.

In yet another embodiment, the insertion cannula may comprise a proximal end, a distal end and at least one sidewall, which may define a passageway from the proximal end to the distal end. The insertion cannula may have at least one slot in the at least one sidewall communicating with the passageway and a flexible portion for engaging the spinal fixation device. The flexible portion may comprise a first end portion and a second end portion. The first end portion may be operably connected to the at least one sidewall of the cannula and the second end portion may be freely moveable into and out of the passageway of the cannula. The second end portion may be engagable with a spinal fixation device.

In another embodiment, the insertion cannula may comprise an inner cannulated shaft having a proximal end, a distal end and a bore therethrough. In addition, the insertion cannula may comprise an outer cannulated shaft having a proximal end, a distal end, and a bore therethrough. The bore of the outer cannulated shaft may be sized and configured to receive the inner cannulated shaft. In this embodiment, the flexible portion may comprise at least one flexible member having a first end portion and a second end portion. The first end portion may be operably connected to the inner cannulated shaft and the second end portion may be freely moveable with respect the inner cannulated shaft. The outer cannulated shaft may be sized and configured to travel along the inner cannulated shaft from a first position to a second position and move the second end portion of the at least one flexible member towards the spinal fixation device. Moreover, the inner cannulated shaft may comprise a slot and the outer cannulated shaft comprises a protrusion, which may be engagable with the slot. The slot may have at least one notch and may be sized and configured for positioning the outer cannulated shaft at at least one location on the inner cannulated shaft.

In yet another embodiment, the cannula may comprise a cannulated shaft having a longitudinal recess and an elongated member positionable within the recess. In this embodiment, the flexible portion may comprise at least one flexible member having a first end portion and a second end portion. The first end portion may be operably connected to the cannulated shaft and the second end portion may be freely moveable with respect the cannulated shaft. The elongated member may be sized and configured to engage the at least one flexible member such that the at least one flexible member may be moved towards the spinal fixation device.

Furthermore, in one embodiment, an implantation mechanism may be sized and configured to be inserted into the passageway of an insertion cannula. The implantation mechanism may comprise a shaft having a proximal end, a distal end, and an engagement portion on the distal end sized and configured to engage the spinal fixation device. Furthermore, the implantation mechanism may comprise a protrusion on the engagement portion, which may engage a longitudinal recess of an inner cannulated shaft. The protrusion may be moveable along the recess. The protrusion and longitudinal recess may be configured to align the at least one slot of the cannula relative to the spinal fixation device.

Moreover, in other embodiments, the implantation mechanism may further comprises a first sleeve having a proximal end and a distal end. The first sleeve may be positionable around the shaft. The engagement portion may comprise a protruding portion and at least one shoulder portion. The protruding portion may engage the shank portion of an implant and the at least one shoulder portion may engage the channel of the head portion of the implant. The head portion of the spinal fixation device may have internal threads and the distal end of the first sleeve may have a threaded portion, the threaded portion of the first sleeve may be sized and configured to engage the internal threads of the head portion of the spinal fixation device.

In another embodiment, an implant positioner may be sized and configured to be inserted into the passageway of the cannula. The implant positioner may have an elongated shaft, a proximal end, a distal end and an engaging portion on the distal end sized and configured to engage a spinal fixation device and manipulate the spinal fixation device relative to the cannula.

A fixation device inserter may be used to insert a fixation rod into the head portions of the screws. In one embodiment, a separate incision may be made in a patient at a distance from the incision(s) used to insert the screws. The fixation device inserter may be coupled to a fixation rod and may be used to insert the fixation rod through the separate incision and into the side of the head portion of the screws. In one such embodiment, the a fixation device inserter may comprise an elongated shaft and a moveable member having a proximal end, a distal end and an engaging portion at the distal end for engaging an elongated fixation rod. The moveable member may be positioned within the elongated shaft. Moreover, the fixation device inserter may comprise an actuation mechanism operably associated with the moveable member. The actuation mechanism may be configured to move the moveable member between a first position and a second position.

In another embodiment, the rod inserter may be used to position a fixation rod down through the insertion cannula into the head portion through the top of the screw. Once the fixation rod is in place, a locking cap may be positioned down the working cannula, retractor and/or insertion cannula and engaged to the head portion of the screws such that the fixation rod may be fixed therein.

The method for performing a less invasive procedure, in one embodiment, may comprise providing a first cannula having a flexible portion, providing a second cannula and providing a first and second implant. The first and second implant may comprise a shank portion, a head portion and a channel passing through the head portion for receiving an elongated fixation device. The method may further comprise attaching the flexible portion of the first cannula to the first implant and attaching the second cannula to the second implant. Furthermore, the first implant may be inserted into a first vertebrae and the second implant may be inserted into a second vertebrae. Additionally, an elongated fixation device may be inserted into the channel of the head portion of the first and second implants. The elongated fixation device may be locking in the head portion of the first and second implants. In an embodiment where the flexible portion may be a pair of arms, the method may further comprise snapping the head portion of the first implant between the pair of arm. Moreover, an implant positioner may be inserted into at least one of the first and second cannulas to manipulate the head portion of at least one of the first and second implants relative to at least one of the first and second cannulas.

In another embodiment, the method may further comprise providing a fixation device inserter having an elongated shaft, a moveable member positioned within the elongated shaft for engaging the elongated fixation rod, and an actuation mechanism operably associated with the moveable member. The actuation mechanism may be configured to move the moveable member between a first position and a second position. The method may additionally comprise inserting a first implant and first cannula through at least one of a first opening and a first incision, and inserting a second implant and second cannula through at least one of the first opening, the first incision and a second opening. Moreover, the method may comprise creating at least one of a third incision and a third opening and using the fixation device inserter to position the elongated fixation device through one of the third incision and third opening, and into the channel of the head portion of at least one of the first and second implants.

In another embodiment, the method for performing a less invasive procedure may comprise providing a first cannula having a threaded portion, providing a second cannula and providing a first and second implant. The first and second implant may comprise a shank portion, a head portion and a channel passing through the head portion for receiving an elongated fixation device. The head portion of the first implant may also have threads. The method may further comprise engaging the threaded portion of the first cannula to the threads of the first implant and attaching the second cannula to the second implant. Furthermore, the first implant may be inserted into a first vertebrae and the second implant may be inserted into a second vertebrae. Additionally, an elongated fixation device may be inserted into the channel of the head portion of the first and second implants. The elongated fixation device may be locking in the head portion of the first and second implants.

In yet another embodiment, the method may comprise making an incision and inserting a shank portion of an implant into a vertebrae. The method may further comprise engaging the shank portion with an implantation mechanism. The head portion may be engaged with a cannula to form a unit, which may be inserted into the incision. Additionally, the method may comprise engaging the head portion with the shank of the implant after the shank portion of the implant has been inserted into the vertebrae.

BRIEF DESCRIPTION OF THE DRAWINGS

The present invention can be better understood by reference to the following drawings, wherein like references numerals represent like elements. The drawings are merely exemplary to illustrate certain features that may be used singularly or in combination with other features and the present invention should not be limited to the embodiments shown.

FIG. 9B is a perspective view of an exemplary embodiment of a portion of the insertion cannula of FIG. 9A;

FIG. 9C is a top view of the portion of FIG. 9B;

DETAILED DESCRIPTION

The less invasive system of the present invention may comprise a means for dilating an incision in a patient (e.g., sequential dilator, retractor), at least one insertion/working cannula, a plurality of screws, at least one rod for connecting the screws, and a rod inserter. It should, however, be understood that those of ordinary skill in the art will recognize many modifications and substitutions which may be made to various elements of the present invention. And, while the instruments and implants may be described with reference to implanting in the vertebrae, they may be used in other surgeries in other locations in a patient.

A. Dilation Tools

A radiographic image may be taken of the spine, including the vertebrae which are to receive implants. From the radiographic image, an insertion point may be located on a patient's back. An incision may then be made into the patient's back to form an opening through which the less invasive system may be used. The opening may then be dilated. It will be understood by those skilled in the art that dilation of an opening in a patient may be performed using any number of devices, including the devices described in further detail below.

1. Trocar and Guide Wire

Figure 1:
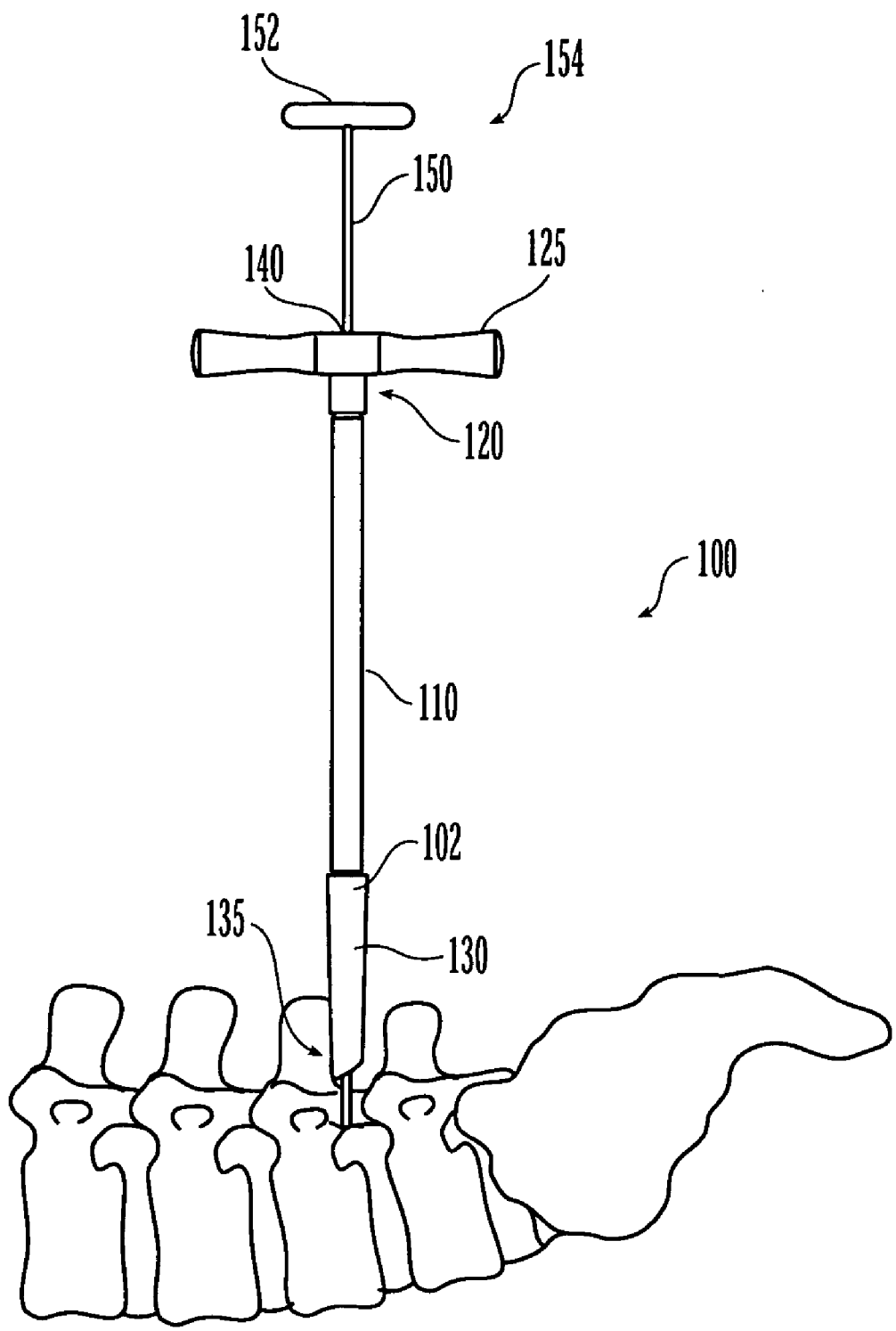
FIG. 1 is a side view of an exemplary embodiment of a trocar and an exemplary embodiment of a guide wire positioned in the spine.

As shown in FIG. 1, a trocar 100 may be an elongated member 110 having a proximal end 120 and a distal end 130. The trocar 100 may be inserted through the incision in the patient—for example, using fluoroscopic guidance—and may engage a vertebra. The distal end 130 of the trocar 100 may have a point 135 for puncturing and/or forming a hole through the cortex of the vertebra. Moreover, the trocar 100 may have an enlarged front portion 102 on the distal end 130 of the trocar 100. The enlarged front portion 102 may assist in increasing the size of the opening and creating a percutaneous passageway to a vertebra. And, in an alternative embodiment, the distal end 130 of the trocar 100 may have threads (not shown) for engaging a vertebra to hold the trocar 100 in place on a vertebra.

Additionally, the proximal end 120 of the trocar 100 may have a handle 125. A handle 125 may make it easier for an operator to use/manipulate the trocar 100. The handle 125 may be integrally formed with the elongated member 110 or it may be mechanically joined at the proximal end 120. The handle may be radiolucent so that it may be invisible under fluoroscopic observation or when using X-rays. Moreover, the handle 125 may be removable. In one embodiment, the handle 125 may be T-shaped. In another embodiment, the handle 125 may be spherical in shape. Further, the trocar 100 may comprise a channel 140 therethrough which may extend from the proximal end 120 to the distal end 130.

A guide wire or rod 150 may be inserted through the channel 140 at the proximal end 120 of the trocar 100 and may be positioned in the hole formed in the pedicle by the trocar 100. In an embodiment having a handle 125, the guide wire 150 may also be inserted through the handle 125. A guide wire 150, such as that shown in FIG. 1, may be used to guide various devices and/or implants into a patient and towards the spine. For example, the guide wire 150 may be used to guide dilators, insertion/working cannulas, a drill, a screwdriver, and implants (e.g., bone screws) to a location on the spine. It should be noted that any device described herein may be inserted into a patient without the use of the guide wire 150. The guide wire 150 may be inserted down through the channel 140 until it engaged the vertebra. Thereafter, a surgical mallet or other striking instrument (not shown) may be used to hammer the guide wire 150 into the hole formed by the trocar 100. In this way, the guide wire 150 may be anchored to the vertebra.

To assist an operator to hammer the guide wire 150 into a vertebra, the guide wire 150 may comprise a cap 152, which may be located at a proximal end 154 of the guide wire 150. Such a construction may provide an operator with an enlarged surface for striking a mallet or other instrument against the guide wire 150. The cap 152 may be made of metal, plastic, rubber or any other material that may withstand repeated impact. Moreover, the cap 152 may be any shape (e.g., circular, polygonal, spherical) or size. In addition, the cap 152 may be engagable with another component (e.g., a slap hammer), which may be used to implant the guide wire 150 into bone.

The step of inserting the trocar 100/guide wire 150 may be repeated any number of times through separate incisions or the same incision, depending on how many vertebrae and/or the number of implants that may be involved in the procedure being performed.

2. Dilator

Once the guide wire 150 is in place, the trocar 100 may be removed from the patient's body. A sequential dilator system such as disclosed in U.S. patent application Ser. No. 10/884,705 filed Jul. 2, 2004, entitled Sequential Dilator System, the entire content of which is hereby incorporated by reference, may be used to enlarge the opening in the patient. It should be understood, however, that any dilator system may be used with the less invasive system.

Figure 2:
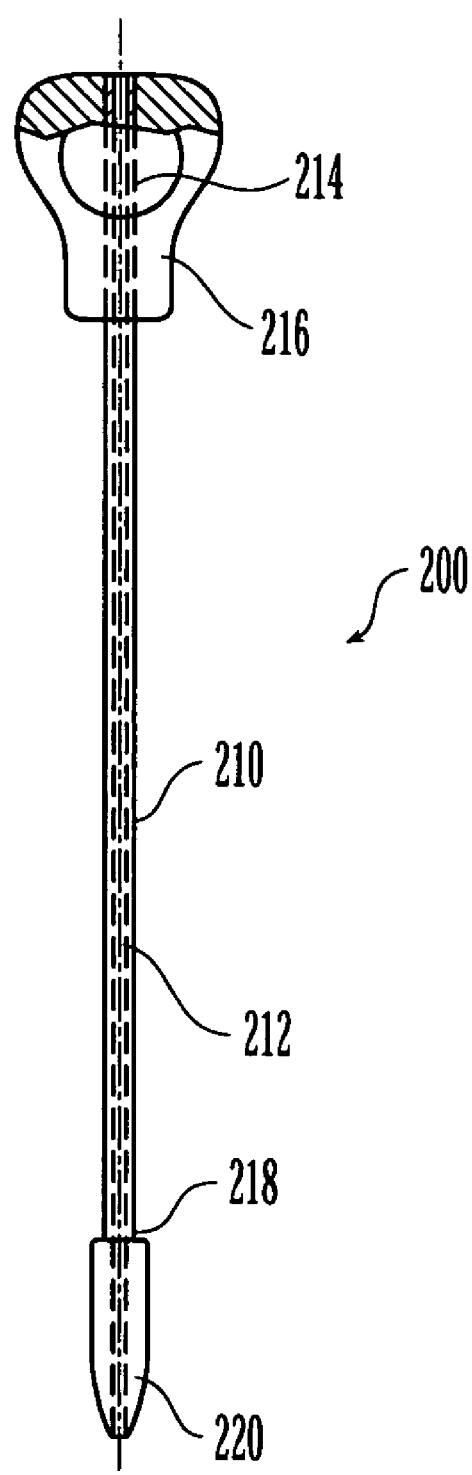
FIG. 2 is a partial cross-sectional view of an exemplary embodiment of an inserter.

A dilator inserter 200, such as the one shown in FIG. 2, may be inserted over the guide wire 150 down towards the surgical site proximate a vertebra. The dilator inserter 200 may comprise an elongated shaft 210, which may have a central bore 212 in which the guide wire 150 may be received. The dilator inserter 200 may have a handle 216 at its proximal end 214 and an bullet-shaped tip 220 at its distal end 218. The handle 216 may be removable to allow one or more dilator tubes 350 (FIG. 3A) to be inserted over the dilator inserter 200. Moreover, the bullet-shaped tip 220 may assist in enlarging the opening and created an enlarged percutaneous pathway to a vertebra. The tip 220, however, may be any shape and may or may not be enlarged.

Figure 3A:
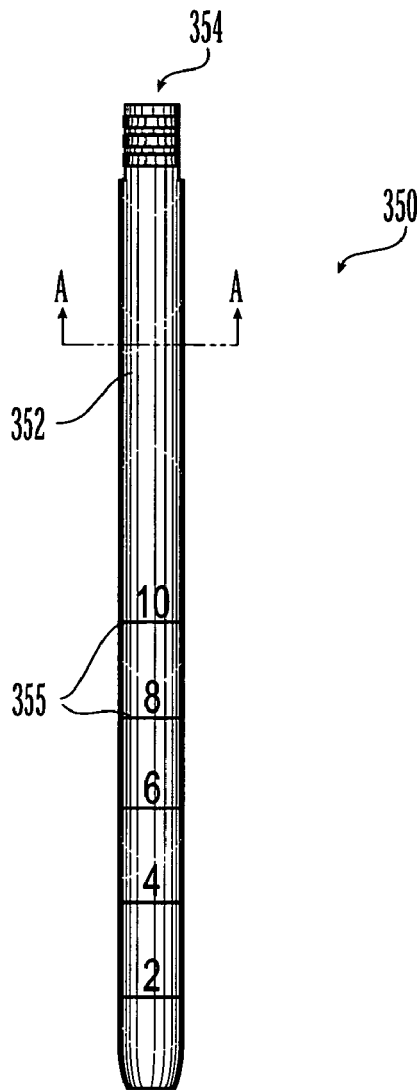
FIG. 3A is a side view of an exemplary embodiment of a dilator.

Once the dilator inserter 200 is in place, one or more different sized dilator tubes 350 such as shown in FIG. 3A may be inserted over the dilator inserter 200. It should be noted that a dilator inserter 200 may not be used and one or more dilator tubes 350 may be inserted directly over the guide wire 150. The dilator tubes 350 may have an elongated shaft 352 with a channel 354 therethrough dimensioned and configured for receiving the dilator inserter 200 and/or other dilators 350. In addition, the dilator tube 350 may have markings 355, which may provide an operator with a visual indication of the depth of the dilator 350 within the body of a patient.

Figure 3B:
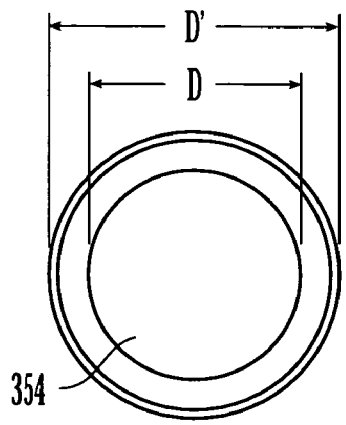
FIG. 3B is a top view of the dilator of FIG. 3A along A-A.

A first dilator 350, which may have an inner diameter D (FIG. 3B), may be positioned over the dilator inserter 200 and down to a surgical site proximate a vertebra. It should be understood, however, that the dilator inserter 200 and a first dilator 350 may be attached to each other and inserted into the body as a single unit. The inserter 200 may then be removed from the first dilator 350. Thereafter, a second dilator 350 having an inner diameter greater than the outer diameter D' of the first dilator 350 may be inserted over the first dilator 350. This process may be repeated numerous times with sequentially larger dilators 350 until the opening has been dilated to a size desired by the surgeon and appropriate for the procedure to be performed (e.g., large enough to receive implants and/or instruments). And, in an embodiment where multiple openings may be used for a procedure, the dilation process may be repeated for each opening.

Figure 4A:
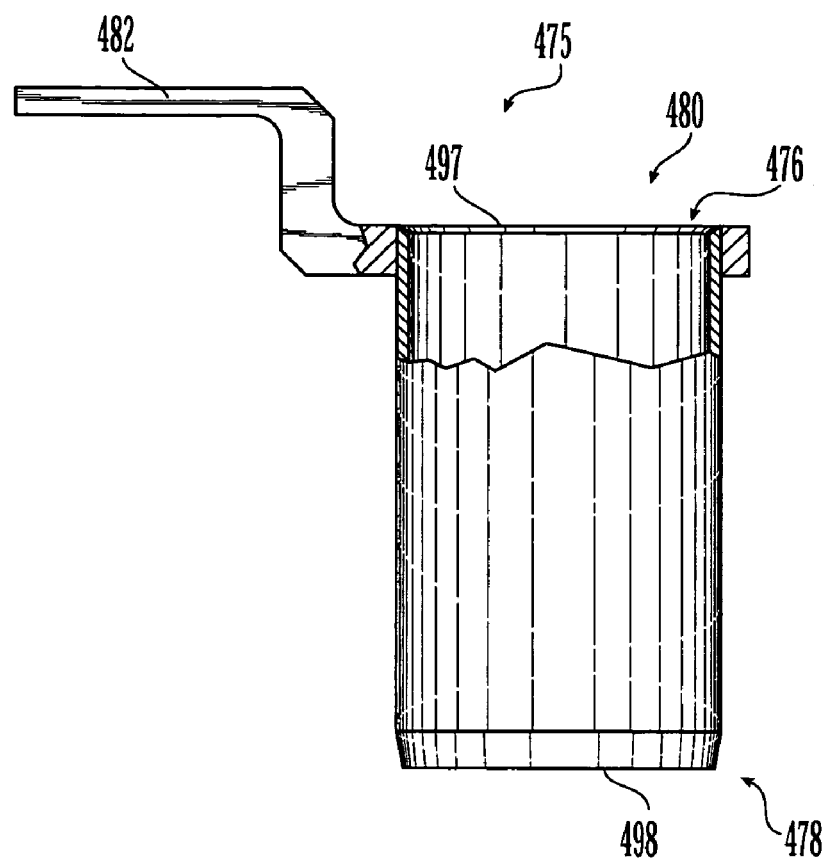
FIG. 4A is a partial cross-sectional view of an exemplary embodiment of a working cannula.
Figure 4B:
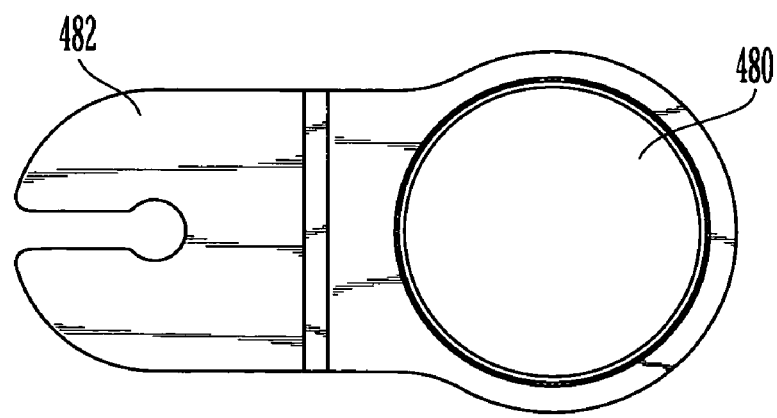
FIG. 4B is a top view of the working cannula of FIG. 4A

In one embodiment, after the largest dilator 350 is in place, a working cannula 475 (FIGS. 4A and 4B) may be positioned over the dilators 350 and down to the surgical site proximate the vertebra to be operated on. The working cannula 475 may have a proximal end 476, which may remain accessible to the surgeon, and a distal end 478 which, upon insertion of the working cannula 475, may be located adjacent the surgical site. In addition, the working cannula 475 may have a channel 480 extending from an opening 497 at the proximal end 476 to an opening 498 at the distal end 478 through which an operator may insert implants and surgical instruments. The working cannula 475 may have a constant diameter from the proximal end 476 to the distal end 478. Moreover, the working cannula 475 may have a handle 482 at its proximal end 476 to allow a surgeon to grab the working cannula 475 during surgery and/or enable the working cannula 475 to be attached to an operating table. In this way, the working cannula 475 may be held stationary during surgery.

Once the working cannula 475 is in place, all dilators 350 and/or the guide wire 150 may be removed from the body. In one embodiment, the guide wire 150 may remain in place to guide implants and instruments to a surgical site. Each dilator 350, however, may be removed after a larger dilator 350 is positioned thereover. Different parts of a procedure may be performed through different working cannulas 475. If the working cannula 475 is large enough and expose multiple vertebrae, an entire procedure may be performed through a single working cannula 475 (i.e., without making another opening in the patient). Nevertheless, other means of dilating an opening may also be used in addition to or in place of dilators 350 such as, for example, a retractor.

3. Retractor

Figure 5A:
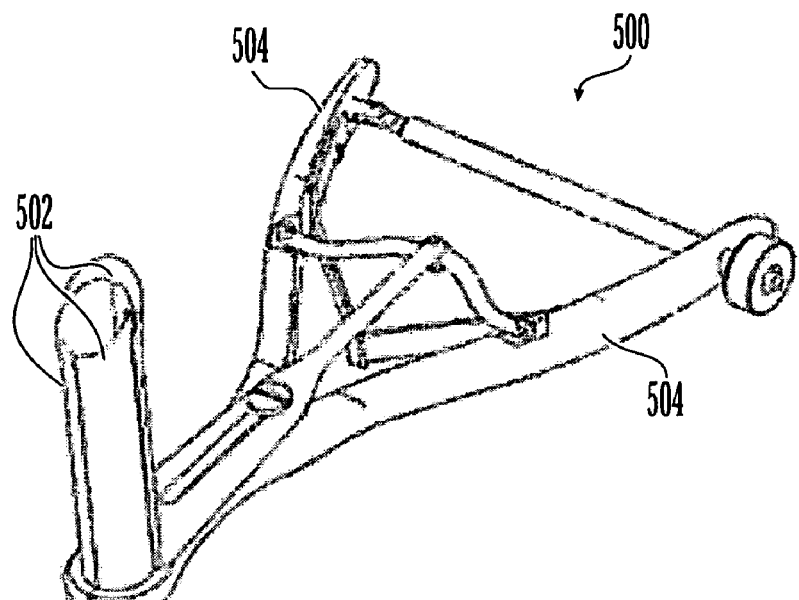
FIGS. 5A and 5B are perspective views of an exemplary embodiment of a retractor in a closed position (FIG. 5A) and an opened position (FIG. 5B)
Figure 5B:
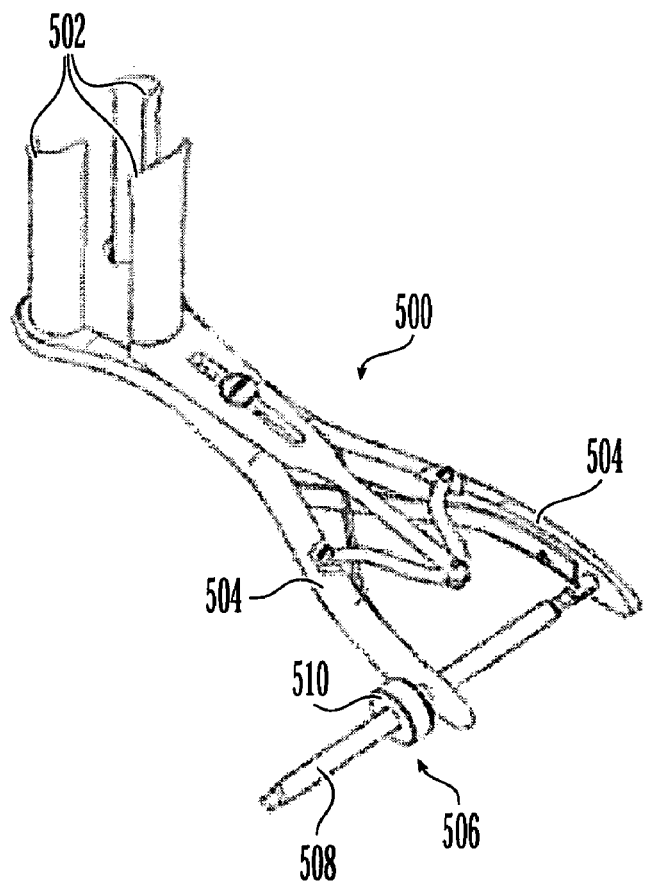

A retractor 500, such as disclosed in U.S. patent application Ser. No. 10/917,560, filed Aug. 13, 2004, entitled Multiple-Blade Retractor, the entire content of which is hereby incorporated by reference, may also be used to enlarge an opening in a patient. In one embodiment, the blades 502 of the retractor 500 may be positioned over at least one dilator 350 into the opening in a closed position (FIG. 5A). In another embodiment, the retractor 500 may be inserted directly into an opening in a patient without the use of a dilator 350. Once the retractor 500 is in the opening in a patient, the handles 504 of the retractor 500 may then be squeezed together and the blades 502 may be spread apart (FIG. 5B). The blades 502 may be locked in the opened position using a locking mechanism 506. The locking mechanism 506 may comprise a threaded rod 508 and a nut 510. The nut 510 may be turned on the threaded rod 508 until it engages a handle 504. However, any means of locking the retractor 500 may be used to keep the retractor in an opening position. All subsequent surgical procedures may be performed inside the enlarged opening created by the blades 502 of the retractor 500 (i.e., between the blades 502). It will be appreciated by those skill in the art that any other retractor known in the surgical art may also be used to enlarge an opening in a patient.

B. Implantation Tools

1. Bone Screw

Figure 6A:
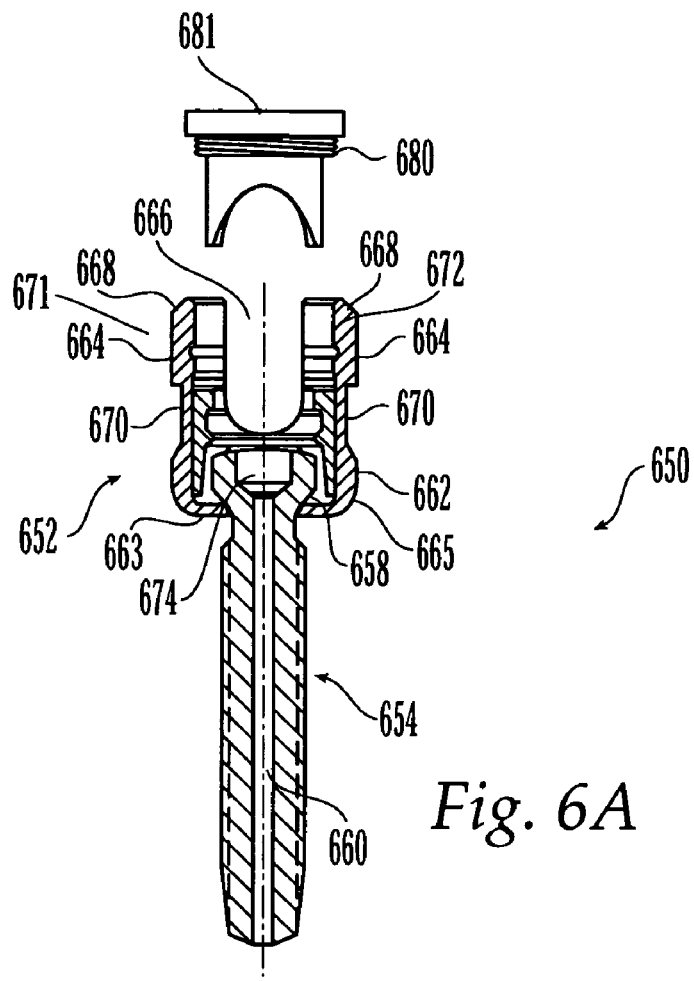
FIG. 6A is a cross-sectional view of an exemplary embodiment of a screw.
Figure 6B:
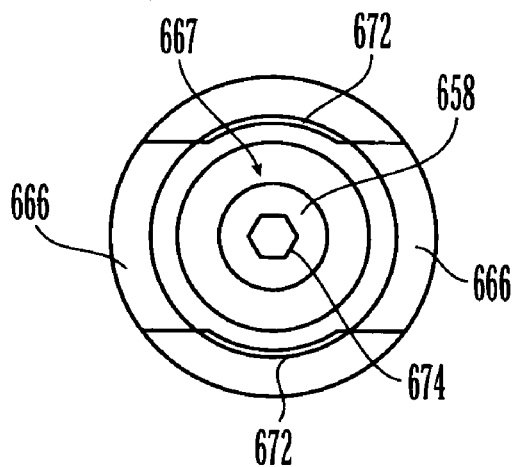
FIG. 6B is a top view of an exemplary embodiment of the screw of FIG. 6A.

In one embodiment of the present invention as shown in FIGS. 6A and 6B, the implant to be inserted into a vertebra may be a polyaxial screw 650. It is contemplated, however, that any screw may be used with the less invasive system so long as the screw incorporates or may be attached to a rod receiving channel sized and configured to receive a spinal rod. The bone screw 650 may comprise a shank portion 654 and a head portion 652 operably connected to the shank portion 654. The shank portion 654 may be threaded and the threads may be self tapping. The bone screw 650 may be polyaxial such that the head portion 652 articulates and is rotatable with respect to the shank portion 654. The shank portion 654 may be a separate piece from the head portion 652 and may engage the head portion 652. The shank portion 654 may also be integral with the head portion 652 so that there is no movement between the two portions.

The shank portion 654 may have a proximal end 658 which may be received within the head portion 652. In one embodiment, the shank portion 654 may be snapped into the head portion 652. The proximal end 658 of the shank portion 654 may also have a surgical tool engaging recess 674 such as, for example, in the form of hexagon for receiving a corresponding hexagonal portion of a surgical tool. Moreover, the shank portion 654 may have a central axial channel 660, which may receive a guide wire 150 so that the screw 650 may be guided to the surgical site proximate a vertebra. Other shapes and configurations of the shank portion 654 and head portion 652 may be utilized to obtain polyaxial rotation between the head portion 652 and the shank portion 654.

As shown in FIGS. 6A and 6B, the head portion 652 may be cylindrical and may comprise a base portion 662 and two spaced apart arms 664. The arms 664 may have chamfered edges 668 and recesses 670 to engage surgical tools (e.g., various insertion cannulas discussed below). In one embodiment, the arms 664 may have external threads (not shown) for engaging various insertion cannulas and/or other surgical tools. The head portion 652 may also have a central bore 667. The central bore 667 may pass through the head portion 652 such that the proximal end 658 of the shank portion 654 may extend through a distal opening 663 in the distal end 665 of the head portion 652. The arms 664 may form a channel 666 that may intersect the central bore 667. The channel 666 may be any shape (e.g., U-shaped) and may receive a fixation rod. Further, the head portion 652 may have internal threads 672 on the walls of the bore 667 for engaging corresponding external threads 680 on a cap 681 and/or a surgical instrument (e.g., screwdriver, insertion cannula, etc.). The cap 681 may be received within the bore 667. Other caps interacting with different mechanisms at the proximal end 671 of the head portion 652 may be used to retain the fixation rod within the bone screw.

2. Insertion Cannula

An insertion cannula may be used for insertion of an implant (e.g., screw, fixation rod). It should, however, be understood by those skilled in the art that it may not be necessary to use a insertion cannula for all procedures. The insertion cannula may be connected to a screw 650 and/or other tool(s) (e.g., a screwdriver) and, as one unit, may be inserted through the working cannula 475 and/or the opening created by the retractor 500. In another embodiment, the screw 650 and/or other tool(s) may be inserted into the insertion cannula after the insertion cannula has been positioned into a patient. In an embodiment using a guide wire 150, the insertion cannula, screw 650, and/or other tool (e.g. screwdriver) may be inserted down over the guide wire 150 to the vertebrae.

The type of insertion cannula used may depend on, for example, the preference of the surgeon, the anatomy of the body and/or the requirements of the surgical procedure. In particular, the insertion cannula chosen may be a factor of the method by which the fixation rod may be inserted into a bone screw. In some embodiments, the insertion cannula may be designed for insertion of the fixation rod from the side of the bone screw. In these embodiment, the fixation rod may be inserted through an incision which may be separate from the incision through which the bone screws were inserted into a patient. In other embodiments, the insertion cannula may be designed for insertion of the spinal rod through the top of a bone screw. And, a spinal rod may be inserted through the same incision which the bone screws were inserted through. In other embodiments, the insertion cannula may be configured to enable a rod to be inserted from either the top or side of a bone screw.

In an embodiment where no working cannula 475 or retractor 500 is used, the insertion cannula may be connected to inserter 200 (which may be specially designed to fit within the insertion cannula) and may be inserted as a single unit with inserter 200 through the incision in the patient. A guide wire 150 may be used to guide the inserter/cannula construction down to a vertebra. The inserter 200 and/or guide wire 150 (if used) may be withdrawn from the insertion cannula and all steps of a procedure may be performed through the insertion cannula. For example, a drill, bone screw, screwdriver, fixation rod and other surgical tools may be inserted through the insertion cannula. In other embodiments, an insertion cannula may be inserted directly into an opening in a patient without the use of any additional instruments. Thus, the insertion cannula may perform the function of dilating/retracting an opening.

It should be noted, however, that any combination of instruments (e.g., trocar 100, guide wire 150, inserter 200, dilator (s) 350, working cannula 475 and/or retractor 500) may be used to assist in inserting an insertion cannula into the body of a patient.

In performing a less invasive procedure, more than one insertion cannula, such as those discussed below, may be used, for example, to insert bone screws 650 into adjacent vertebrae and hold and manipulate the bone screws 650. The insertion cannulas may be inserted through separate incisions in a patient and/or may be inserted through the same incision. For example, in an embodiment where a working cannula 475 may be used, separate incisions may have separate working cannulas 475 and separate insertion cannulas may be inserted through each working cannula 475 down to the vertebrae. It should be appreciated that if a working cannula 475 is large enough, multiple insertion cannulas may be inserted into the working cannula 475. Moreover, in an embodiment where a retractor 500 may be used, multiple insertion cannulas may also be inserted through the opening created by the retractor 500. In such embodiments, the entire procedure may be performed through the working cannula(s) 475 or retractor 500.

One advantage of the insertion cannulas may be that the orientation of the head portion 652 may be visible through the proximal ends of each cannula. As such, a surgeon may be able to verify the location of a fixation rod in the channel 666. To further enhance a surgeon's ability to see down into a surgical site, any of the insertion cannulas described below may have a light source. In addition, the insertion cannulas may comprise a suction-irrigation system to remove fluid and tissue that may be obstructing a surgeon's view of a surgical site, thereby improving the surgeon's view of the surgical site. Moreover, a microscope or endoscope (not shown) may be attached to the insertion cannulas to provide a magnified view of a surgical site. And, where a procedure requires stabilization of the insertion cannulas, the insertion cannulas may be connected to one of any number of attachments such as, for example, the SYNTHES® Spine Synframe Access and Retractor System. These attachments may be attached, for example, to an operating table and may hold the insertion cannulas in place with respect to the patient, thereby eliminating the need for a surgeon or a nurse to hold the cannulas during surgery.

Furthermore, the components of any insertion cannula discussed herein may be made, for example, of metal, plastic, rubber, a combination of materials or a composite material. For example, the components may be made from stainless steel, titanium, aluminum, an alloy, carbon fiber composite, or a polymer (e.g., polyvinyl chloride (PVC), polyethylene, polyesters of various sorts, polycarbonate, Teflon coated metal, polyetherether ketone (PEEK), ultra high molecular weight polyethylene (UHMWPE)). And, the components of the insertion cannulas may have a non-glare coating and/or may be radiolucent. In addition, the components of the insertion cannula may be made, for example, by casting, extrusion, injection molding, compression molding, forging, machining, or transfer molding.

Various factors can be considered when determining the material used to make the various components of the insertion cannulas, including the ability to withstand sterilization/cleaning (e.g., using an autoclave; cleaning products used for sterilization in hospitals), weight, durability, resistance to staining (e.g., from blood or substances used in surgery) and the ability to grip the components, particularly with latex gloves which are generally used during surgery.

Furthermore, while the cannulated shafts of the insertion cannulas discussed below may be illustrated having circular cross-sections, the cross-sections may be any shape, for example, oval, square, rectangular, triangular, or otherwise polygonal.

a. Side Insertion Cannula

Figure 7A:
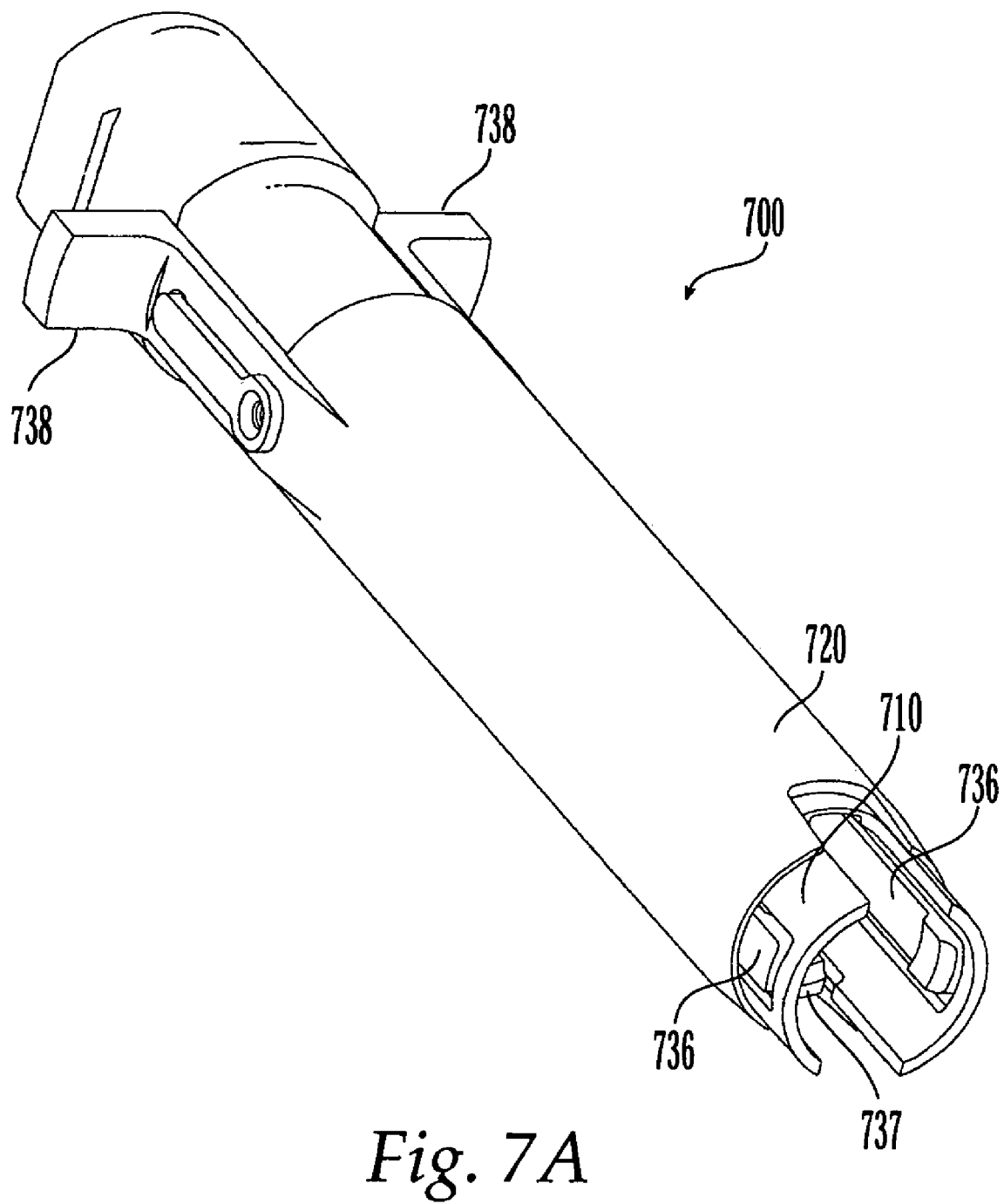
FIG. 7A is a perspective view of an exemplary embodiment of an insertion cannula.
Figure 7B:
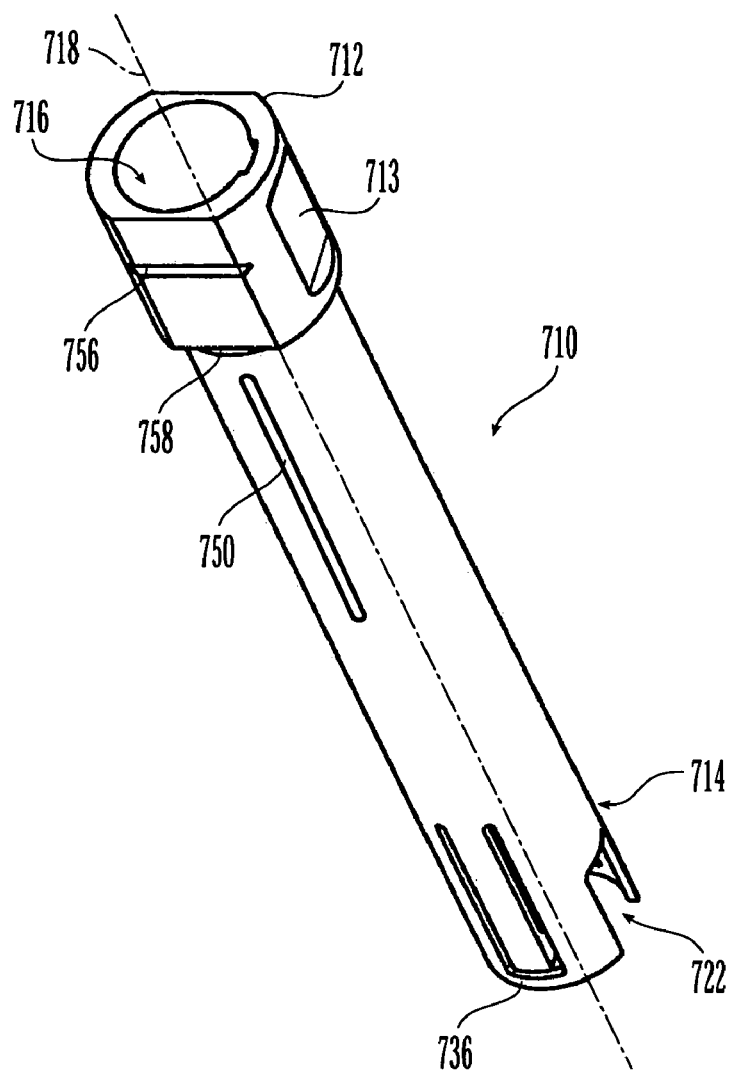
FIG. 7B is a perspective view of an exemplary embodiment of an inner portion of the insertion cannula of FIG. 7A.
Figure 7C:
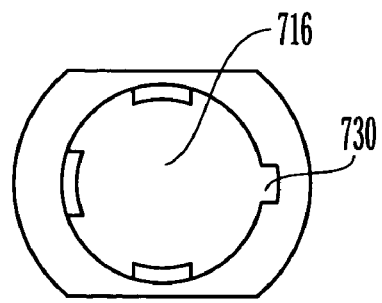
FIG. 7C is a top view of the inner portion of FIG. 7B.

As shown in FIG. 7A, an insertion cannula 700 may comprise an inner cannulated shaft 710 received within an outer cannulated shaft 720. Furthermore, as illustrated in FIGS. 7B and 7C, the inner cannulated shaft 710 may have a proximal end 712, a distal end 714 and a bore 716 extending from the proximal end 712 to the distal end 714. The bore 716 may define a central axis 718 and may be dimensioned and configured for receiving a spinal implant (e.g., bone screw) and/or surgical instruments. The bore 716 may also be configured to be positioned over the guide wire 150, inserter 200 and/or at least one dilator 350. A channel or slot 722 may be located at the distal end 714 of the inner cannulated shaft 710 and may extend at an angle (e.g., perpendicular) to the central axis 718. The channel or slot 722 may be U-shaped (although other shapes are contemplated) and may accommodate at least a portion of a fixation rod which may be inserted therethrough as will be described in greater detail below.

The inner cannulated shaft 710 may have an inner diameter, for example, between about 3 mm and about 20 mm and, more preferably, between about 12 mm and about 15 mm. However, the inner diameter may be any size so long as a screw 650 and/or tools may be positioned therethrough. The inner cannulated shaft 710 may have an outer diameter, for example, between about 3 mm and about 20 mm and, more preferably, between about 14 mm and about 17 mm. Moreover, the inner cannulated shaft 710 may have a length, for example, between about 40 mm and about 160 mm and, more preferably, between about 110 mm and about 130 mm. The channel or slot 722 may have a width, for example, between about 3 mm and about 10 mm and, more preferably between about 4 mm and about 7 mm. The channel or slot 722 may also have a height, for example, between about 3 mm and about 20 mm and, more preferably, between about 10 mm and about 14 mm. It should be noted that these dimensions may also be applicable to the inner cannulated shaft of FIG. 8B discussed below.

Figure 7D:
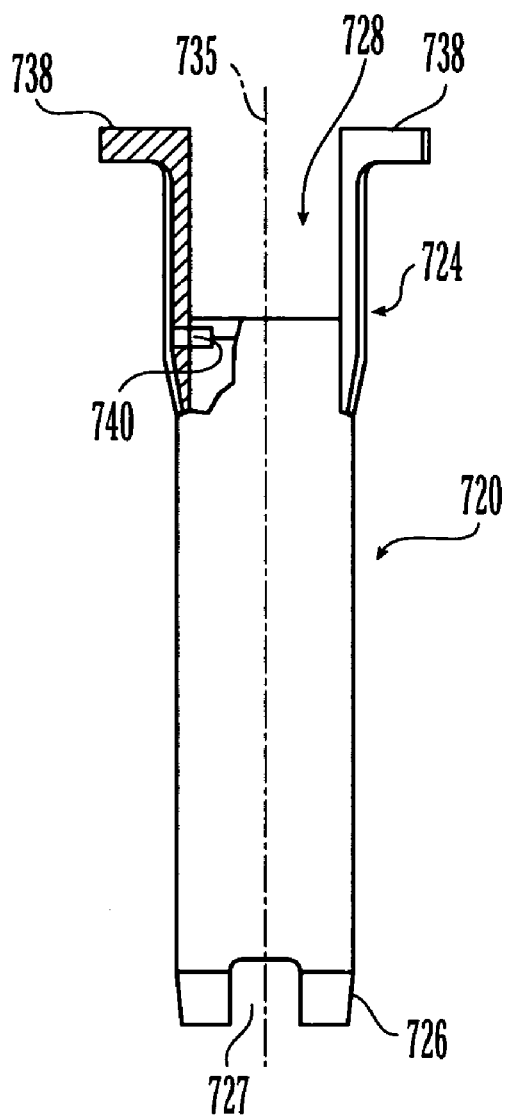
FIG. 7D is a partial cross-sectional view of an exemplary embodiment of an outer portion of the insertion cannula of FIG. 7A.
Figure 7E:
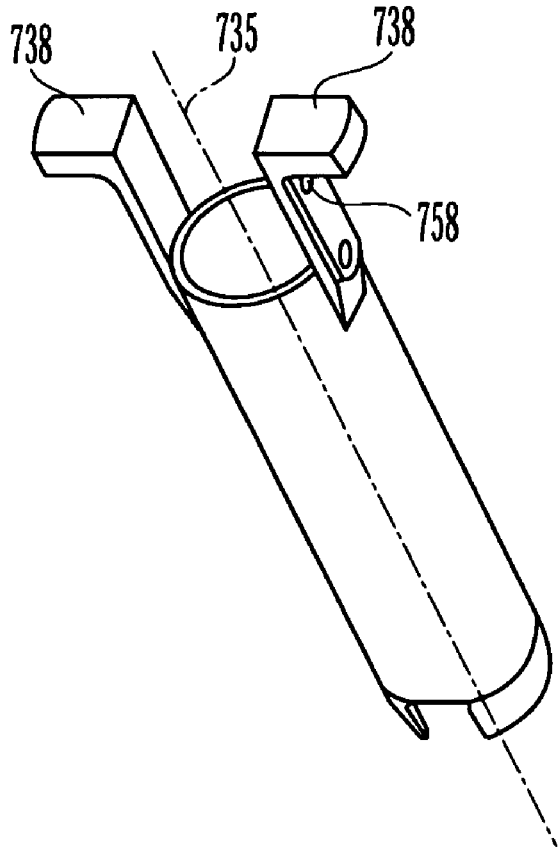
FIG. 7E is a perspective view of the outer portion of FIG. 7D.

FIGS. 7D and 7E illustrate an embodiment of the outer cannulated shaft 720. The outer cannulated shaft 720 may have a proximal end 724, a distal end 726 and a bore 728 extending from the proximal end 724 to the distal end 726. The bore 728 may define a central axis 735 and may be dimensioned and configured to receive the inner cannulated shaft 710. The outer cannulated shaft 720 may be shorter in length than the inner cannulated shaft 710 so as to permit the full length of the outer cannulated shaft 720 to slide along the exterior of the inner cannulated shaft 710 for reasons that will become apparent below. And, the distal end 726 of the outer cannulated shaft 720 may taper inwardly for close engagement with the distal end 714 the inner cannulated shaft 710.

The outer cannulated shaft 720 may have an inner diameter, which may be larger than the outer diameter of the inner cannulated shaft 710, and an outer diameter, for example, between about 3 mm and about 20 mm and, more preferably, between about 16 mm and about 19 mm. Moreover, the outer cannulated shaft 720 may have a length, for example, between about 20 mm and about 140 mm and, more preferably, between about 70 mm and about 80 mm. It should be noted that these dimensions may also be applicable to the outer cannulated shaft of FIG. 8E discussed below.

In order to prevent rotation of the outer cannulated shaft 720 with respect to the inner cannulated shaft 710 and/or keep the two components aligned, the outer cannulated shaft 720 may have at least one projection 740 (FIG. 7D) located on an interior wall of the bore 728 for engagement with at least one slot 750 (FIG. 7B) in the wall of the inner cannulated shaft 710. In one embodiment, the projection 740 may be a screw, pin, or bolt which passes through opening 760 (FIG. 7F) to engage the spring detent 752 to the outer cannulated shaft 720. Alternatively, the inner cannulated shaft 710 may have the projection and the outer cannulated shaft 720 may have the slot. The projection 740 may move within the slot 750. Other methods of preventing rotation and/or keeping the shafts 710, 720 aligned are also envisioned. For example, the inner and outer shafts 710, 720 may have corresponding flat wall portions.

Additionally, the proximal end 724 of the outer cannulated shaft 720 may have at least one handle portion to enable an operator to move the outer cannulated shaft 720 along the inner cannulated shaft 710. In use, an operator can wrap his/her fingers around the handle portions. As shown in the embodiment of FIG. 7E, the shaft 720 may have a pair of diametrically opposed handles 738. The handle 738 may be integrally formed with the proximal end 724 or may be attached thereto, for example, by welding, gluing or by mechanical means (e.g., screws, bolts). Moreover, similar to the inner cannulated shaft 710, the outer cannulated shaft 720 may have a channel or slot 727, which may pass through its distal end 726. The channel or slot 727 may be aligned with the channel or slot 722 of the inner cannulated shaft 710 such that at least a portion of a fixation rod may be inserted therethrough. The channel or slot 727 may have a width, for example, between about 3 mm and about 10 mm and, more preferably between about 5 mm and about 8 mm. The channel or slot 727 may also have a height, for example, between about 3 mm and about 10 mm and, more preferably, between about 5 mm and about 8 mm. It should be noted that the channel or slot 727 dimension may also be applicable to the channel or slot 827 of FIG. 8E discussed below.

Figure 7F:
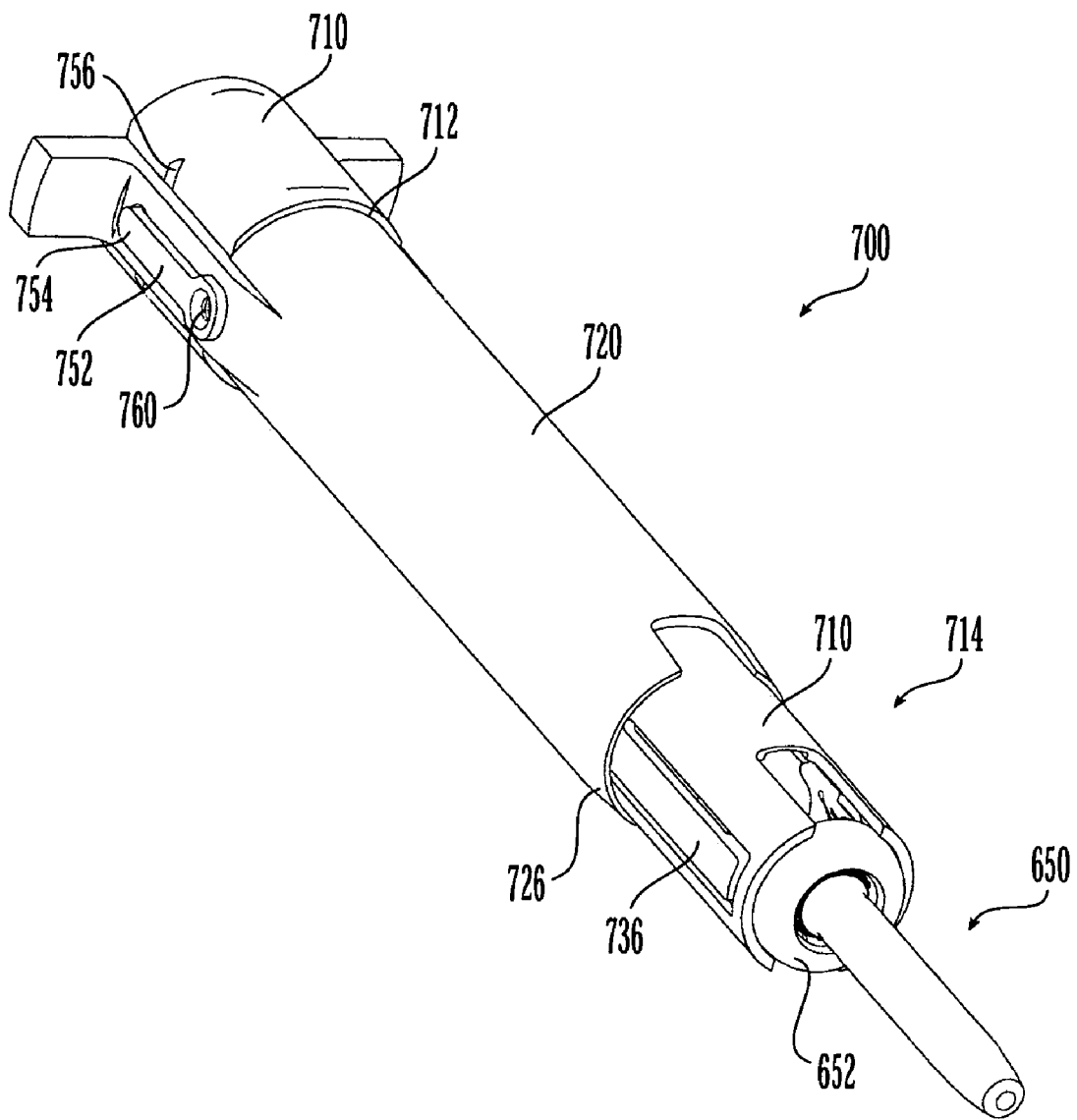
FIG. 7F is a perspective view of the insertion cannula of FIG. 7A in a first position engaging the screw of FIG. 6A.
Figure 7G:
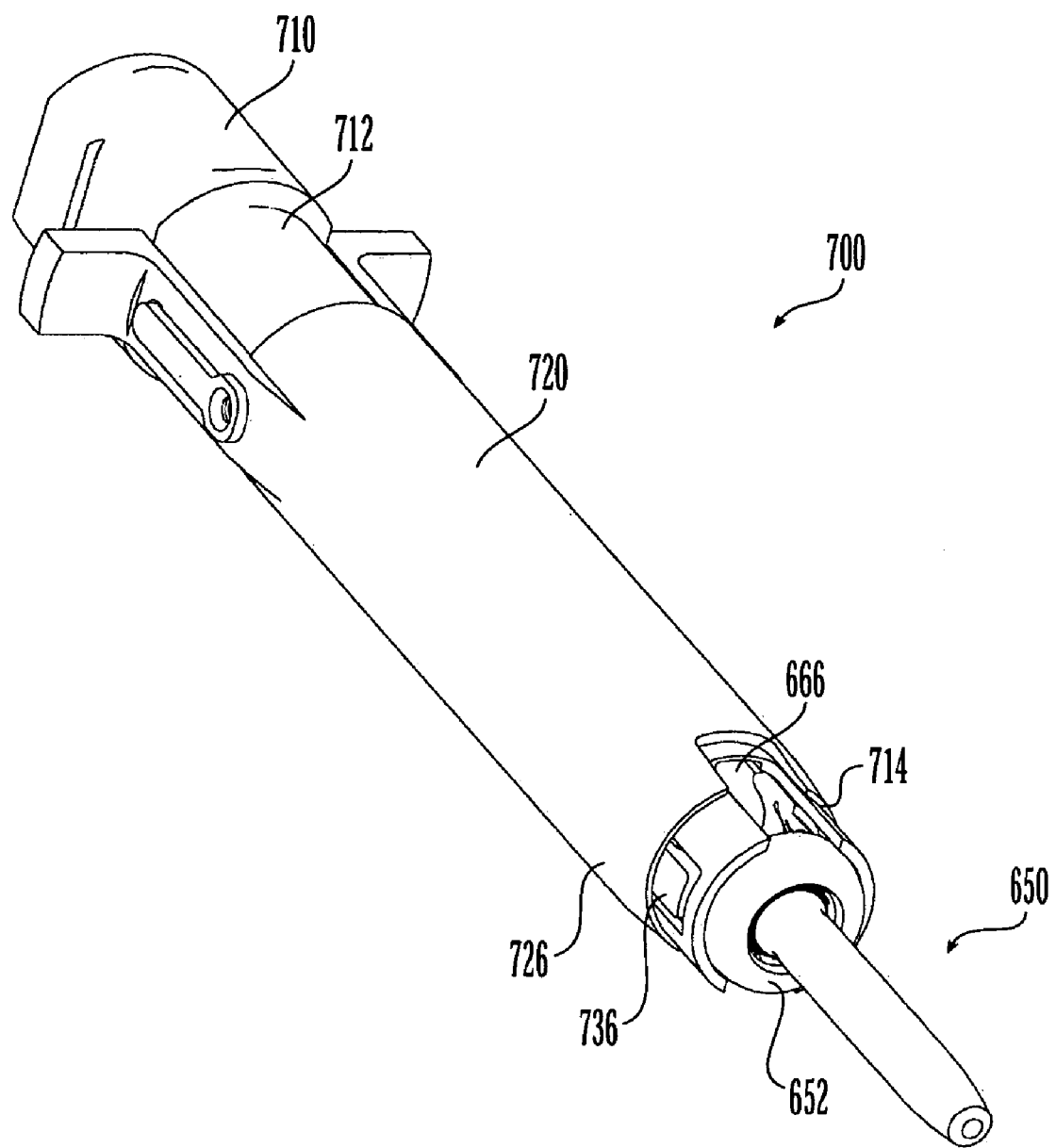
FIG. 7G is a perspective view of the insertion cannula of FIG. 7A in a second position engaging the screw of FIG. 6A.

FIGS. 7F and 7G illustrate the positioning of a bone screw 650 in the insertion cannula 700. The bone screw 650 may be positioned in the bore 716 at the distal end 714 of the inner cannulated shaft 710, and the screw 650 and cannula 700 may be inserted into the patient as a single unit. In another procedure where the cannula 700 has already been positioned in a patient, the screw 650 may be subsequently inserted down the bore 716 from the proximal end 712 to the distal end 714. To fix the bone screw 650 and, in particular, the head portion 652 with respect to the cannula 700, the outer cannulated shaft 720 may be moved from a first position (FIG. 7F), where the distal end 726 of the outer cannulated shaft 720 may be positioned closer to proximal end 712 of the inner cannulated shaft 710, to a second position (FIG. 7G), where the distal end 726 of the outer cannulated shaft 720 may be positioned closer to the distal end 714 of the inner cannulated shaft 710. Prior to fixing the screw 650 with respect to the insertion cannula 700, an operator may align the channels or slots 722, 727 with the channel 666 of head portion 652 of the bone screw 650.

The outer cannulated shaft 720 may be provided with a spring detent 752 (FIG. 7F), which may flex and which may engage a groove 756 in the first position and a groove 758 (FIG. 7B) in the second position. In particular, a protrusion (not shown) of spring detent 752 may pass through opening 758 (FIG. 7E) of handle 738 to engage grooves 756, 758. Such a construction may provide a tactile and/or audible indication to an operator that the outer cannulated shaft 720 is in the first or second position relative to the inner cannulated shaft 710. In one embodiment, the engagement of the protrusion of the spring detent 752 to the grooves 756, 758 may lock the outer cannulated shaft 720 in the first and/or second position on the inner cannulated shaft 710.

Figure 7H:
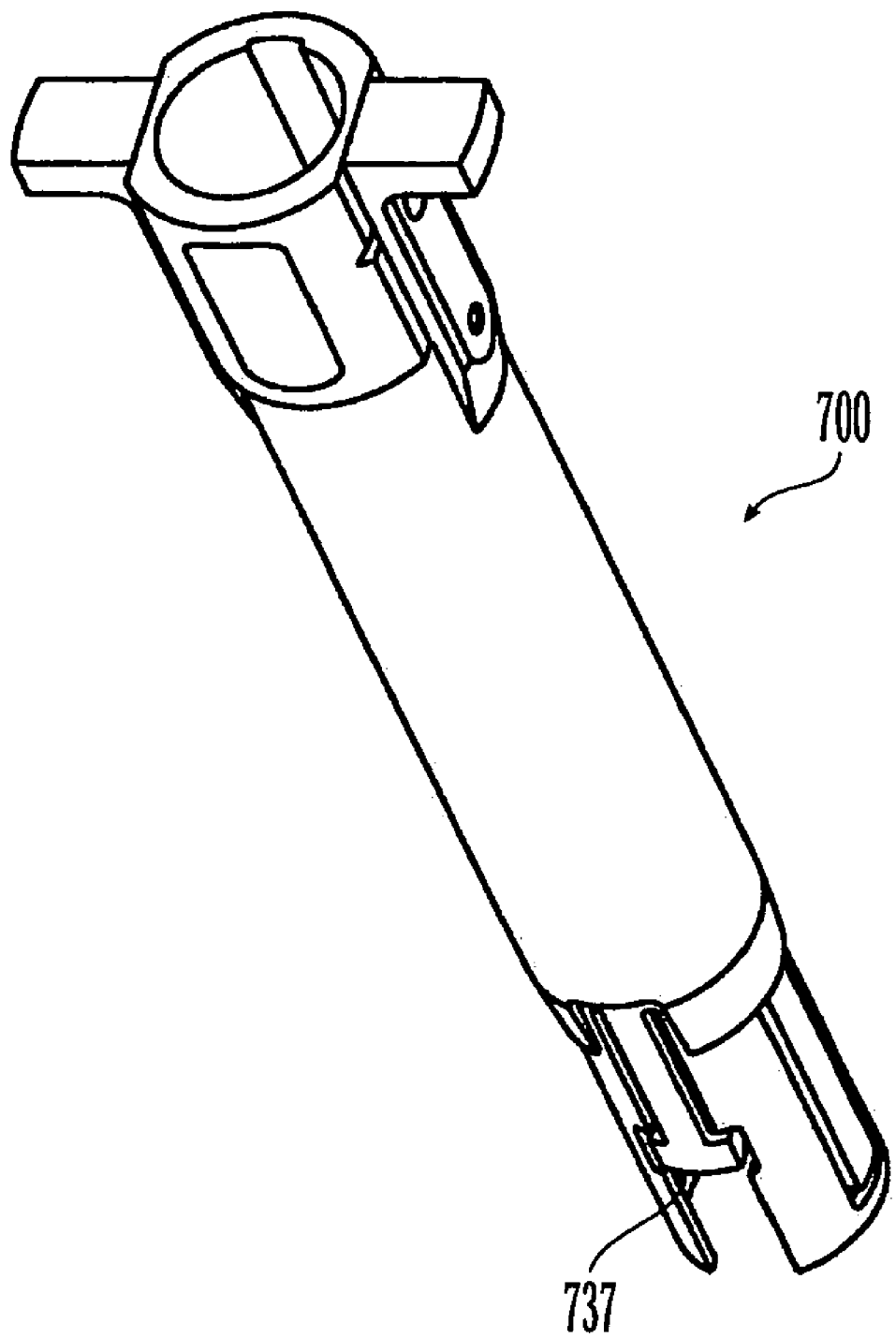
FIG. 7H is another perspective view of the insertion cannula of FIG. 7A.

In the second position shown in FIG. 7G, the distal end 726 of the outer cannulated shaft 720 may push against one or more flexible members 736. This, in turn, may result in the flexible member 736 engaging the recesses 670 of the head portion 652 of the bone screw 650. Such an engagement may prevent axial movement of the screw 650 relative to the insertion cannula 700. The outer cannulated shaft 720 may also push against an arm 737 (FIGS. 7A and 7H). The arm 737 may engage the head portion 652 of the screw 650 and, in particular, the arm 737 may fit inside the channel 666 of the head portion 652. In such a position, the arm 737 may prevent rotational movement of the head portion 652 of the screw 650 with respect to the cannula 700. Thus, the head portion 652 of the bone screw 650 may be fixed axially and rotationally with respect to the cannula 700, while still permitting the head portion 652 to pivot around the shank portion 654. It should be noted that, in some embodiments, the flexible member(s) 736 and/or arm 737 may fix axial and/or rotational movement of the screw 650 with respect to the cannula 700 prior to moving the outer cannulated shaft 720 to the second position. The cannula 700 may be used by an operator to manipulate the head portion 652 of one bone screw 650 so that the channel 666 may be aligned with the channel 666 of another bone screw 650. Once the channels 666 are aligned, an implant (e.g., fixation rod) may be inserted through the channels 666.

Additionally, in order to help an operator align the head portion 652, the inner cannulated shaft 710 may be provide with a flat surface 713, or mark or score (not shown). The flat surface 713 may be positioned outside of the body during a procedure and may provide a visual indicator to an operator of the orientation of the channels or slots 722, 727 and/or channel 666, which may be positioned within the body. The flat surface 713 may also help an operator align the channels or slots 722, 727 with channel 666 within the body.

Figure 8A:
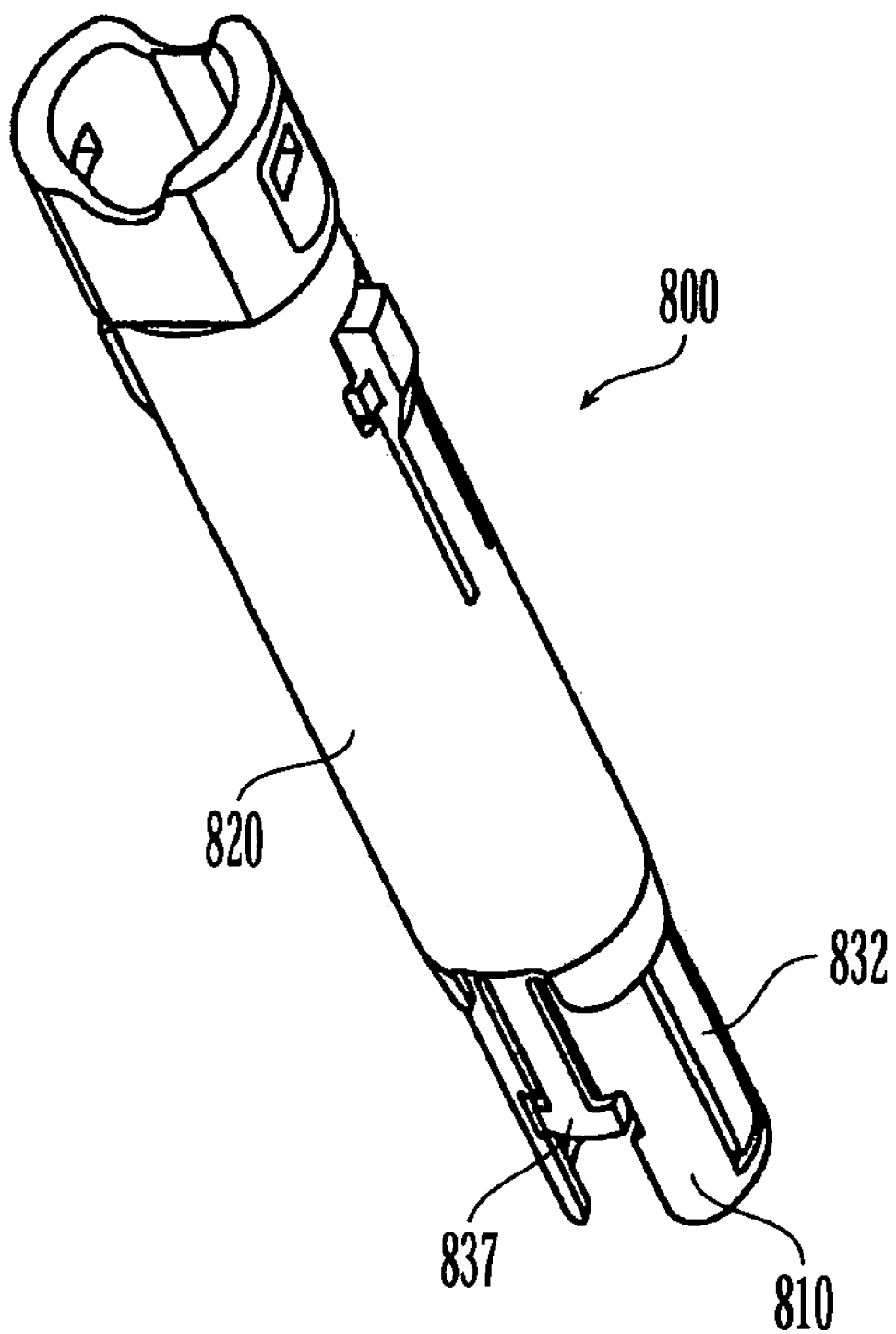
FIG. 8A is a perspective view of another exemplary embodiment of an insertion cannula.
Figure 8B:
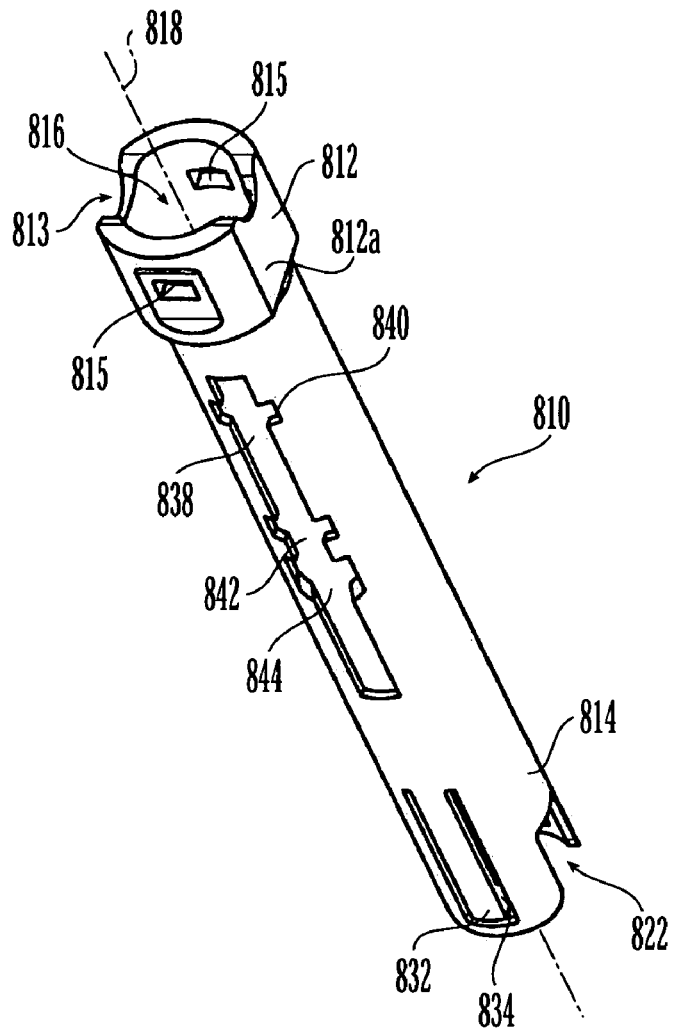
FIG. 8B is a perspective view of an exemplary embodiment of an inner portion of the insertion cannula of FIG. 8A.
Figure 8C:
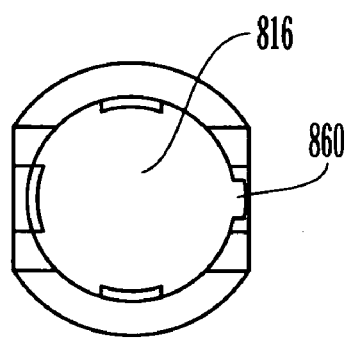
FIG. 8C is a top view of the inner portion of FIG. 8B.

FIG. 8A shows another embodiment of an insertion cannula—cannula 800. Similar to cannula 700, the insertion cannula 800 may comprise an inner cannulated shaft 810 received within an outer cannulated shaft 820. As shown in FIGS. 8B and 8C, the inner cannulated shaft 810 may have a proximal end 812, a distal end 814 and a bore 816 extending from the proximal end 812 to the distal end 814. The bore 816 may define a central axis 818 and may be dimensioned and configured for receiving a spinal implant (e.g., bone screw) or surgical instruments. A channel or slot 822 may be located at the distal end 814 of the inner cannulated shaft 810 and may extend at an angle (e.g., perpendicular) to the central axis 818. The channel or slot 822 may be U-shaped (although other shapes are contemplated) and may accommodate at least a portion of a fixation rod.

The proximal end 812 of the inner cannulated shaft 810 may have one or more holes 815. The holes 815 may be used to connect a mechanism (not shown) between adjacent cannulas 800 such that the cannulas may be in a fixed position relative to one another or may pivot relative to each other. In one embodiment, the holes 815 may be used to attach a guidance mechanism for guiding a fixation rod into the body. When the attached cannulas are manipulated, the cannulas 800 may impart a compressive or distraction force on the vertebrae. The proximal end 812 may be configured to cradle or secure a light source, which may be used to illuminate a surgical site through the bore 816. The proximal end 812 may also be configured to engage other devices.

Figures 8D, 8E:
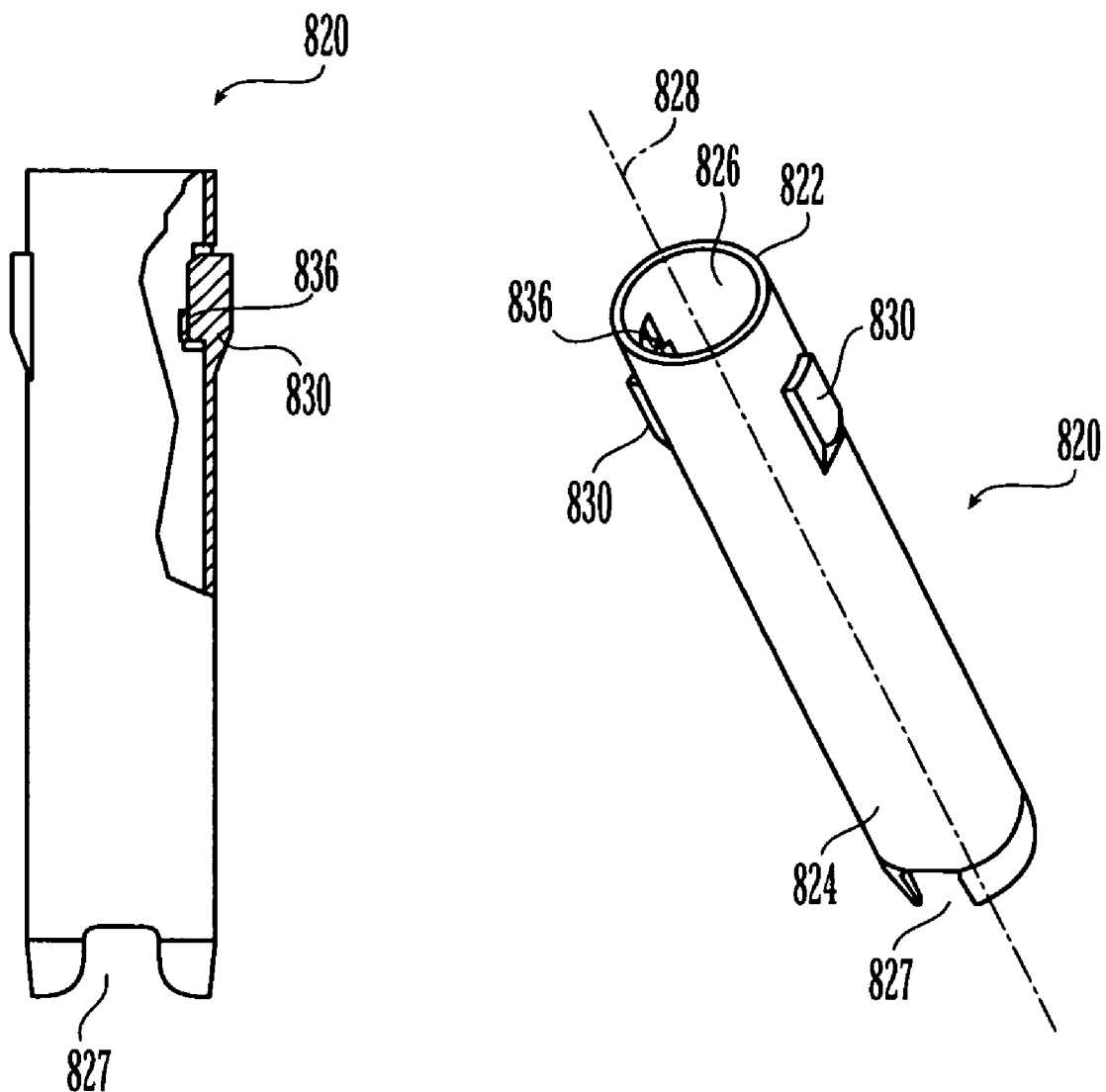
FIG. 8D is a partial cross-sectional view of an exemplary embodiment of an outer portion of the insertion cannula of FIG. 8A.
FIG. 8E is a perspective view of the outer portion of FIG. 8D.

FIGS. 8D and 8E illustrate an embodiment of the outer cannulated shaft 820. The outer cannulated shaft 820 may have a proximal end 822, a distal end 824 and a bore 826 extending from the proximal end 822 to the distal end 824. The bore 826 may define a central axis 828 and may be dimensioned and configured to receive the inner cannulated shaft 810. The outer cannulated shaft 820 may be shorter in length than the inner cannulated shaft 810 so as to permit the full length of the outer cannulated shaft 820 to slide along the exterior of the inner cannulated shaft 810 for reasons that will be detailed below. The distal end 824 of the outer cannulated shaft 820 may taper inwardly for close engagement with the distal end 814 of the inner cannulated shaft 810.

The outer cannulated shaft 820 may also be provided with at least one engaging portion 830. The engaging portion 830 may have at least one protrusion 836 (i.e., within the bore 816) for engaging a slot 838 in the wall of the inner cannulated shaft 810. In one embodiment having two engaging portions 830, such as FIG. 8E, one portion 830 may be flexible and the other portion 830 may be fixed with respect to the outer cannulated shaft 820. The engaging portion 830 may be flexible so that protrusion 836 may releasably snap into and out of the notches 840, 842, 844. Such a construction may prevent rotation of the outer cannulated shaft 820 with respect to the inner cannulated shaft 810 and/or keep the inner and outer shafts 810, 820 in a particular orientation (e.g., keep channels or slots 822 and 827 in alignment). As with cannula 700, others means of aligning the shafts 810, 820 are also envisioned. And, since the slot 838 may have one or more notches 840, 842, 844 for receiving the protrusion 836, such a construction may also allow the outer cannulated shaft 820 to be fixed with respect to the inner cannulated shaft 810 at set intervals.

The bone screw 650 may be positioned in the bore 816 at the distal end 814 of the inner cannulated shaft 810, and the screw 650 and cannula 800 may be inserted into the patient as a single unit. In another procedure where the cannula 800 has already been positioned in a patient, the screw 650 may be subsequently inserted down the bore 816 from the proximal end 812 to the distal end 814.

The bone screw 650 may be attached to the cannula 800 similar to the way it is attached to cannula 700 above. The outer cannulated shaft 820 may be moved from a first position, where the protrusion 836 of the engaging portion 830 engages the notch 840, to a second position, where the protrusion 836 of the engaging portion 830 engages the notch 842 or 844. Prior to moving the outer cannulated shaft 820 to the second position, an operator may align the channels or slots 822, 827 with the channel 666 of head portion 652 of the bone screw 650.

In the second position (not shown), the distal end 824 of the outer cannulated shaft 820 may push against at least one flexible member 832. However, it should be noted that multiple flexible members may be used. This, in turn, may result in the flexible member 832 and, consequently, the protrusion 834 engaging the recesses 670 of the head portion 652 of the bone screw 650. The flexible member 832 may prevent axial movement of the screw 650 with respect to the insertion cannula 800. Additionally, the outer cannulated shaft 820 may push against an arm 837 (FIG. 8A). The arm 837 may engage the head portion 652 of the screw 650 and, in particular, the arm 837 may fit inside the channel 666 of the head portion 652. In such a position, the arm 837 may prevent rotational movement of the head portion 652 of the screw 650 with respect to the cannula 800. Thus, the head portion 652 of the bone screw 650 may be fixed axially and rotationally with respect to the cannula 800. At the same time, the head portion 652 may be able to pivot about the proximal end 658 of the shank portion 654. It should be noted that, in some embodiments, the flexible member(s) 832 and/or arm 837 may fix axial and/or rotational movement of the screw 650 with respect to the cannula 800 prior to moving the outer cannulated shaft 820 to the second position.

The insertion cannula 800 may be used by an operator to manipulate the head portion 652 of one bone screw 650 so that the channel 666 may be aligned with a channel 666 of another bone screw 650 and that an implant (e.g., fixation rod) may be inserted through the channels 666. The inner cannulated shaft 810 may have a channel 813, which may be oriented in the same direction as the channels or slots 822 and/or 827. Moreover, the inner cannulated shaft 810 may be provided with flattened surface 812a, which may be located on the side of the inner cannulated shaft 810 that the channel or slot 822 passes through. The channel 813 and/or flattened surface 812a may be positioned outside the body during a procedure and may provide the operator of a visual indicator of the orientation of the channels or slots 822, 827 and/or channel 666 inside the body. Such a construction may also help an operator align the channels or slots 822, 827 with channel 666 in the body.

Figures 9A, 9D:
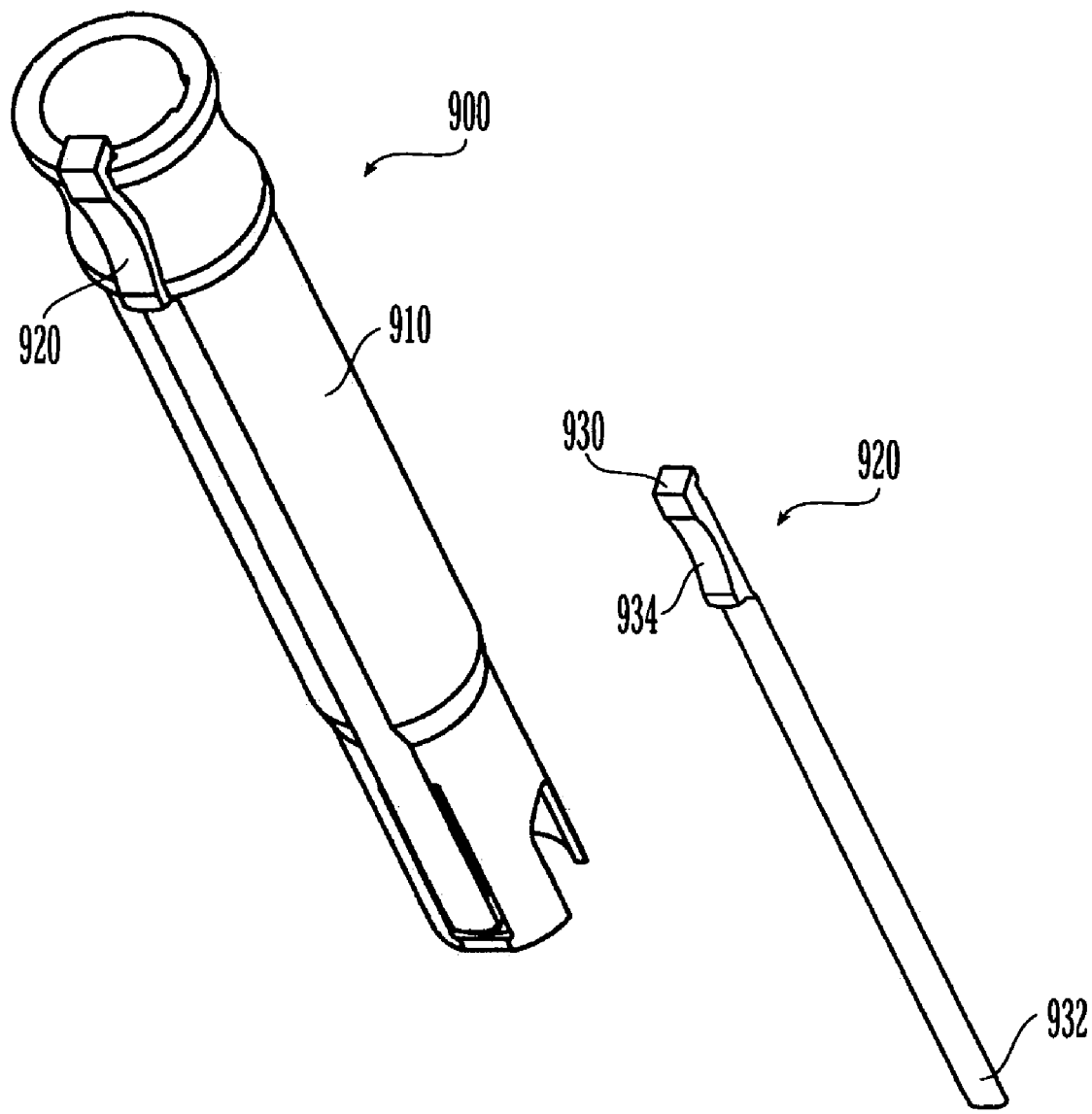
FIG. 9A is a perspective view of another exemplary embodiment of an insertion cannula.
FIG. 9D is a perspective view of an exemplary embodiment an elongated piece for insertion in the portion of FIG. 9B.

FIG. 9A illustrates yet another embodiment of an insertion cannula—cannula 900. The system 900 may comprise a cannulated shaft 910 and an elongated piece 920. Shown in FIGS. 9B and 9C, the cannulated shaft 910 may have a proximal end 912, a distal end 914, and a bore 916 with an axis 918 extending from the proximal end 912 to the distal end 914. A channel or slot 928 may pass through the distal end 914 of the cannulated shaft 910 such that at least a portion of a fixation rod may pass therethrough. The cannulated shaft 910 may also have a recess 922, which may extend between the proximal end 912 and the distal end 914 and which may hold an elongated piece 920 (FIG. 9D) therein. The shape of the recess 922 as shown in FIG. 9C may be designed to receive a corresponding shape of the elongated piece 920 such that the elongated piece 920 may move up and down in the recess 922, but may not be pulled out of the recess in a direction transverse to the axis 918. Moreover, the recess 922 may have a slot 924 for engaging a protrusion (not shown) of the elongated piece 920. This construction may prevent the elongated piece 920 from separating or twisting relative to the cannulated shaft 910 and may guide the movement of the elongated piece 920 within the recess 922.

The cannulated shaft 910 may have an inner diameter, for example, between about 3 mm and about 20 mm and, more preferably, between about 12 mm and about 15 mm. However, the inner diameter may be any size so long as a screw 650 and/or tools may be positioned therethrough. The shaft 910 may have an outer diameter, for example, between about 3 mm and about 20 mm and, more preferably, between about 15 mm and about 18 mm. Moreover, the cannulated shaft 910 may have a length, for example, between about 40 mm and about 160 mm and, more preferably, between about 110 mm and about 130 mm. The channel or slot 928 may have a width, for example, between about 3 mm and about 10 mm and, more preferably between about 5 mm and about 8 mm. The channel or slot 928 may also have a height, for example, between about 3 mm and about 20 mm and, more preferably, between about 12 mm and about 16 mm.

The elongated piece 920, as shown in FIG. 9D, may comprise a proximal end 930 and a distal end 932. The elongated piece 920 may have a length, for example, between about 20 mm and about 140 mm and, more preferably, between about 110 mm and about 130 mm. Moreover, the elongated piece 920 may have a enlarged portion 934, which may provide an operator with a portion to actuate the elongated piece 920. The enlarged portion 934 may have a surface treatment, such as a knurling, for enhancing an operator's grasp on the piece 920.

The bone screw 650 may be positioned in the bore 916 at the distal end 914 of the cannulated shaft 910, and the screw 650 and cannula 900 may be inserted into the patient as a single unit. In another procedure where the cannula 900 has already been positioned in a patient, the screw 650 may be subsequently inserted down the bore 916 from the proximal end 912 to the distal end 914. An operator may orient the channel or slot 928 with the channel 666 of head portion 652 of the bone screw 650. To fix the bone screw 650 with respect to the cannula 900, the distal end 932 of the elongated piece 920 may engage a flexible member 927. In such a position, the elongated piece 920 may push the flexible member 927 towards the head portion 652 of the bone screw 650 so that the flexible member 927 engages the recesses 670 of the head portion 652. Thus, the head portion 652 of the bone screw 650 may be fixed with respect to the cannula 900. It should be noted that in some embodiments, the flexible member 927 may fix axial movement of the screw 650 with respect to the cannula 900 prior to the elongated piece 920 engaging the member 927. The head portion 652 may pivot with respect to the proximal end 658 of the shank portion 654. This may enable an operator to manipulate the head portion 652 in preparation for insertion of a fixation rod.

Figure 10A:
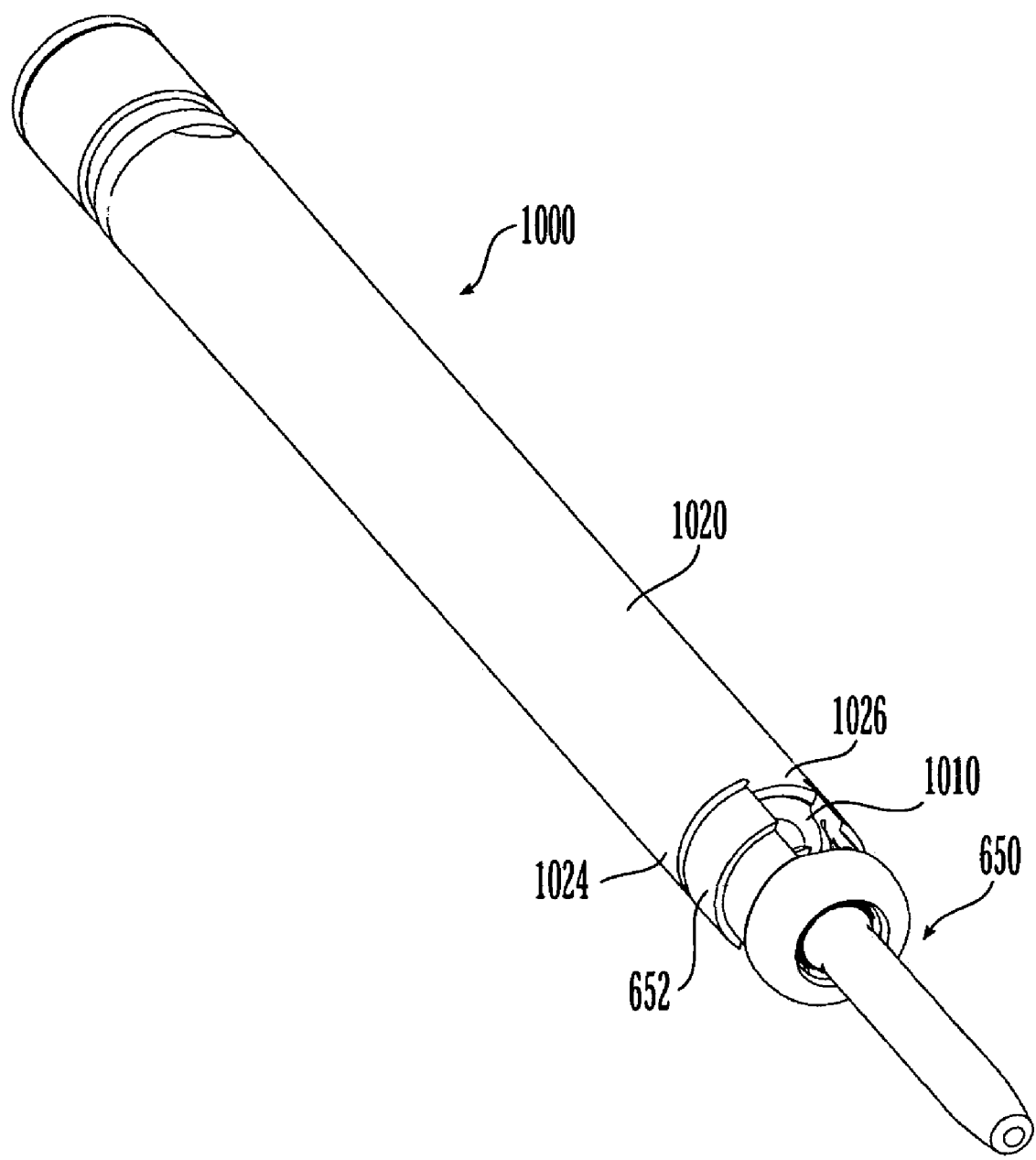
FIG. 10A is a perspective view of another exemplary embodiment of an insertion cannula.
Figure 10B:
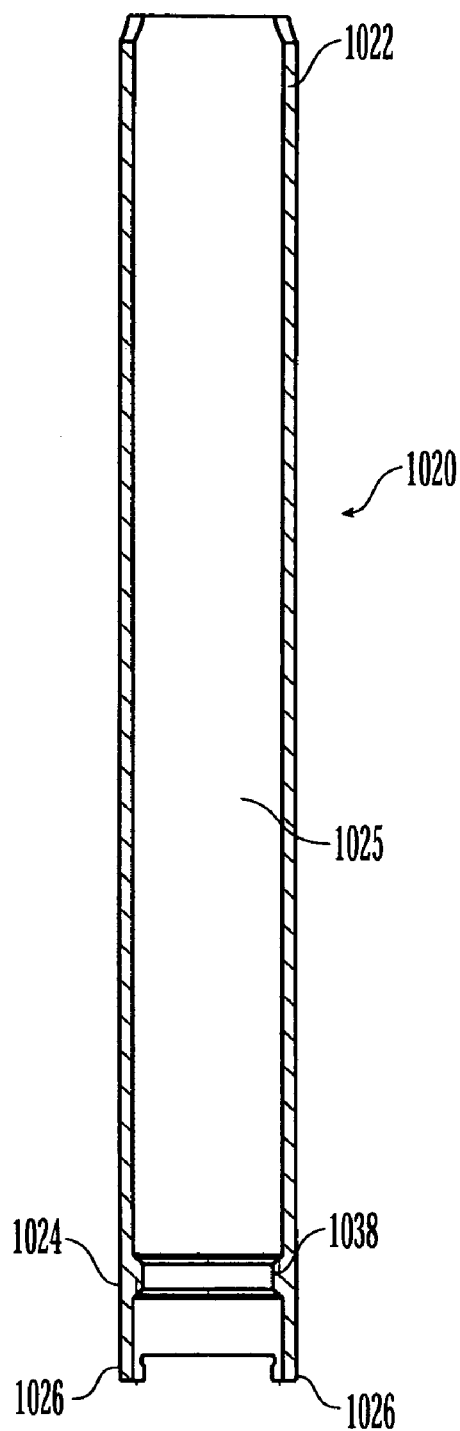
FIG. 10B is a cross-sectional view of an exemplary embodiment of an outer portion of the insertion cannula of FIG. 10A.
Figure 10C:
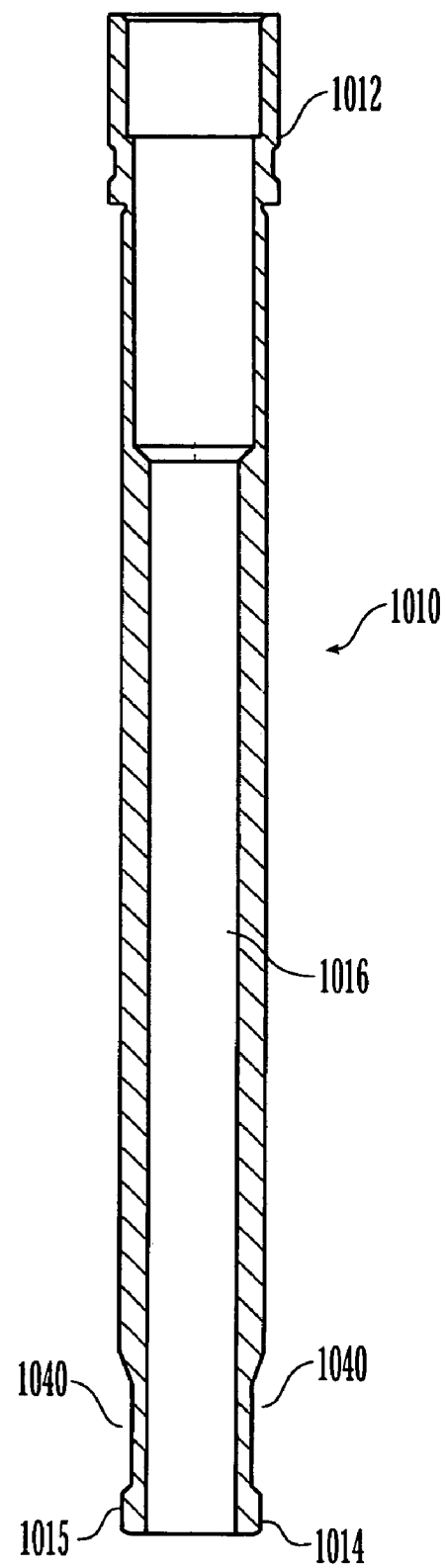
FIG. 10C is a cross-sectional view of an exemplary embodiment of an inner portion of the insertion cannula of FIG. 10A.

FIG. 10A illustrates a cannula 1000 which, similar to the cannulas described above, may be used to hold a screw 650. As shown in FIGS. 10A-10D, the cannula 1000 may comprise an inner cannulated shaft 1010 and an outer cannulated shaft 1020. The inner cannulated shaft 1010 may have a proximal end 1012, a distal end 1014 and a bore 1016 extending from the proximal end 1012 to the distal end 1014. The distal end 1014 of inner cannulated shaft 1010 may have an external threaded portion 1015 for engaging the internal threads 672 of the head portion 652 of the screw 650. The proximal end 1012 may have a surface treatment, for example knurling, to facilitate gripping of the cannula 1000. Additionally, the proximal end 1022 may have a flattened portion, score or marking (not shown), which may indicate the orientation of channel 666 of the bone screw 650.

The inner cannulated shaft 1010 may have an inner diameter, for example, between about 3 mm and about 20 mm and, more preferably, between about 7 mm and about 11 mm. The inner shaft 1010 may have an outer diameter, for example, between about 3 mm and about 20 mm and, more preferably, between about 10 mm and about 12 mm. Moreover, the inner cannulated shaft 1010 may have a length, for example, between about 40 mm and about 160 mm and, more preferably, between about 110 mm and about 130 mm.

Figure 10D:
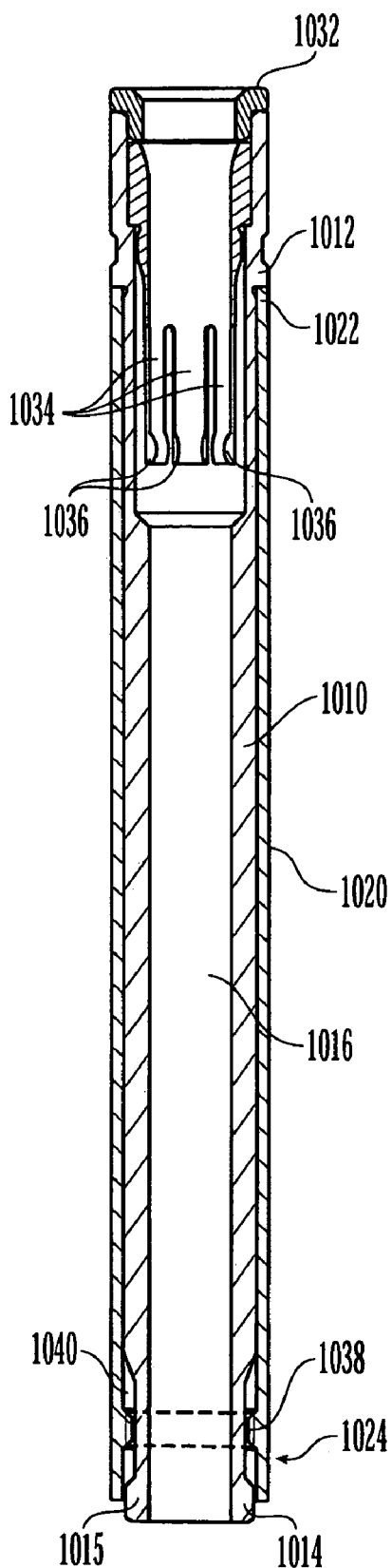
FIG. 10D is a cross-sectional view of the insertion cannula of FIG. 10A.

As shown in FIG. 10D, an insert 1032 may be positioned within the inner cannulated shaft 1010. The insert 1032 may comprise fingers 1034 for engaging a surgical instrument (e.g., screwdriver) inserted within the bore 1016 of the inner cannulated shaft 1010. As such, a surgical instrument may be snap-fit into the proximal end 1012 of the inner cannulated shaft 1010 while, at the same time, being able to rotated therein. The insert 1032 may also have protrusion 1036 for engaging a portion of a surgical instrument.

The outer cannulated shaft 1020 may be positioned over the inner cannulated shaft 1010 and may be moveable thereon. The outer cannulated shaft 1020 may have a proximal end 1022, a distal end 1024 and a channel 1025 therethrough extending from the proximal end 1022 to the distal end 1024. The outer cannulated shaft 1020 may have one or more protrusions 1038 for engaging one or more recesses 1040 of the inner cannulated shaft 1010. In one embodiment, the protrusion 1038 may be an annular protrusion extending around the entire interior surface of the outer cannulated shaft 1020. Moreover, the recess 1040 may be an annular recess in the outer periphery of the inner cannulated shaft. Such a construction may allow the outer cannulated shaft 1020 to move axially with respect to the inner cannulated shaft 1010.

In addition, the outer diameter of the outer cannulated shaft 1020 may be equal to the outer diameter of the head portion 652 of the screw 650. In a construction where the diameter of the outer cannulated shaft 1020 may be the same as the diameter of the head portion 652, the distal portion 1024 of the outer cannulated shaft 1020 may rest against the chamfered edges 668 of the head portion 652 of the screw 650. In another embodiment, the outer cannulated shaft 1020 may have a diameter, which may be larger than the diameter of the head portion 652 of the screw 650.

The outer cannulated shaft 1020 may have an inner diameter, which may be larger than the outer diameter of the inner cannulated shaft 1010, and an outer diameter, for example, between about 3 mm and about 20 mm and, more preferably, between about 12 mm and about 15 mm. Moreover, the outer cannulated shaft 1020 may have a length, for example, between about 20 mm and about 140 mm and, more preferably, between about 100 mm and about 110 mm.

To fix the bone screw 650 with respect to the cannula 1000, the external thread portion 1015 of the inner cannulated shaft 1010 may engage the inner threaded portion 672 of the head portion 652 of the screw 650 (FIG. 6A). It should be noted, however, that any means of engaging the inner cannulated shaft 1010 to the bone screw 650 is also envisioned. The outer cannulated shaft 1020 may be in its rear position with the proximal end 1022 of the outer cannulated shaft 1020 engaging the proximal end 1012 of the inner cannulated shaft 1010, such as shown in FIG. 10D. Once the inner cannulated shaft 1010 has engaged the head portion 652, the outer cannulated 1020 shaft may be moved down the inner cannulated shaft 1010 such that the protrusion 1038 moves within the recess 1040. And, the distal end 1024 of the outer cannulated shaft 1020 engages the head portion 652 of the screw 650. In particular, as shown in FIG. 10A, the outer cannulated shaft 1020 may have extended portions 1026, which may be inserted into the space between the parallel arms 664 of the head portion 652 (i.e., into the top of the channel 666). The bone screw 650 may then be fixed axially and rotationally with respect to the cannula 1000.

b. Side and/or Top Insertion Cannula

Figure 11A:
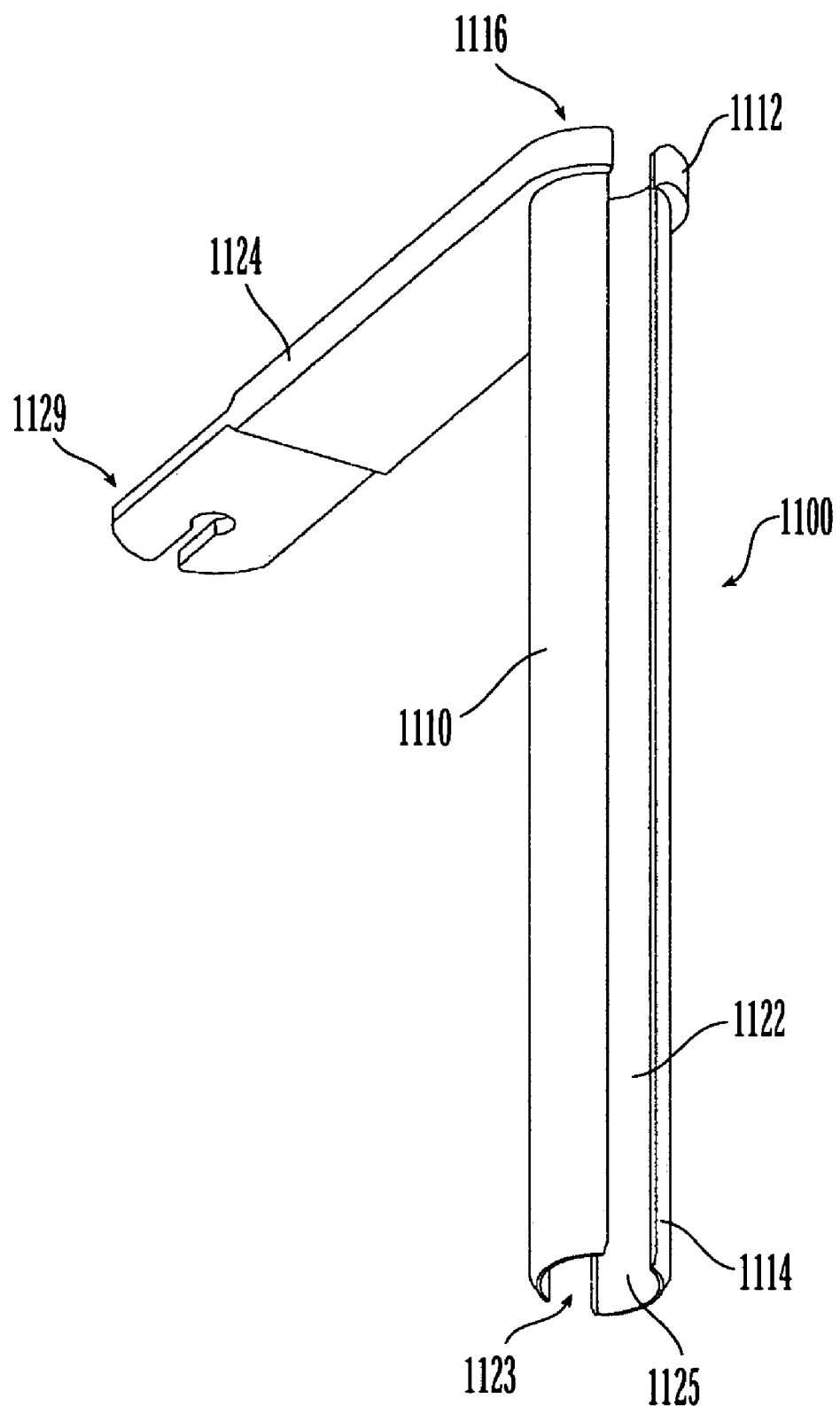
FIG. 11A is a perspective view of another exemplary embodiment of an insertion cannula.
Figure 11B:
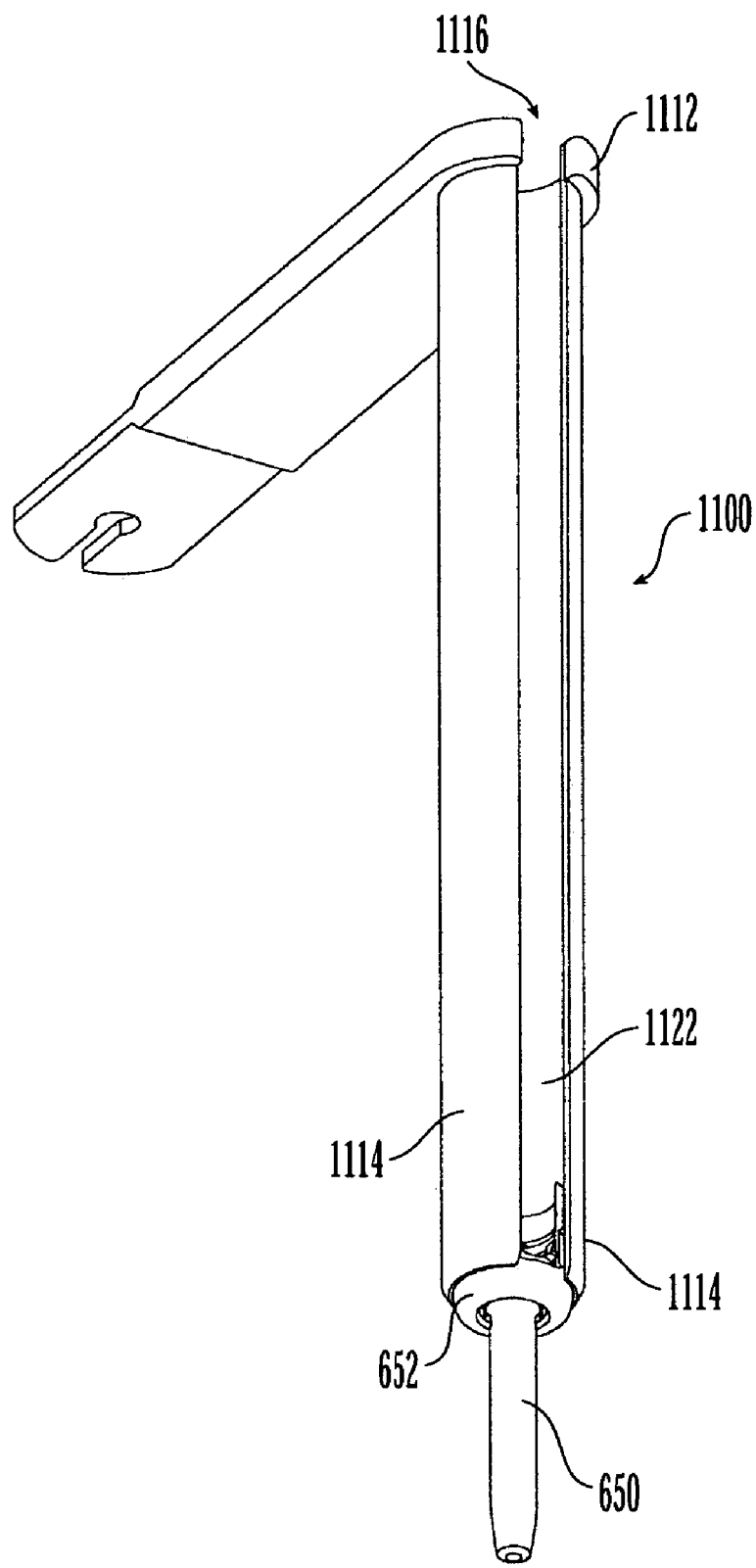
FIG. 11B is a perspective view of the insertion cannula of FIG. 11A engaging the screw of FIG. 6A.

FIGS. 11A and 11B illustrates an insertion cannula 1100, which may be used for inserting a rod from the top or side of a screw 650 (i.e., the screw 650 may be side or top loaded). The cannula 1100 may comprise an elongated member 1110 having a proximal end 1112, a distal end 1114 and a channel 1116 extending from the proximal end 1112 to the distal end 1114. Moreover, the cannula 1100 may have a first longitudinal slot 1122, which may intersect the channel 1116 and which may extend from the proximal end 1112 to the distal end 1114. The slot 1122, however, may cover any length of the elongated member 1110 and may end a distance from the proximal end 1112. In addition, the cannula 1100 may have a second longitudinal slot 1123, which may also intersect the channel 1116. The second slot 1123 may be shorter, longer or the same length as the first slot 1122. It should be appreciated that the second slot 1123 may be unnecessary. The slot(s) 1122, 1123 may enable a rod to be inserted down through the channel 1116 and into a screw 650.

The distal end 1114 of the insertion cannula 1100 may engage the head portion 652 of the screw 650 (FIG. 11B). For example, the distal end 1114 may have protrusions (not shown) on inner walls 1125 of the elongated member 1110 for engaging the recesses 670 of the head portion 652. Alternatively, the distal end 1114 may loosely engage the head portion 652. In general, the cannula 1100 may be used to manipulate the head portion 652 of the screw 650 so that a fixation device may be inserted and attached to the head portion 652. Furthermore, the proximal end 1112 may have a handle 1124 for handling and manipulating cannula 1100. And, the handle 1124 may have a attachment portion 1129 for attached the cannula 1100 to, for example, an operating table.

Figure 12A:
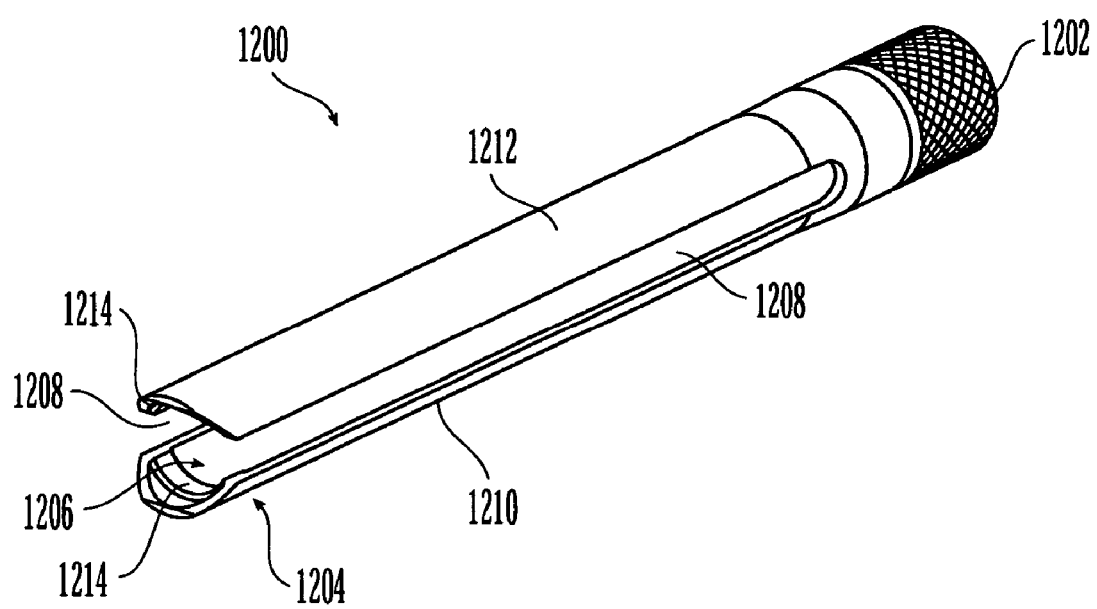
FIG. 12A is a perspective view of another exemplary embodiment of an insertion cannula.
Figure 12B:
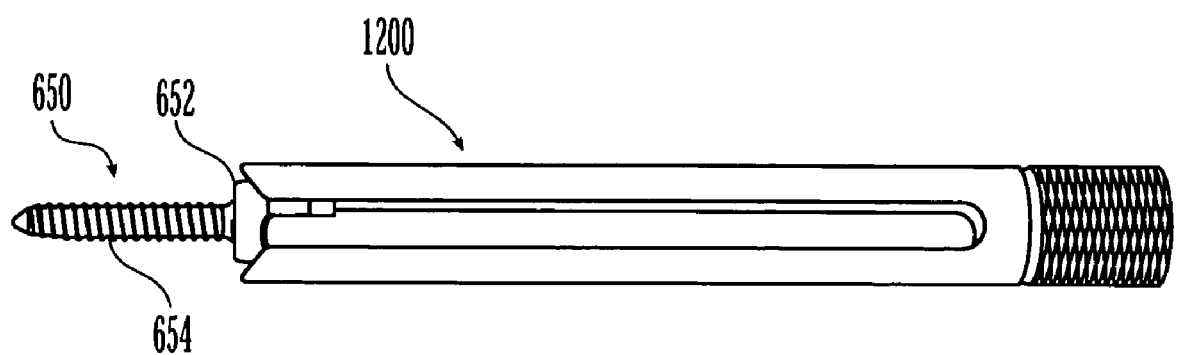
FIG. 12B is a side view of the insertion cannula of FIG. 12A engaging the screw of FIG. 6A.

FIG. 12A illustrates another embodiment of an insertion cannula, which may be used to insert a spinal rod from the top or side of a bone screw 650. The insertion cannula 1200 may comprise a proximal end 1202, a distal end 1204, and a channel 1206 extending through the cannula 1200 from the proximal end 1202 to the distal end 1204. Moreover, the cannula 1200 may comprise at least one slot 1208 intersecting the channel 1206. The slot(s) 1208 may enable a rod to be inserted down through the channel 1206 and into the screw 650. As shown in FIG. 12A, in an embodiment with more than one slot 1208, the slots 1208 may define two arms 1210 and 1212. Such a construction may results in the arm 1210 and 1212 being flexible such that a screw 650 and, specifically, the head portion 652 may be clipped/snapped between the arms 1210 and 1212 (FIG. 12B). Alternatively, the slots 1208 may enable a rod to be inserted from the side of a screw 650. The slots 1208 may extend from the distal end 1204 of the cannula 1200 to a position a distance away from the proximal end 1202. In an embodiment with more than one slot 1208, the slots 1208 may be the same length or different lengths.

Moreover, the proximal end 1202 may have a surface treatment, such as a knurling, or may have a grip to enhance an operator's grasp of the cannula 1200. In addition, the arms 1210 and/or 1212 may have protrusions 1214 for engaging the recess 670 of the head portion 652 of the screw 650. When the screw 650 is engaged by the cannula 1200 as shown in FIG. 12B, the screw 650 may be fixed such that the head portion 652 may move rotationally (i.e., may rotate within the cannula 1200), but not axially with respect to cannula 1200. In one embodiment, the screw 650 may be fixed with respect to insertion cannula 1200 so that rotational movement may also be prevented. The cannula 1200 may be used to pivot the head portion 652 relative to the shank portion 654.

The insertion cannula 1100, 1200 may have an inner diameter, for example, between about 3 mm and about 20 mm and, more preferably, between about 12 mm and about 16 mm. It should be noted that the inner diameter of cannulas 1100, 1200 may be any size so long as a screw 650 and/or tools may be positioned therethrough. The insertion cannula 1100, 1200 may have an outer diameter, for example, between about 3 mm and about 20 mm and, more preferably, between about 14 mm and about 17 mm. Moreover, the cannulas 1100, 1200 may have a length, for example, between about 40 mm and about 200 mm and, more preferably, between about 140 mm and about 160 mm. The slots 1208 may have a width, for example, between about 3 mm and about 10 mm and, more preferably between about 5 mm and about 8 mm. The slots 1208 may also have a height, for example, between about 30 mm and about 160 mm and, more preferably, between about 110 mm and about 130 mm.

3. Drill

A drill 1350 (FIG. 13A) may be used to create a cavity in the vertebrae into which a screw 650 may be inserted. The drill 1350 may be positioned into working cannula 475, retractor 500, and/or an insertion cannula and moved down towards a surgical site. For example, in a technique using a guide wire 150, such as shown in FIG. 13B, the drill 1350 may be cannulated and may be guided by the guide wire 150 down an insertion cannula. The drill 1350 may also be guided by a guidewire 150 down a working cannula 475 or retractor 500.

Figure 13A:
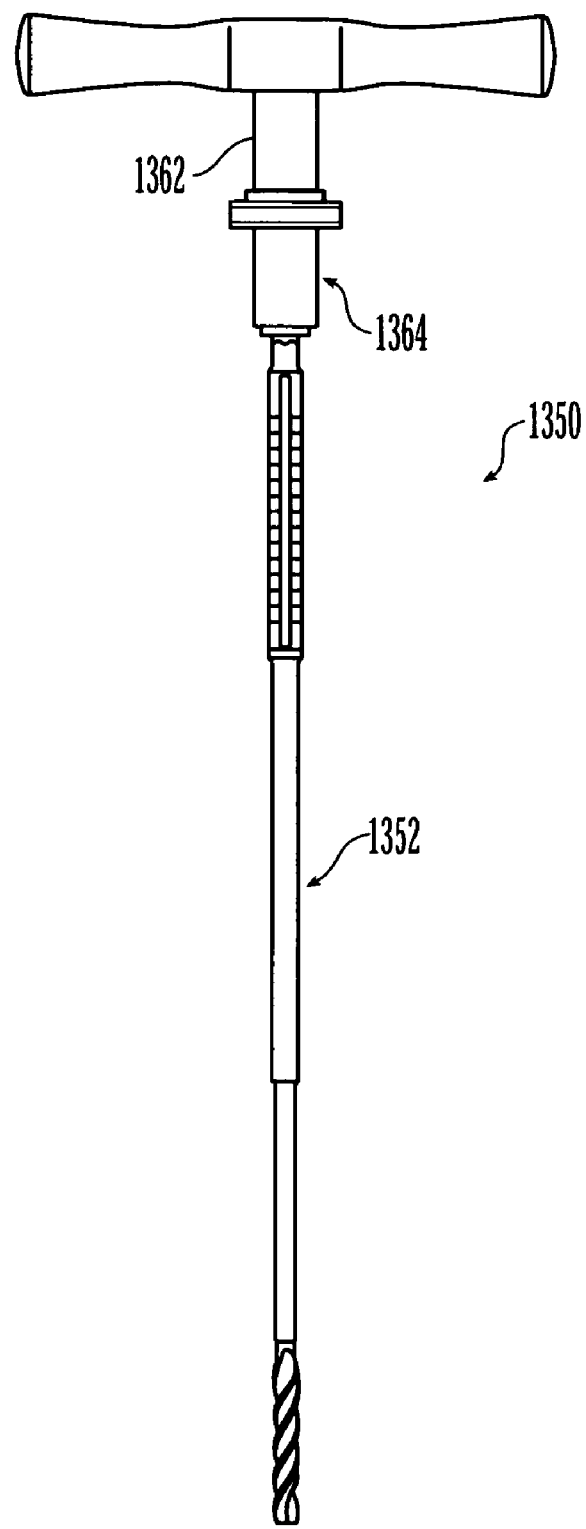
FIG. 13A is a side view of an exemplary embodiment of a drill.
Figure 13B:
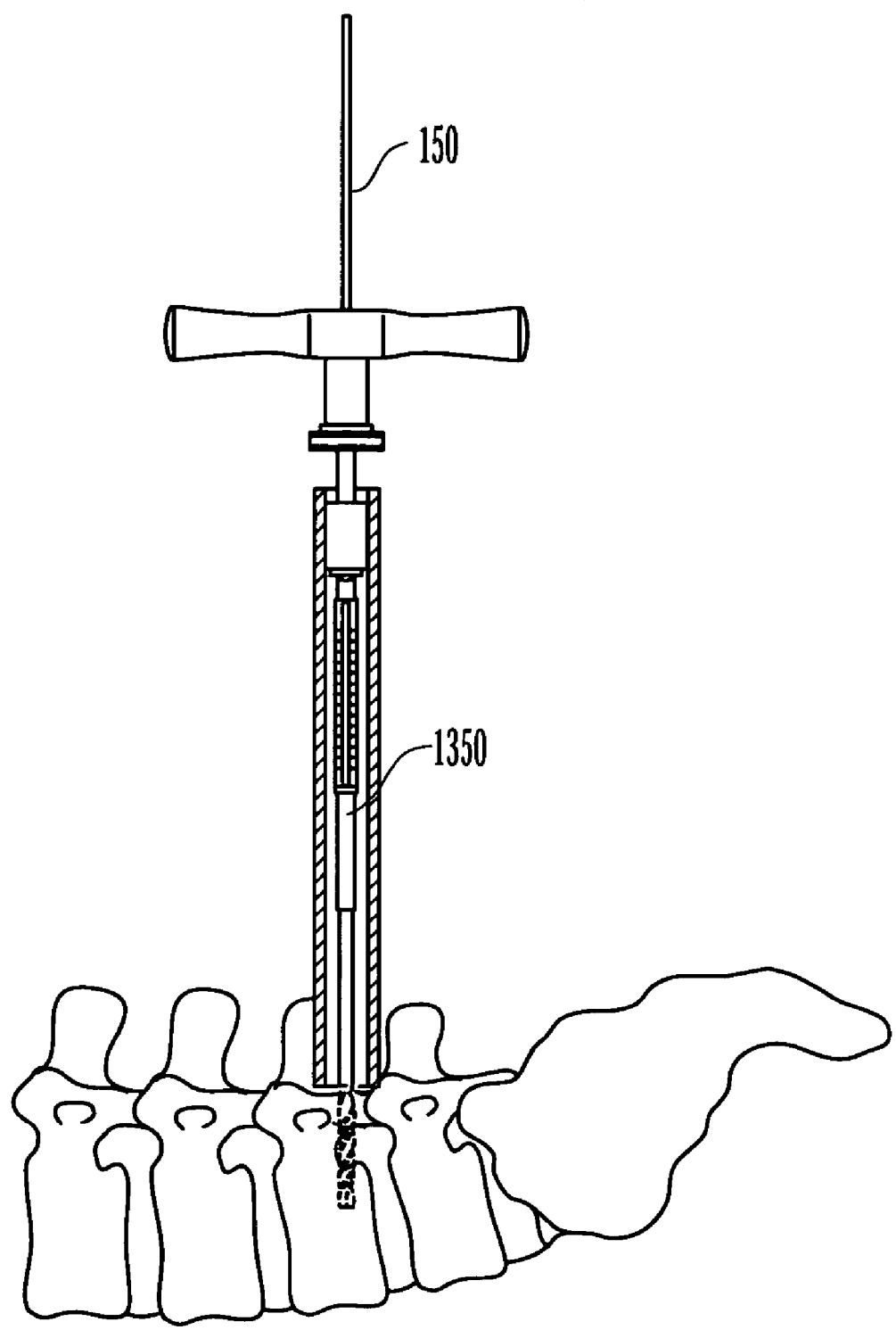
FIG. 13B is a side view of the drill of FIG. 13A being drilled into the spine through a cannula.

As illustrated in FIG. 13A, the drill 1350 may comprise a drill bit 1352 and a handle 1362. The drill bit 1352 and handle 1362 may be one integral piece or two pieces connected together. For example, the drill bit 1352 may be connected to the handle 1362 by a coupling 1364. The handle 1362 may be used to manually drill a hole in a vertebra. The handle 1362 may be T-shaped, spherical, elliptical or any other shape. It should, however, be noted that the drill 1350 may not have a handle 1362 but, instead, the drill bit 1352 may be attached to a power drill. Thus, the drill bit 1352 may be operated electrically or pneumatically.

Figures 13C, 13D:
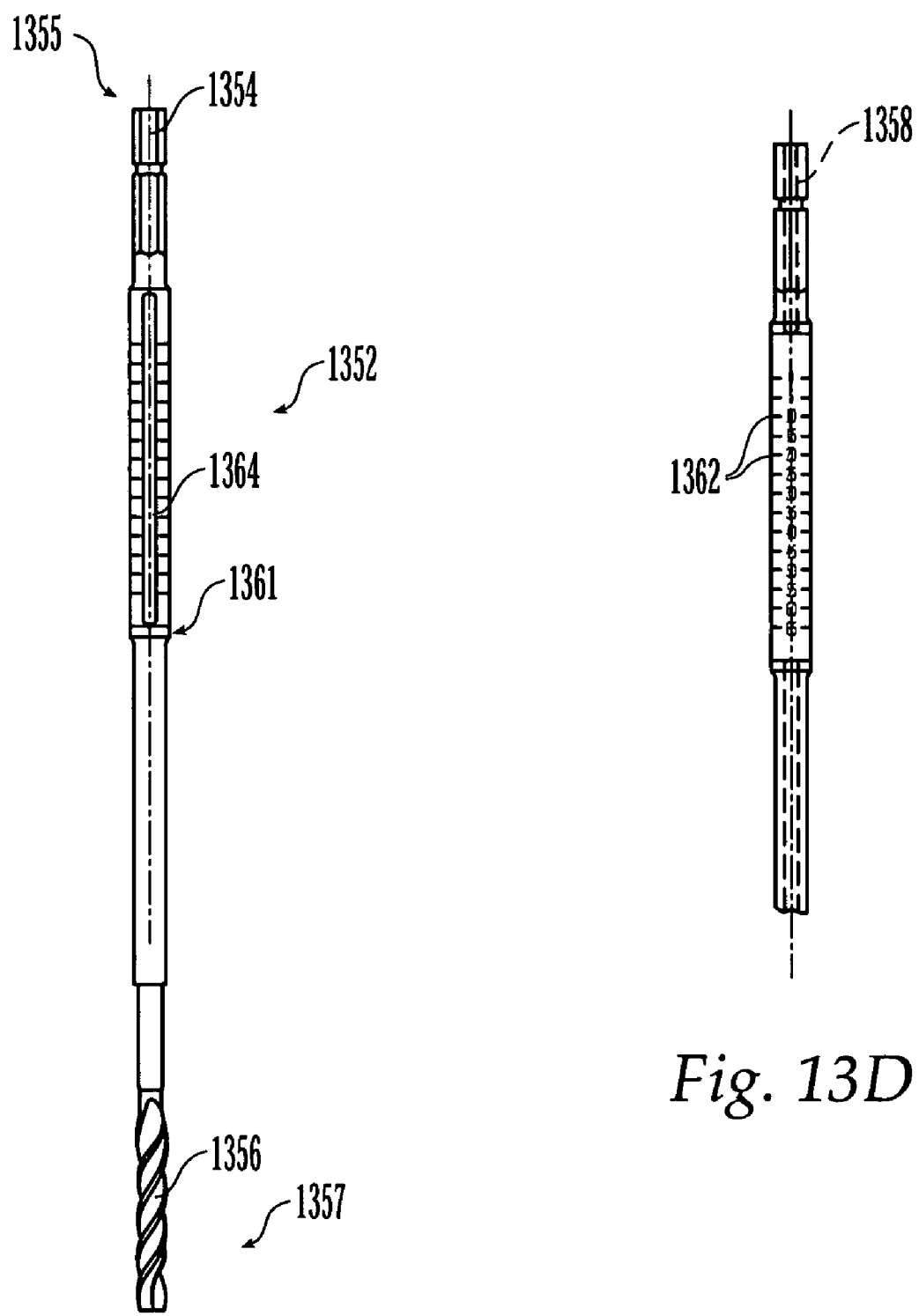
FIGS. 13C and 13D are side views of an exemplary embodiment of a drill bit of the drill of FIG. 13A.

As shown in FIGS. 13C and 13D, the drill bit 1352 may have a shaft 1361, a connecting portion 1354 on the proximal end 1355 of the shaft 1361 and a tip 1356 at the distal end 1357 of the shaft 1361. In addition, the drill bit 1352 may have a central bore 1358 for those procedures where an operator may desire to use a guide wire 150. The shaft 1361 may have a uniform diameter or may have a portion having a larger diameter. Further, the connecting portion 1354 may be attached to a handle such as described above or may be connected to a power drill. The tip 1356 of the drill bit 1352 may be configured similar to other bone cutting drill bits known by those of skill in the art.

Moreover, in one embodiment, a window 1364 may be located between the proximate end 1354 and the distal end 1356 and may permit an operator to see, for example, the guide wire 150 or bone tissue moving through the central bore 1358 of the drill bit 1352. In addition, the shaft 1361 may comprise markings 1362 spaced apart at set intervals. Such markings 1362 may enable an operator to monitor the depth of the drill bit 1352 into bone tissue.

In use, after the drill 1350 is inserted into a working cannula 475, retractor 500 and/or insertion cannula and positioned proximate a vertebra, the drill 1350 may be rotated manually by the handle 1362 or electrically/pneumatically by a power drill to form a cavity in which an implant, such as the screw 650, may be anchored.

It should, however, be understood by those skilled in the art that any means of creating a cavity in bone is envisioned. For example, an operator may use an awl, probe and/or tap instead of or in addition to the drill 1350 to create a cavity in the vertebrae. Moreover, in some embodiments, a screw 650 may be inserted directly into bone without first using a drill or other cavity creating tool to create a cavity.

4. Implant Positioner

Figure 14:
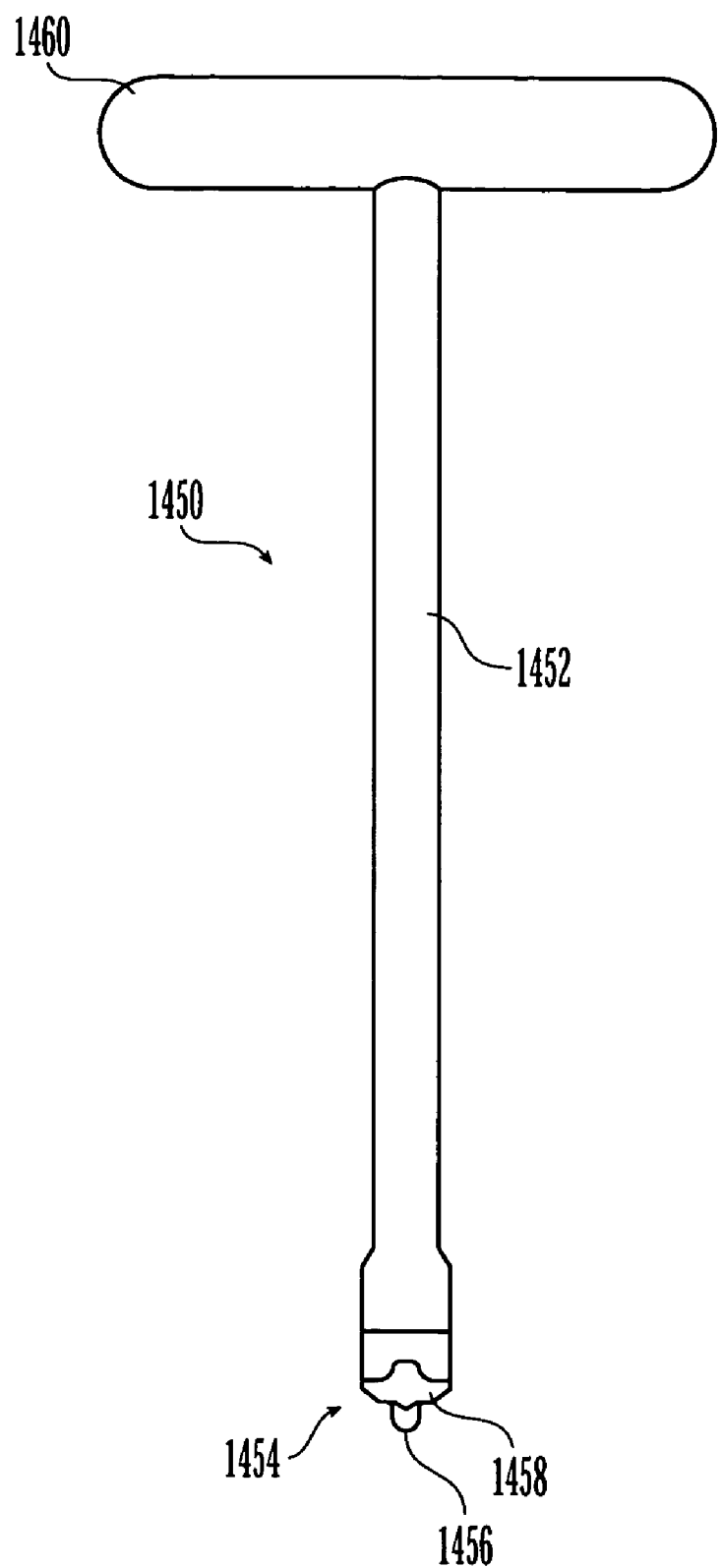
FIG. 14 is a side view of an exemplary embodiment of an implant positioner.

FIG. 14 illustrates a positioner 1450, which may be used to orient a bone screw 650 within a working cannula 475, a retractor 500 and/or an insertion cannula. The positioner 1450 may comprise a shaft 1452 and a forward portion 1454 operatively connected to the shaft 1452. The forward portion 1454 may be configured to engage the head portion 652 of the screw 650 and/or the proximal end 658 of the shank portion 654. In particular, the front portion 1454 may have a projection 1456 for engaging the recess 674 and a portion 1458 for engaging the channel 666 of the head portion 652. The positioner 1450 may also have a handle 1460, which may be attached on the shaft 1452 to match the orientation of the portion 1458 in channel 666. Therefore, when the portion 1458 engages the channel 666 of the screw 650, the handle 1460 may be aligned with the direction of the channel 666. Such a construction may provide an operator with a visual indicator outside of the body of the orientation of the channel 666 within the body. The handle 1460 may be aligned with visual indicators (e.g., flat surface 713, flattened surface 812*a*) on the insertion cannulas to align the channel(s) of the insertion cannulas with the channel 666.

In use, the positioner 1450 may engage the bone screw 650 after the screw 650 has been positioned within a working cannula 475, retractor 500 and/or insertion cannula. Alternatively, the positioner 1450 may be used to insert a screw 650 down a working cannula 475, retractor 500 and/or insertion cannula. An operator may manipulate the positioner 1450 to rotate the head portion 652 of the screw 650. For example, the positioner 1450 may be used to orient the channel 666 with the corresponding channels of an insertion cannula prior to fixing the orientation of the head portion 652 with respect to an insertion cannula and/or inserting a fixation rod. Alternatively, the positioner 1450 may be used to manipulate the head portion 652 of the screw 650 after the head portion 652 has already been fixed with respect to the insertion cannula. In this way, the positioner 1450 may be used to align channels 666 of multiple screws 650 so that a fixation rod may be inserted therethrough.

5. Screwdriver

A screwdriver 1500 may be positioned within the working cannula 475, retractor 500, and/or an insertion cannula 700, 800, 900, 1100, 1200 and may engage a screw 650. As shown in FIGS. 15A through 15D, the screwdriver 1500 may comprise a shaft 1510, a locking sleeve 1520 and a holding sleeve 1530. The shaft 1510 may have an engagement portion 1516 at a distal end 1514 and coupling portion 1513 at a proximal end 1512. Moreover, the shaft 1510 may be cannulated (i.e., having a channel (not shown) therethrough for accepting, for example, a guide wire 150). As shown in FIG. 15B, the engagement portion 1516 may be in the shape of a hexagon to engage the recess 674 of the screw 650. And, the distal end

1514 may also have at least one shoulder 1518 for engaging the U-shaped channel of the head portion 652 of the screw 650.

Figure 15A:
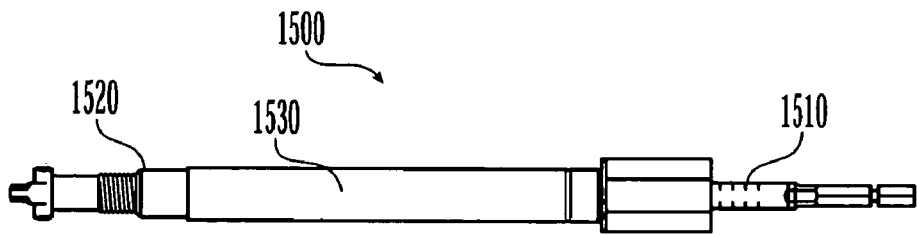
FIG. 15A is a side view of an exemplary embodiment of a screwdriver.
Figure 15B:
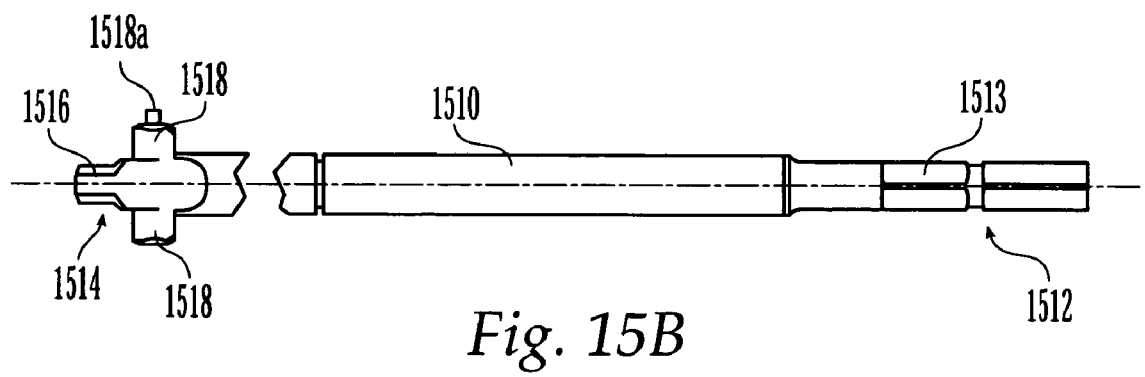
FIG. 15B is a side view of an exemplary embodiment of an inner shaft of the screwdriver of FIG. 15A.

Moreover, the coupling portion 1513 may be coupled to a handle portion, such as handle 1515 (FIG. 15E) for manual operation of the screwdriver 1500. The handle 1515 may be T-shaped or any other shape. In an embodiment where the screwdriver 1500 may be cannulated, the handle 1515 may also have a channel (not shown) passing therethrough that may align with the channel through the shaft 1510 so that a guide wire 150 may be inserted therein. Alternatively, the coupling portion 1513 may be connected to a device having a motor for rotating the screwdriver 1500, for example, a power drill. The handle 1515 may be positioned on the shaft 1510 to match the orientation of the shoulders 1518. Therefore, when the shoulders 1518 engage the channel 666 of the screw 650, the handle 1515 may be aligned with the direction of the channel 666. Such a construction may provide an operator with a visual indicator outside of the body of the orientation of the channel 666 within the body. The handle 1515 may be aligned with visual indicators (e.g., flat surface 713, flattened surface 812a) on the insertion cannulas to align the channel(s) of the insertion cannulas with the channel 666.

Figure 15C:
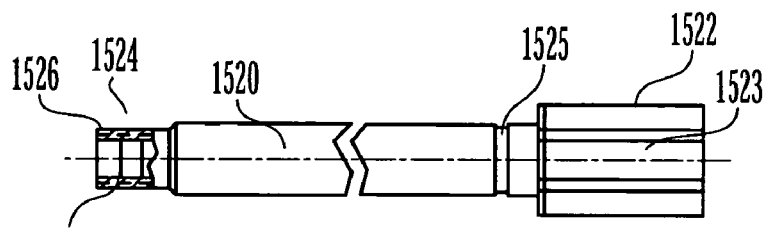
FIG. 15C is a partial cross-sectional view of an exemplary embodiment of a first sleeve of the screwdriver of FIG. 15A.

FIG. 15C shows the locking sleeve 1520. The shaft 1510 may be positioned within a channel 1528 of the locking sleeve 1520 such that the locking sleeve 1520 may slide along the shaft 1510. The locking sleeve 1520 may comprise a gripping end 1522 and a screw engaging end 1524. The gripping end 1522 may have a surface 1523, which may have a treatment (e.g., knurling) or a grip for allowing an operator to firmly grasp the locking sleeve 1520. In another embodiment, the gripping end 1522 may have at least one indentation or groove (not shown) for grasping. The screw engaging end 1524 may have an external threaded portion 1526 for engaging the internal threaded portion 672 of the head portion 652.

Figure 15D:
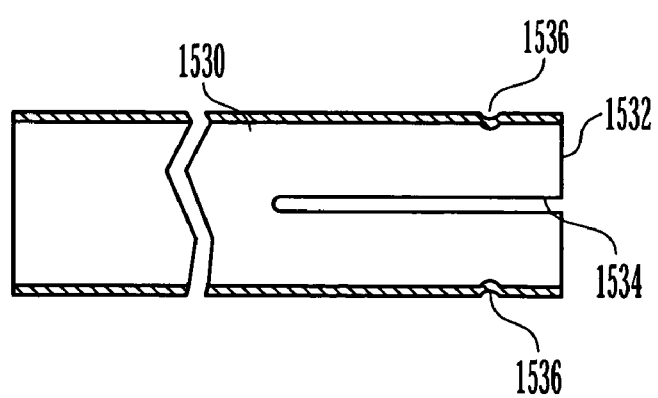
FIG. 15D is a cross-sectional view of an exemplary embodiment of a second sleeve of the screwdriver of FIG. 15A.
Figure 15E:
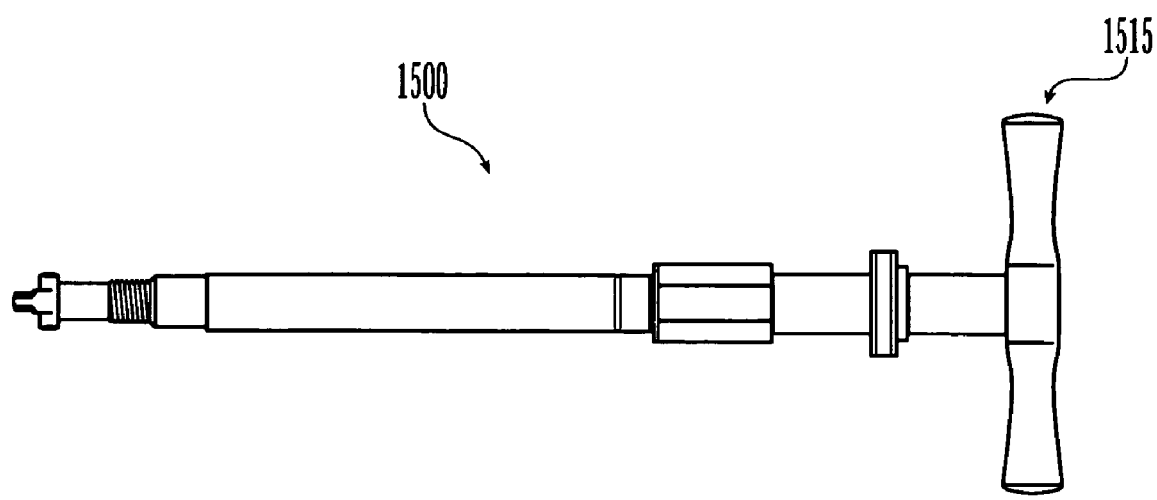
FIG. 15E is a side view of the screwdriver of FIG. 15A with an exemplary handle portion.

As shown in FIGS. 15A and 15D, the holding sleeve 1530 may be sized to fit over the locking sleeve 1520. The holding sleeve may extend out of an insertion cannula 700, 800, 900, 1100, 1200 so that an operator may hold the screwdriver 1500 while, at the same time, rotate the screwdriver 1500 to insert a screw 650 into a vertebra. The holding sleeve 1530 may be connected to the locking sleeve 1520 such that the holding sleeve 1530 may rotate, but not move axially, with respect to the locking sleeve 1520. In one embodiment, the holding sleeve 1530 may have one or more longitudinal slots 1534 and a protrusion 1536, which may extend around the inner periphery of the holding sleeve 1530. The slots 1534 may allow a proximal end 1532 of the holding sleeve 1530 to flex, thereby enabling the protrusion 1536 to be snapped into and/or out of engagement with the groove 1525 (FIG. 15C) of the locking sleeve 1520. The groove 1525 may extend around the periphery of the locking sleeve 1520. In another embodiment, the holding sleeve 1530 may have one or more protrusions (not shown), which may engage one or more grooves (not shown) of the locking sleeve 1520.

Additionally, in one embodiment having two shoulders 1518, one shoulder 1518 may have a protrusion 1518a (FIG. 15B) extending therefrom. It should be noted that, in some embodiments, there may be no protrusion 1518a. The protrusion 1518a may be received in and move along recess 730 of cannula 700 (FIG. 7C), recess 860 of cannula 800 (FIG. 8C) and/or recess 938 of cannula 900 (FIG. 9C). When the screwdriver 1500 is inserted in an insertion cannula, the screwdriver 1500 may move down the insertion cannula, guided by the protrusion 1518a in the recess 730, 860, 938. Thereafter, the screwdriver 1500 may be rotated to drive the screw 650 into a vertebra. The insertion cannula may rotate with the rotation of the screwdriver 1500. In one embodiment where the protrusion 1518 may be disengaged from the recess 730, 860, 938 during insertion of the screw 650, the screwdriver 1500 may not be withdrawn from the screw 650 until the protrusion is re-aligned with the recess 730, 860, 938. And, because of the position of the screwdriver 1500 within the screw 650, upon alignment of the protrusion 1518a with the recess 730, 860, 938, the channel 666 of the screw 650 may be aligned with the channels or slots 722 and/or 727, 822 and/or 827, or 928. The screwdriver 1500 may then be withdrawn from the screw 650 and the insertion cannula, and the screw 650 may be subsequently fixed with respect to the insertion cannula as described above.

Figure 15F:
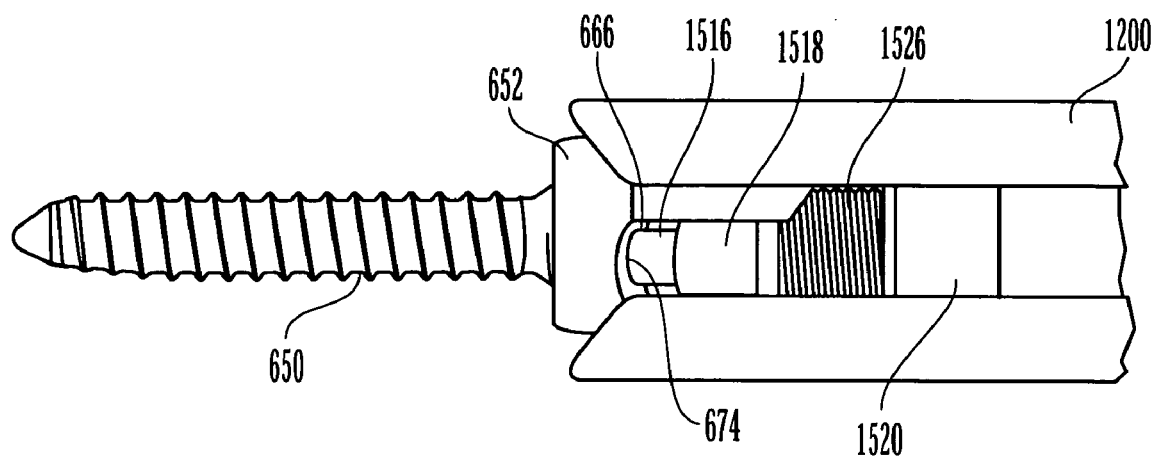
FIG. 15F is a side view of the screwdriver of FIG. 15A positioned in the insertion cannula of FIG. 12A and engaging the screw of FIG. 6A.

In use, the screwdriver 1500 may be inserted into the screw 650. As shown in FIG. 15F, the engagement portion 1516 may engage the recess 674 and the shoulder 1518 may engage the U-shaped channel 666. The locking sleeve 1520 may be moved from a first position where the screw engaging end 1524 of the locking sleeve 1520 may be positioned away from shoulder 1518 (FIG. 15E) to a second position where the screw engaging end 1524 of the locking sleeve 1520 may be positioned proximate the shoulder 1518 (FIG. 15F). The external threaded portion 1526 of the locking sleeve 1520 may engage the internal threaded portion 672 of the head portion 652 of the screw 650. Thus, the screwdriver 1500 may be axially and rotationally fixed with respect to the screw 650. The head portion 652 and the shank portion 654 may be rigidly fixed together, thereby allowing for implantation of the bone screw 650. The screwdriver 1500, screw 650 and insertion cannula 700, 800, 900, 1100, 1200 may be connected together and inserted into the patient at the same time. For example, as shown in FIG. 15F, the screwdriver 1500, screw 650, and cannula 1200 may be inserted into a patient as a single unit. Alternatively, the screwdriver 1500 may be inserted along with the screw 650 into the working cannula 475, retractor 500 and/or insertion cannula 700, 800, 900, 1100, 1200 after the working cannula 475, retractor 500 and/or insertion cannula 700, 800, 900, 1100, 1200 have already been inserted into a patient. In another embodiment, the screw 650 and working cannula 475, retractor 500, and/or insertion cannula 700, 800, 900, 1100, 1200 may be positioned in the body and the screwdriver 1500 may be subsequently inserted therein.

Once the screw 650 is positioned near a vertebra, the screwdriver 1500 may be rotated until the screw 650 is inserted a desirable distance into a vertebra. Thereafter, the screwdriver 1500 may be removed from the working cannula 475, retractor 500 and/or insertion cannula 700, 800, 900, 1100, 1200.

Figure 15G:
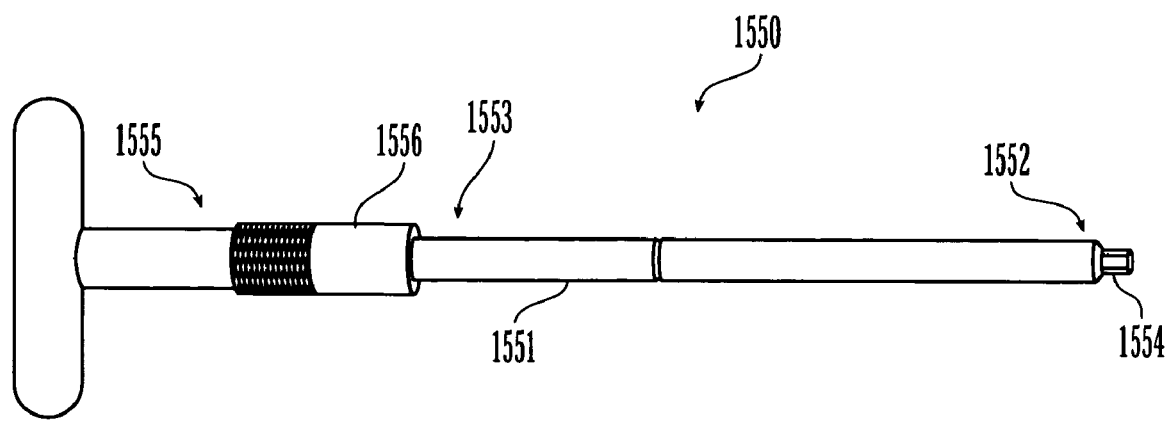
FIG. 15G is a side view of another exemplary embodiment of a screwdriver.

In a procedure using the cannula 1000, a screwdriver, such as screwdriver 1550 (FIG. 15G), may be used to insert a screw 650. The screwdriver 1550 may have a shaft 1551 with a distal end 1552 and a proximal end 1553, a hex portion 1554 at the distal end 1552, and a handle 1555 at the proximal end 1553. The hex portion 1554 may engage recess 674 of screw 650. Moreover, the handle 1555 may be integral with the shaft 1551 or may be a separate piece attachable to the shaft 1551.

To engage the screwdriver 1550 with the cannula 1000, cannula 1000 may comprise an external threaded portion (not shown) on proximal end 1012, which may engage an internal thread portion (not shown) within an enlarged portion 1556 of screwdriver 1550. In such a construction the enlarged portion 1556 may be mounted so that the enlarged portion 1556 may move axially and/or rotationally about the shaft 1551 and the handle 1555. Thus, upon fixing the enlarged portion 1556 to the cannula 1000, the shaft 1551 and handle 1555 may be rotated and/or moved axially with respect to the cannula 1000. In other embodiments, the enlarged portion 1556 may be fixed with respect to the shaft 1551 and/or handle 1555. In another embodiment, the screwdriver 1550 may be held within bore 1016 by at least one finger 1034, which may flex to snugly engage the screwdriver 1550. Furthermore, each finger 1034 may be provided with at least one protrusions 1036, which may engage the screwdriver 1550. It should, however, be understood that screwdriver 1550 may be used with any other insertion cannula, such as cannula 700, 800, 900, 1100, 1200.

Similar to screwdriver 1500, screwdriver 1550 may be inserted into the body as a single unit with an insertion cannula and screw 650. Alternatively, the screwdriver 1550 may inserted into an insertion cannula and/or screw 650 after the insertion cannula and/or screw 650 have been inserted into the body.

6. Rod Inserter

Once the screw 650 has been inserted, the positioner 1450 and/or insertion cannulas may be used to move the head portion 652 of the screw. In a procedure involving the use of multiple screws 650 and a fixation rod, the ability to move the head portion 652 may be desirable. In particular, using the positioner 1450 and/or an insertion cannula to move the head portions 652 may enable an operator to align adjacent head portions 652 so that a fixation rod may easily be inserted through the channels 666 of all the head portions 652.

The type of inserter used may depend on the type of insertion cannula, which has been used by an operator in performing a surgical procedure. For instance, in procedures using an insertion cannula 700, 800, 900, 1000, 1100 or 1200 an inserter such as inserter 1600 (FIG. 16A) or inserter 1700 (FIG. 17) may be used to insert a fixation rod from the side of a screw 650. Moreover, in procedures using devices such as insertion cannula 1100 and/or cannula 1200, a rod inserter similar to inserter 1800 (FIG. 18) may be used to insert a fixation rod through the top of a screw 650. In a procedure using the positioner 1450, the positioner 1450 may be removed prior to insertion of a fixation rod.

a. Side Inserter

Figure 16A:
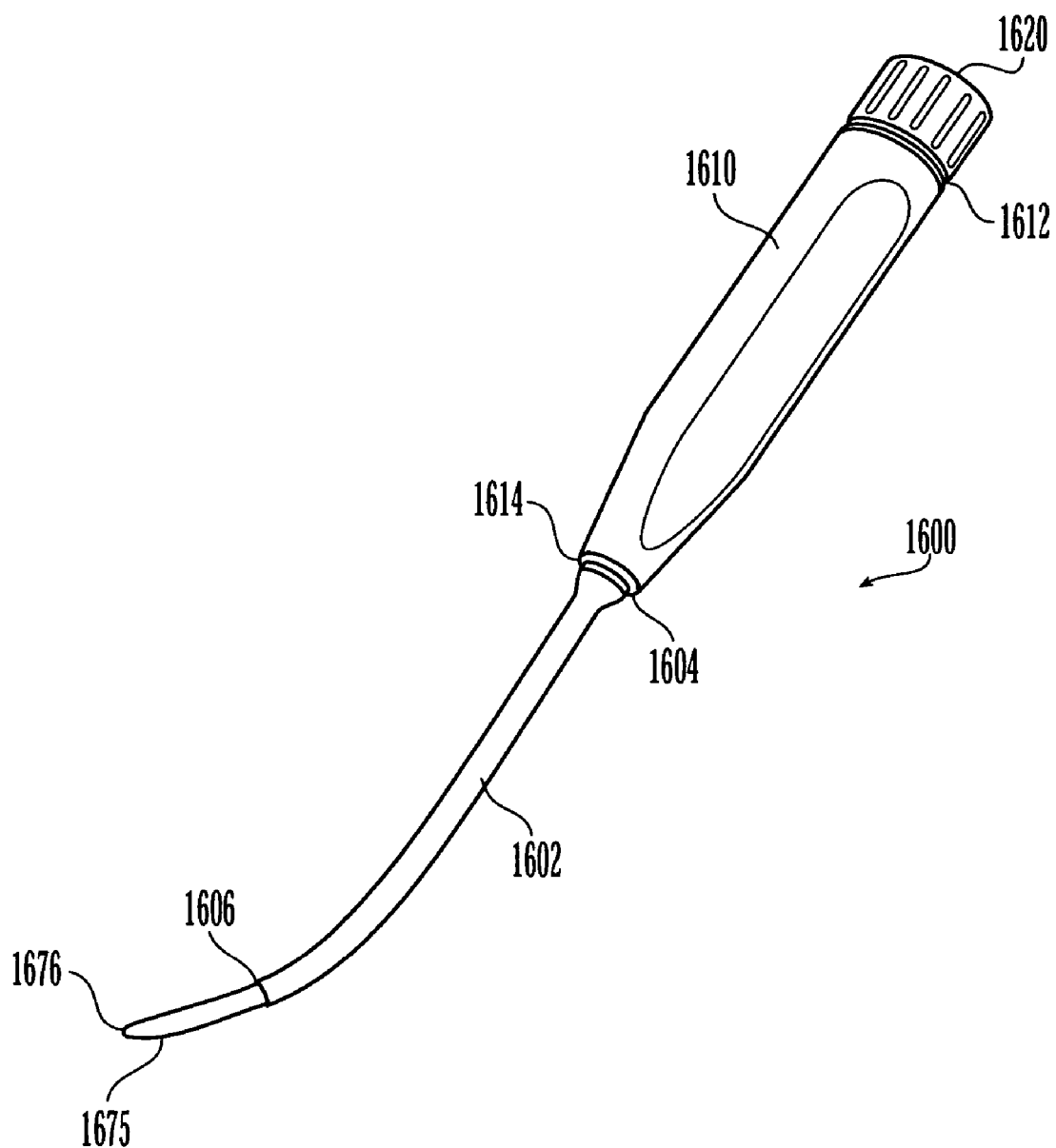
FIG. 16A is a perspective view of an exemplary embodiment of a rod inserter.
Figure 16B:
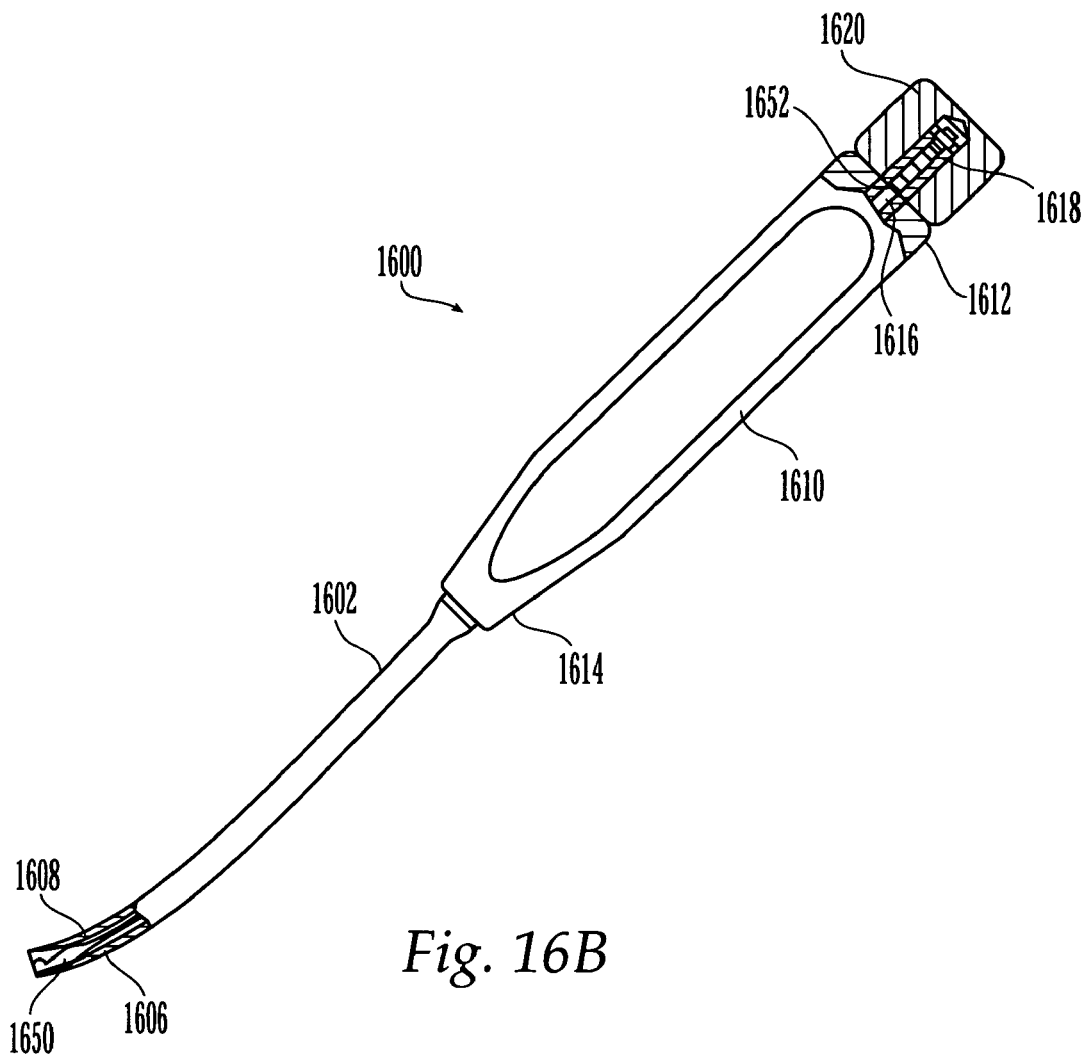
FIG. 16B is a partial cross-sectional view of the rod inserter of FIG. 16A.

FIGS. 16A and 16B show a rod inserter 1600, which may be used to engage and insert a fixation rod 1675 into a patient and through the side of a screw 650. It should, however, be appreciated that inserter 1600 may be used to insert a rod from the top of a screw 650. The rod inserter 1600 may comprise an elongated member 1602, a moveable member 1650, and an actuating member 1620 operably attached to the moveable member 1650. While the moveable member 1650 may be positioned inside the elongated member 1602, the moveable member 1650 may also be positioned on the outside of the elongated member 1602. Moreover, the inserter 1600 may have a handle portion. It should be understood that any portion of the inserter 1600 that may be grasped by an operator may be considered to be a handle portion. A handle portion 1610 may be connected to the proximal end 1604 of the elongated member 1602. Alternatively, the handle portion 1610 may surround the elongated member 1602, which may extend through the handle 1610 and which may connect directly to the actuating member 1620. The handle portion 1610 may have a grip or a surface treatment, such as knurling, to allow an operator to grasp the inserter 1600. In one embodiment, the handle 1610 may have a diameter, which may be larger than the diameter of the elongated member 1602.

The components of the inserter 1600 may be made, for example, of metal, plastic, rubber, a composite material, or a combination of materials. For example, the components may be made from stainless steel, titanium, aluminum, an alloy, carbon fiber composite, or a polymer (e.g., polyvinyl chloride (PVC), polyethylene, polyesters of various sorts, polycarbonate, Teflon coated metal, polyetherether ketone (PEEK), ultra high molecular weight polyethylene (UHMWPE)). In addition, various methods may be used to make the components of the inserter 1600, including casting, extrusion, injection molding, compression molding, forging, machining, or transfer molding.

Various factors may be considered when determining the material used to make the various components of the inserter 1600, including ability to withstand sterilization/cleaning (e.g., using an autoclave; cleaning products used for sterilization in hospitals), weight, durability, resistance to staining (e.g., from blood or substances used in surgery) and the ability to grip the components, particularly with latex gloves which are generally used during surgery. The handle 1610 may be made of the same or different material as the other components.

As shown in FIGS. 16A and 16B, the elongated member 1602 may comprise a proximal end 1604, a distal end 1606, and a passageway 1608 extending from the proximal end 1604 to the distal end 1606. The proximal end 1604 of the elongated member 1602 may be positioned adjacent a handle portion 1610. Alternatively, the proximal end 1604 of the elongated member 1602 may be located proximate an actuating member 1620. The elongated member 1602 may be have a curved shape, such as shown in FIG. 16A, or may be straight. The radius of curvature of the elongated member 1602 may be, for example, between about 80 mm and about 120 mm and, more preferably, between about 90 mm and about 110 mm and, most preferably, between about 95 mm and about 105 mm. The fixation rod 1675 may also be curved and may have the same or different radius of curvature. In other embodiments, the fixation rod 1675 may be straight.

The handle portion 1610 may have a proximal end 1612, a distal end 1614, and a passageway 1616 therethrough. In an embodiment where the handle portion 1610 and the elongated member 1602 may be separate pieces, the handle portion 1610 and the elongated member 1602 may be joined together by, for example, a screw, nut, bolt, threads, adhesive or welding. In an embodiment where the elongated member 1602 may engage the actuating member 1620, the elongated member 1602 may extend through the passageway 1616 of the handle portion 1610 and may engage a channel 1618 of the actuating member 1620.

The actuating member 1620 may be positioned proximate the proximal end 1612 of the handle portion 1610. The actuating member 1620 may be rotatable with respect to the handle portion 1610 and/or the elongated member 1602. Rotation of the actuating member 1620 may cause the moveable member 1650 to move within the passageway 1608 of the elongated member 1602.

Figure 16C:
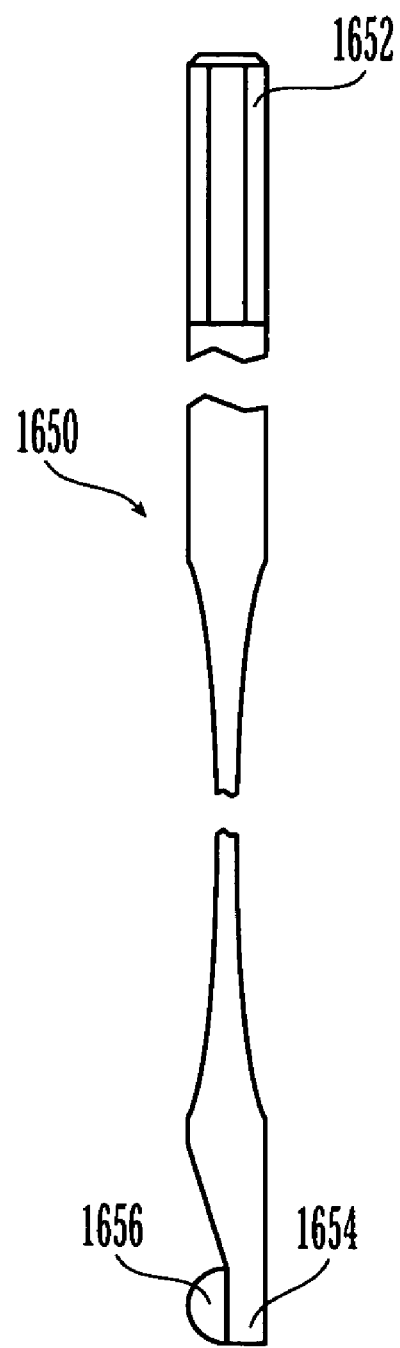
FIG. 16C is a side view of an exemplary embodiment of a moveable member of the rod inserter of FIG. 16A.

The moveable member 1650 may be positioned within the passageway 1608 of the elongated member 1602, may extend through the handle portion 1610 and may be operably connected to the actuating member 1620. The moveable member 1650 may be flexible or rigid. In one embodiment, the moveable member 1650 may be a cable. As shown in FIG. 16C, the moveable member 1650 may have a proximal end 1652 and a distal end 1654. The proximal end 1652 of the moveable member 1650 may be received in the channel 1618 of the actuating member 1620. The moveable member 1650 may be connected to the actuating member 1620 such that the moveable member 1650 moves within the channel 1608 of the elongated member 1602 when the actuating member 1620 is rotated. The distal end of the moveable member 1650 may be, for example, hook-like. In one embodiment, a protrusion 1656 may be positioned on the distal end 1654 of the moveable member 1650 for engaging and securely holding the fixation rod 1675 (FIG. 16A) in the passageway 1608 of the inserter 1600. It will be appreciated that the moveable member 1650 may be a single piece or separate pieces attached together. As a separate piece, for example, the moveable member 1650 may be made of a cable connected to a hook-like portion, which may engage a fixation rod.

Upon rotation of the actuating member 1620, the moveable member 1650 may be moved from a first position where a distal end 1654 of the moveable member 1650 extends out of the distal end 1606 of the elongated member 1602 to a second position where the entire moveable member 1650 may be positioned within the elongated portion 1602. When the actuating member 1620 is rotated in the opposite direction, the moveable member 1650 may move from the second position to the first position.

To engage a fixation rod 1675, the actuating member 1620 may be rotated so that the distal end 1654 of the moveable member 1650 may move outside of the elongated member 1602. The protrusion 1656 may engage a receiving portion (not shown) of the fixation rod 1675. One skilled in the art would appreciated that any means of connecting the fixation rod 1675 to the elongated member 1602 is envisioned (e.g., threads) so long as the rod 1675 may be disengaged from the inserter 1600. The actuating member 1620 may then be rotated in the opposite direction so that the moveable member 1650 may be drawn back into the elongated member 1602 with the fixation rod 1675. In this position, the fixation rod 1675 may be fixed securely with respect to the inserter 1600.

The fixation rod 1675 may then be inserted into a patient and into a head portion 652 of a screw 650. The rod 1675 may have a tip 1676, which may be sharp and/or pointed to facilitate the rod's movement through tissue. Once the rod 1675 is in position, the actuating member 1620 may once again be rotated to extend the moveable member 1650 from the elongated member 1602. The rod 1675 may then be disengaged from the inserter 1600 and the inserter 1600 may be removed from the patient, leaving the rod 1675 in place. In an embodiment where, for example, two screws 650 may be inserted into the vertebrae through two separate insertion sites spaced apart from one another, the inserter 1600 (or any side inserter, such as 1700) may provide the advantage of allowing a fixation rod to be inserted into the screws 650 underneath the skin and muscle, without the need to make an additional incision through skin and muscle between the insertion sites of the screws 650. Such a procedure may minimize trauma to the body. It should be noted that any means of inserting a rod 1675 into a patient and through the head portion 652 of a screw 650 is envisioned preferably where the rod 1675 may be disengaged from an inserter.

Figure 17:
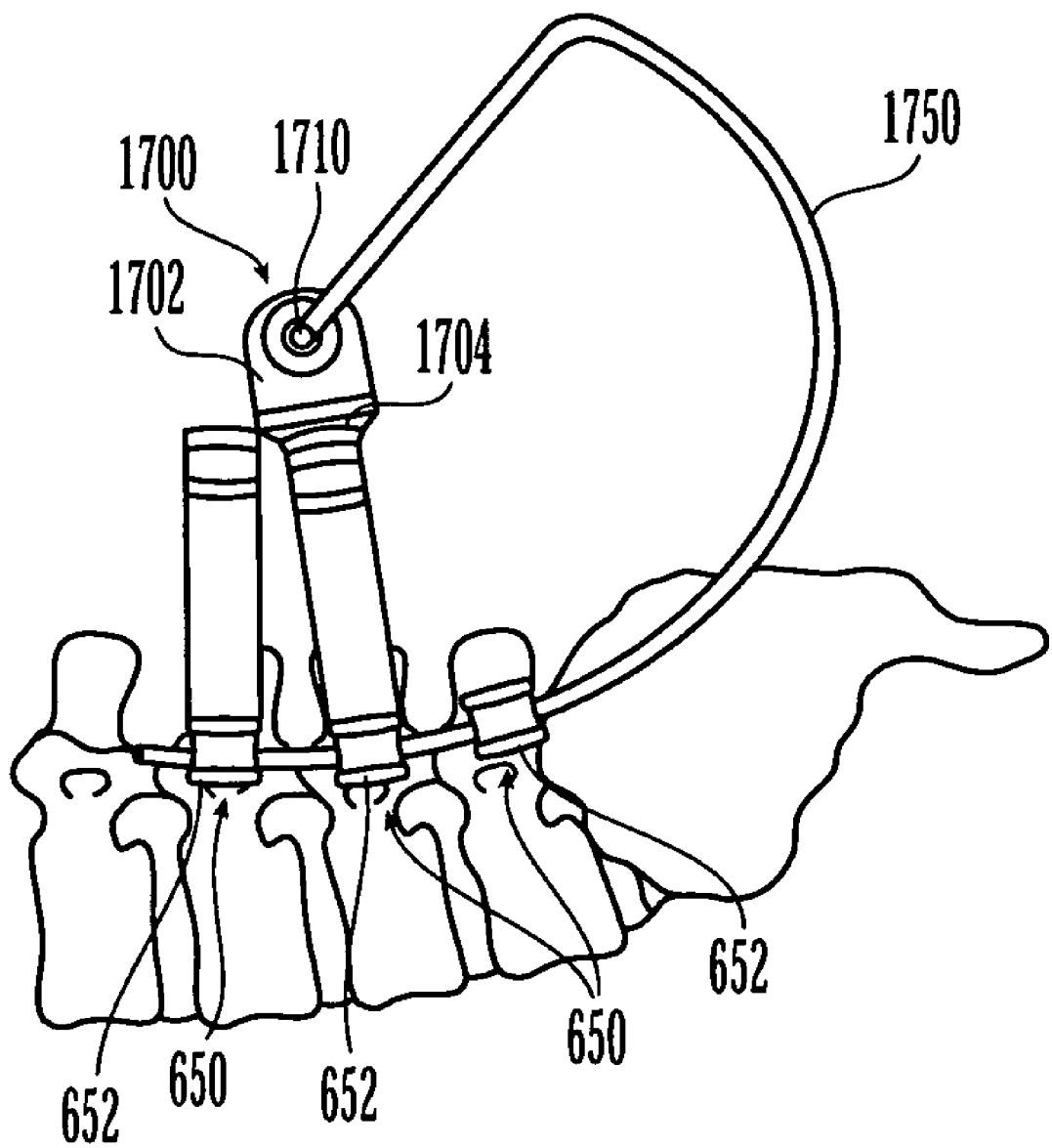
FIG. 17 is a side view of another exemplary embodiment of a rod inserter engaging insertion cannulas and having a rod positioned through the screws of FIG. 6A.

As an alternative to the inserter 1600, an inserter 1700 may be used to insert a rod 1750 into a patient and through a head portion 652 of a screw 650. The inserter 1700 may comprise a body portion 1702 and an engagement portion 1704. As shown in FIG. 17, the inserter 1700 may be connected to the top portion of an insertion cannula such as those describe above. In other procedures, the inserter 1700 may be connected to the top of a working cannula 475 or retractor 500. Further, the inserter 1700 may be attached directly or indirectly (through another component) to the working cannula 475, retractor 500, and/or insertion cannula at any position along the length of the working cannula 475, retractor 500, and/or insertion cannula.

The engagement portion 1704 may comprise, for example, threads (not shown) for engaging corresponding threads (not shown) on the proximal end of the working cannula 475, retractor 500, and/or insertion cannula. Alternatively, the engagement portion 1704 may comprise a clip (not shown) for engaging a clip engaging portion (not shown) on the working cannula 475, retractor 500, and/or insertion cannula. However, any method of connecting two components known to those of skill in the art is envisioned.

The rod 1750 may be rotatable with respect to the inserter 1700. For example, a portion of the rod 1750 may be inserted in opening 1710 of inserter 1700 and fixed to inserter 1700 such that the rod 1750 may rotate within the opening 1710. The rod 1750 may be formed to define a path of travel, which may be arcuate in shape. Where more than one insertion cannula may be used, the insertion cannulas may be fixed with respect to each other. Consequently, the head portions 652 of the screws 650 attached to the insertion cannula may also be in a fixed orientation. The orientation of the insertion cannula and the head portion 652 may be a factor that sets the path of travel of the rod 1750. In order to insert the rod 1750 into the head portion, the rod 1750, which starts from a position outside of a patient's body, may be swung through an arc into a patients body such that the rod 1750 passes through the head portions 652 of the screws 650. A portion of the rod 1750 may then be disengaged from the remainder of the rod 1750 and may remain in the screws 650 as the remainder of the rod 1750 may be removed from the body. It should be appreciated that any device which connects to a working cannula 475, retractor 500, and/or insertion cannula and may move a fixation rod through an arcuate path into a screw 650 is envisioned.

b. Top Inserter

Figure 18:
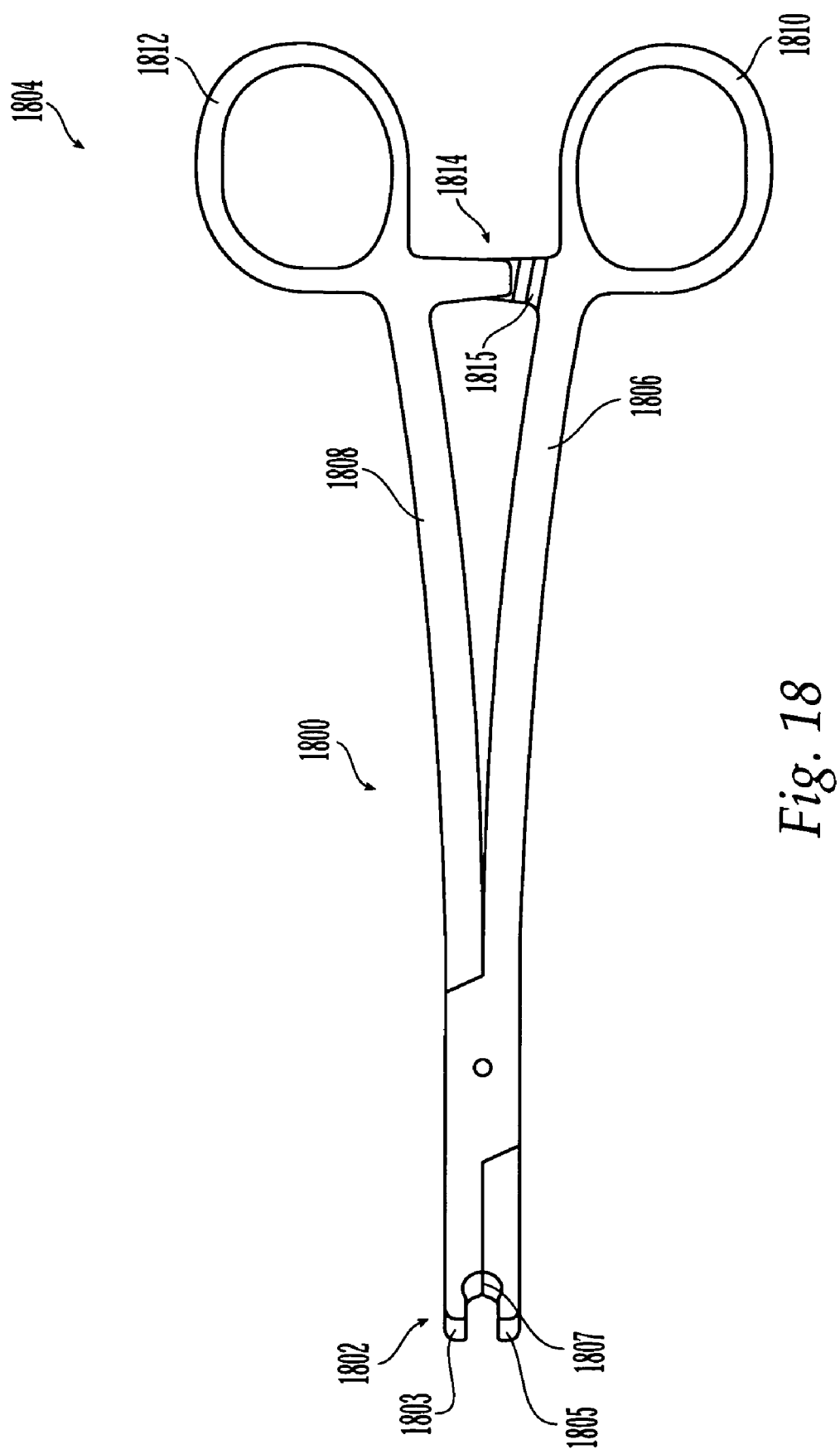
FIG. 18 is a side view of another exemplary embodiment of a rod inserter.

FIG. 18 illustrates an embodiment of a rod inserter which may be used to insert a fixation rod from the top of a screw 650. The rod inserter 1800 may comprise a distal end 1802 and a proximal end 1804. The inserter 1800 may also comprise a first elongated member 1806 and a second elongated member 1808 which may be rotatably connected to each other. The first elongated member 1806 may have a first jaw portion 1803 and the second elongated member 1808 may have a second jaw portion 1805. The jaw portions 1803, 1805 may define an engagement portion 1807 therebetween into which a fixation rod may be inserted. Both the first and second elongated member 1806, 1808 may have a gripping portion 1810, 1812, respectively, such that an operator may be able to hold the portion 1810, 1812 and move the elongated member 1806, 1808 relative to each other. In one embodiment, the gripping portions 1810, 1812 may be scissor-type griping portions into which an operator may be able to position at least one finger. Moreover, the gripping portions 1810, 1812 may have a locking mechanism 1814 to hold the elongated members 1806, 1808 in a fixed position relative to each other. In one embodiment, the locking mechanism 1814 may comprise mating teeth 1815 to fix the elongated portion 1806, 1808 at fixed intervals relative to each other.

In operation, an operator may separate the gripping portions 1810 and 1812. This, in turn, may result in the jaw portions 1803, 1805 moving apart from one another, and the engagement portion 1807 may increase in size to receive a fixation rod. Once a rod is inserted in the engagement portion 1807, an operator may move the gripping portions 1810, 1812 back together so that the rod may be fixed within the engagement portion 1807 and between jaw portions 1803, 1805. The elongated member 1806, 1808 may be held in position by locking mechanism 1814. An operator may then use the inserter 1800 to insert a rod, such as rod 1900, down insertion cannulas 1100 (FIG. 19A) and/or cannulas 1200 (FIG. 19B) and through the top of screws 650. It should be understood that other instruments that may be attached to a fixation rod may be used to move the rod down into the screws.

C. Methods for Less Invasive Surgery

To perform a spinal fixation procedure, a surgeon may use a radiographic image of the spine to determine one or more insertion points on a patient's back. One or more incisions may then be made depending on the procedure to be performed and the instruments which may be used. An incision may have a length, for example, between about 1 cm and about 10 cm and, more preferably, between about 2 cm and about 5 cm. A trocar 100 may be inserted into the incision(s), followed by a guide wire 150, which may be positioned adjacent to or into a vertebra. To insert the guide wire 150 into the vertebrae, a hammer or other surgical tool may be used to strike the guide wire 150 or cap 152. With the guide wire 150 in place, the trocar 100 may be removed. It should be noted that a trocar 100 may be unnecessary and the guide wire 150 may be positioned directly through the incision and adjacent or into a vertebra.

An inserter 200 may then be positioned down over the guide wire 150 towards the vertebrae. The incision may be dilating by inserting sequentially larger dilators 350 over the inserter 200. However, in one embodiment, the dilators 350 may be inserted directly over the guide wire 150 without the use of an inserter 200. When the incision(s) has been dilated to a size appropriate for the procedure to be conducted, in one embodiment, a working cannula 475 or retractor 500 may be inserted over the largest dilator 350. It should be understood that in some embodiments, a screw 650 and/or an insertion cannula may be inserted directly into the body without using a working cannula 475 and/or retractor 500 to dilate an incision. In one embodiment, an insertion cannula may be attached to an inserter, similar to inserter 200. The insertion cannula and inserter may be inserted into an incision as one unit, down to a vertebra. Once the working cannula 475, retractor 500 and/or insertion cannula are in position, the inserter 200 and/or dilator(s) 350 may be removed from the patient. The guide wire 150 may remain in place or may be removed. It should be noted that the working cannula 475, retractor 500 or insertion cannula may be inserted directly into the incision(s) (e.g., without the use of a trocar 100, guide wire 150, inserter 200 and/or dilators 350). The dilation process may be repeated for each incision.

An opening may be created by the working cannula 475, retractor 500 and/or insertion cannula. In an embodiment where a single insertion cannula may be inserted into a single opening, the opening may have a diameter, for example, between about 1 cm and about 4 cm and, more preferably, between about 1.5 cm and about 3 cm. Furthermore, in an embodiment where more than one insertion cannula may be inserted through a single opening, the opening may have a diameter, for example, between about 2 cm and about 10 cm and, more preferably, between about 2 cm and about 5 cm. It should be noted, however, that the opening may be any shape, for example, oval, circular, egg-shaped, square, rectangular, or otherwise polygonal.

In an embodiment using working cannula(s) 475, the drill 1350 may be inserted down a guide wire 150 (if present) and into the working cannula(s) 475 and may be rotated to create one or more cavities in the vertebrae into which one or more screws 650 may be positioned. When a working cannula 475 is large enough, an entire procedure may be performed through the working cannula 475. Moreover, in an embodiment where a retractor 500 may be used, the blades 502 of the retractor 500 may be spread apart so that the entire surgical procedure may be performed within the opening created by the blades 502 of the retractor 500. The drill 1350 may be inserted down a guide wire 150 (if present) and may be used to drill one or more holes in the vertebrae. Alternatively, the drill 1350 may be used (without the use of a guide wire 150) by an operator to create holes in any vertebrae, which may be accessed through the working cannula 475 and/or retractor 500. In some embodiments, multiple guide wires 150 may be used for creating multiple cavities and guide multiple tools to bone. It should also be understood that a drill may be positioned through an insertion cannula for drilling holes.

Figure 20A:
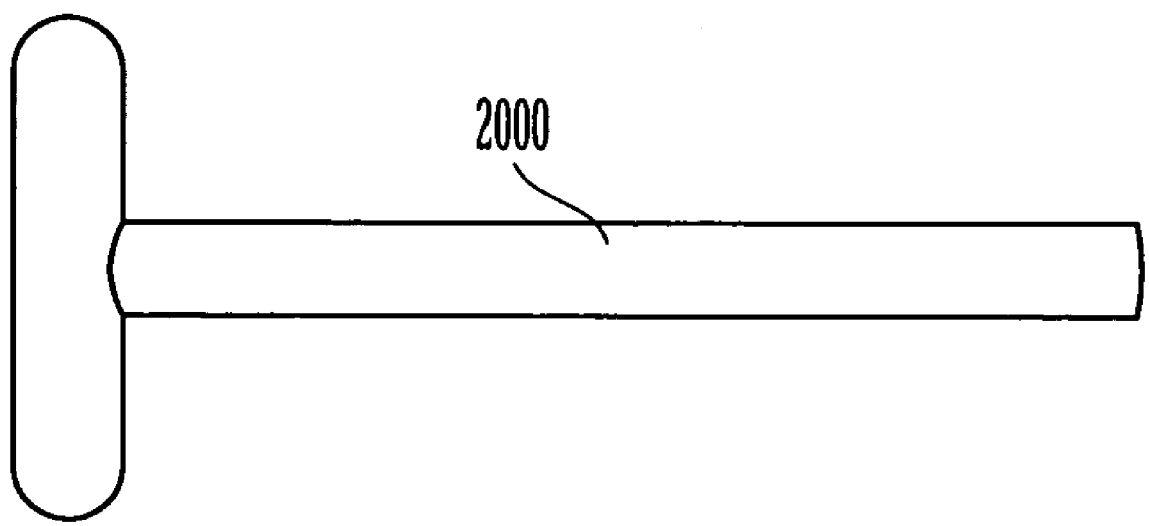
FIG. 20A is a side view of an exemplary embodiment of a pusher.
Figure 20B:
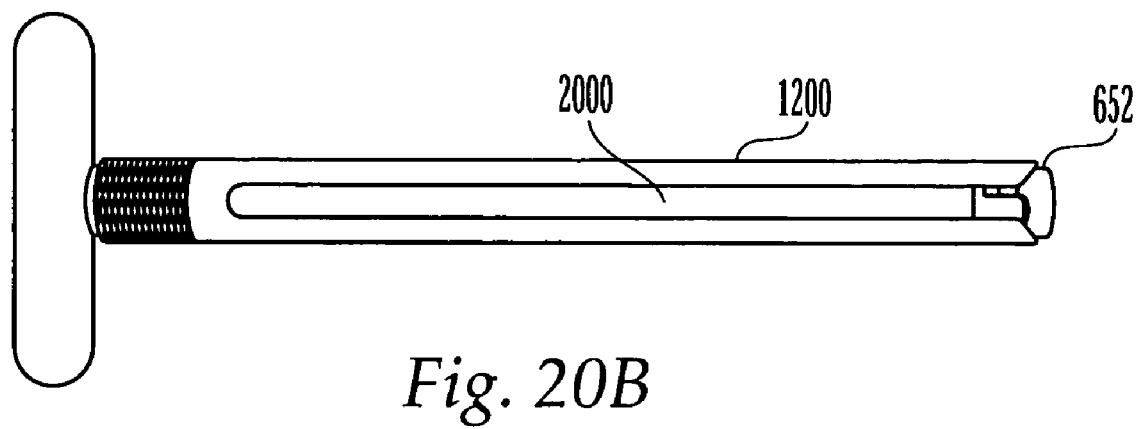
FIG. 20B is a side view of an exemplary embodiment of the pusher of FIG. 20A positioned in the insertion cannula of FIG. 12A.
Figure 20C:
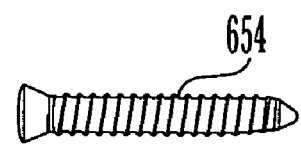
FIG. 20C is a side view of an exemplary embodiment of a shank portion of the screw of FIG. 6A.

In one embodiment, after the drilling step, one or more shank portions 654 (FIG. 20C) may inserted into vertebrae using a screwdriver 1500, 1550. In such an embodiment, a pusher 2000 (FIG. 20A) may be used to subsequently connect the head portions 652 and the shank portions 654. As illustrated in FIG. 20B, the head portion 652 may be connected to a distal end of insertion cannula 1200 and the pusher 2000 may be inserted into insertion cannula 1200. The entire assembly may then be inserted into a working cannula 475 or retractor 500. When the head portion 652 engages the shank portion 654, a translational force may be asserted by an operator on the pusher 2000 such that the head portion 652 snaps onto the shank portion 654. Thereafter, the pusher 2000 may be removed from the insertion cannula 1200 while the insertion cannula 1200 remains attached to the assembled screw 650. The same method may be performed using insertion cannulas 700, 800, 900, 1000 or 1100. In some embodiments, the pusher mechanism may be the insertion cannula itself and a pusher 2000 may be unnecessary. An operator may attach the head portion 652 to an insertion cannula 700, 800, 900, 1000, 1100 or 1200 and may assert a translational force to the insertion cannula to insert the head portion 652 on the shank portion 654.

Furthermore, in one embodiment where the shank portion 654 and head portion 652 may be inserted separately into the body, there may be no dilation mechanism used to created an opening in the patient. In such an embodiment an incision may be created through a patient's skin. A guide wire 150 may be inserted through the incision, down to a vertebra. The shank portion 654 may be inserted down the guide wire 150 and driven into the vertebra. The head portion 652, insertion cannula and pusher 2000 (if used) may be connected together and, as one unit, inserted down over the guide wire 150 until the head portion 652 engages the shank portion 654. The head portion 652 may be attached to the shank portion 654 and the pusher 2000 (if used) may subsequently be removed from the body, leaving the assembled screw 650 and the insertion cannula in the body.

In other embodiments, the bone screw 650 may be connected and/or fixed to insertion cannula 700, 800, 900, 1000, 1100 and/or 1200 as discussed above. One or more insertion cannulas 700, 800, 900, 1000, 1100 and/or 1200 (with screws 650 attached) may then be inserted into the working cannula 475 or the retractor 500 and may be guided by a guide wire (if present). In one embodiment, the insertion cannula 700, 800, 900, 1100 and/or 1200 may be positioned into the incision, working cannula 475 or retractor 500 without the screw 650. Thereafter, the screw 650 may be inserted down the insertion cannula 700, 800, 900, 1100 and/or 1200. In other embodiments, the bone screw 650 may be inserted through the working cannula 475 or the retractor 500 and driven into the cavity created by the drill 1350. The insertion cannula 700, 800, 900, 1000, 1100 and/or 1200 may then be inserted through the working cannula 475 or retractor 500 and may be connected and/or fixed to the screw 650.

An implantation mechanism such as a screwdriver 1500, 1550 may be used to drive a screw 650 into a vertebra. The screwdriver 1500, 1550 may be inserted into an insertion cannula 700, 800, 900, 1100 and/or 1200 before or after the insertion cannula is positioned in the body. In an embodiment where the screwdriver 1500, 1550 and screw 650 may be inserted into an insertion cannula after the insertion cannula is in the body, the screwdriver 1500, 1550 may be used to move a screw 650 down towards the distal end of an insertion cannula 700, 800, 900, 1100 and/or 1200. In an embodiment where a cannula 1000 may be used, the screwdriver 1550 may be inserted into insertion cannula 1000 before or after the cannula 1000 and screw 650 may be positioned in the body. Moreover, it will be appreciated by those skilled in the art that the insertion cannula may be the implantation mechanism and may be used to drive a screw 650 into bone. In such an embodiment, a screwdriver 1500, 1550 may be unnecessary. For example, in an embodiment where the head portion 652 and shank portion 654 may be one integral piece (e.g., where the head and shank may have a fixed orientation), upon fixing the insertion cannula with respect to the screw 650, the insertion cannula may be rotated to insert the shank portion 654 into a vertebra.

With the bone screw 650 properly located above the pedicle and the hole created by the drill 1350, the screwdriver 1500, 1550 may be rotated to drive the shank 654 of the bone screw 650 into the pedicle of a vertebra. In an embodiment where the threaded shank 654 is self-tapping, the shank 654 may be anchored to the vertebra upon rotation of the screw 650. Moreover, in an embodiment where a screw may be inserted down through an insertion cannula 700, 800, 900, 1100 and/or 1200, as the screw 650 is rotated, the screw 650 may move closer to the distal end of the insertion cannula 700, 800, 900, 1100 and/or 1200. Once the screw 650 is in the vertebra to a desirable extent, the screwdriver 1500, 1550 may be disengaged from the screw 650 and removed from the patient.

In an embodiment using cannula 700, 800, 900, 1100 and/or 1200, a positioner 1450 may be positioned through the insertion cannula 700, 800, 900, 1100 and/or 1200 and guided down a guide wire (if present). The positioner 1450 may be used to rotate the head portion 652 of the screw 650 so that the channel 666 aligns with the corresponding channel of the insertion cannula 700, 800, 900, 1100 and/or 1200. The insertion cannula 700, 800, 900, 1100 and/or 1200 may then be fixed to the screw 650 as described above. The positioner 1450 may be removed before or after the insertion cannula 700, 800, 900, 1100 and/or 1200 is fixed to the screw 650.

It should be noted that in some embodiments, the insertion cannula 700, 800, 900, 1000, 1100 and/or 1200 may be fixed with respect to the screw 650 prior to the screw 650 being inserted into the body and/or driven into bone. In such an embodiment, the insertion cannula 700, 800, 900, 1000, 1100 and/or 1200 may rotate with the screwdriver 1500, 1550 as the screw is being inserted into bone. Such a construction may provide the advantage of enabling an operator to align the channels of the respective insertion cannulas with channel 666 of the screw 650 outside the body, thus eliminating the need for alignment of the channels inside the body without direct visualization by a surgeon.

In a fixed state, the head portion 652 may be prevented from moving axially and/or rotationally with respect to the insertion cannula 700, 800, 900, 1000, 1100 and/or 1200. At the same time, the head portion 652 may pivot about the shank portion 654. Thus, an operator may use the insertion cannulas to orient the head portion 652 of the screws 650 so that the channel 666 aligns with the channel 666 of an adjacent screw 650. Thereafter, a fixation rod may be inserted in the head portions 652 of the screws 650.

The fixation rod may be inserted from the top or the side of the screw 650 depending upon the insertion cannula and/or rod inserter used by a surgeon. In a procedure where a fixation rod may be inserted from the side, an incision (separate from the incision through which the screw 650 is positioned) may be made in the patient at a distance from the incision containing the insertion cannulas. In a procedure where the rod is inserted from the top of the screw 650 and the screws 650 may be inserted through separate insertion cannulas (in separate openings), an incision may be made through the skin and muscle between the insertion cannulas so that a rod may be positioned down to the vertebrae. In an embodiment where a working cannula 475 or retractor 500 may be used, there may be no need to create a separate incision when the rod is inserted from the top of the screw 650 because there may be no tissue between the insertion cannulas.

The fixation rod may be guided into position by feel or by fluoroscopic guidance using inserter 1600, 1700, or 1800. In an embodiment using inserter 1600, a separate incision may be made a distance from the incision(s) used to insert the working cannula 475, retractor 500, and/or the insertion cannula 700, 800, 900, 1000, 1100, 1200. The inserter 1600 may be fixed to a rod 1675 as discussed above. The inserter 1600 may be used to guide the rod 1675 through the separate incision, underneath the skin and muscle located between adjacent screws 650, and into the channels 666 of the screws 650 from the side of the screw 650. The inserter 1600 may be disengaged from the rod 1675 and removed from the patient. The disengagement step may occur before or after the rod has been fixed to the screws 650. The inserter 1600 may be used in a way such that the inserter 1600 may not contact or engage any portion of an insertion cannula that may be located outside of the body (e.g., the inserter 1600 may contact a portion of an insertion cannula located only within the body).

In another embodiment, the engagement portion 1704 of the inserter 1700 may engaged the working cannula 475, retractor 500, and/or the insertion cannula. Adjacent insertion cannulas may be connected to one another such that the insertion cannulas may be in a fixed orientation relative to each other. Similar to insertion using the inserter 1600 above, a separate incision may be created in the patient. The rod 1750 may be rotated through the separate incision, underneath the skin and muscle located between adjacent screws 650, and into the channels 666 of the screws 650 from the side of the screw 650. A portion of the rod 1750 may be disengaged from the inserter 1700 and the remainder of the rod 1750 may be removed from the patient.

Figure 19A:
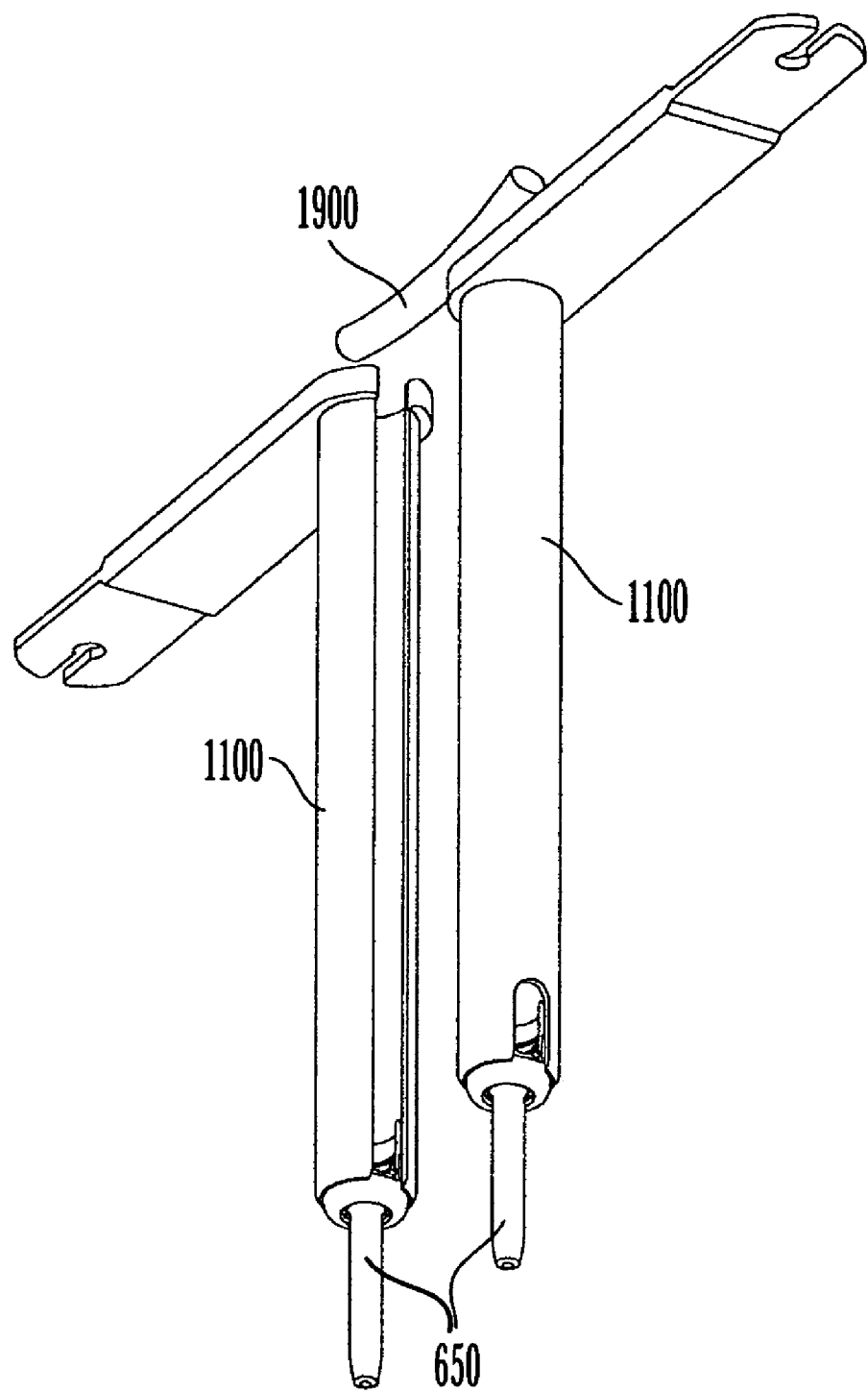
FIG. 19A is a perspective view of an exemplary embodiment of a rod being inserted into the insertion cannulas of FIG. 11A.
Figure 19B:
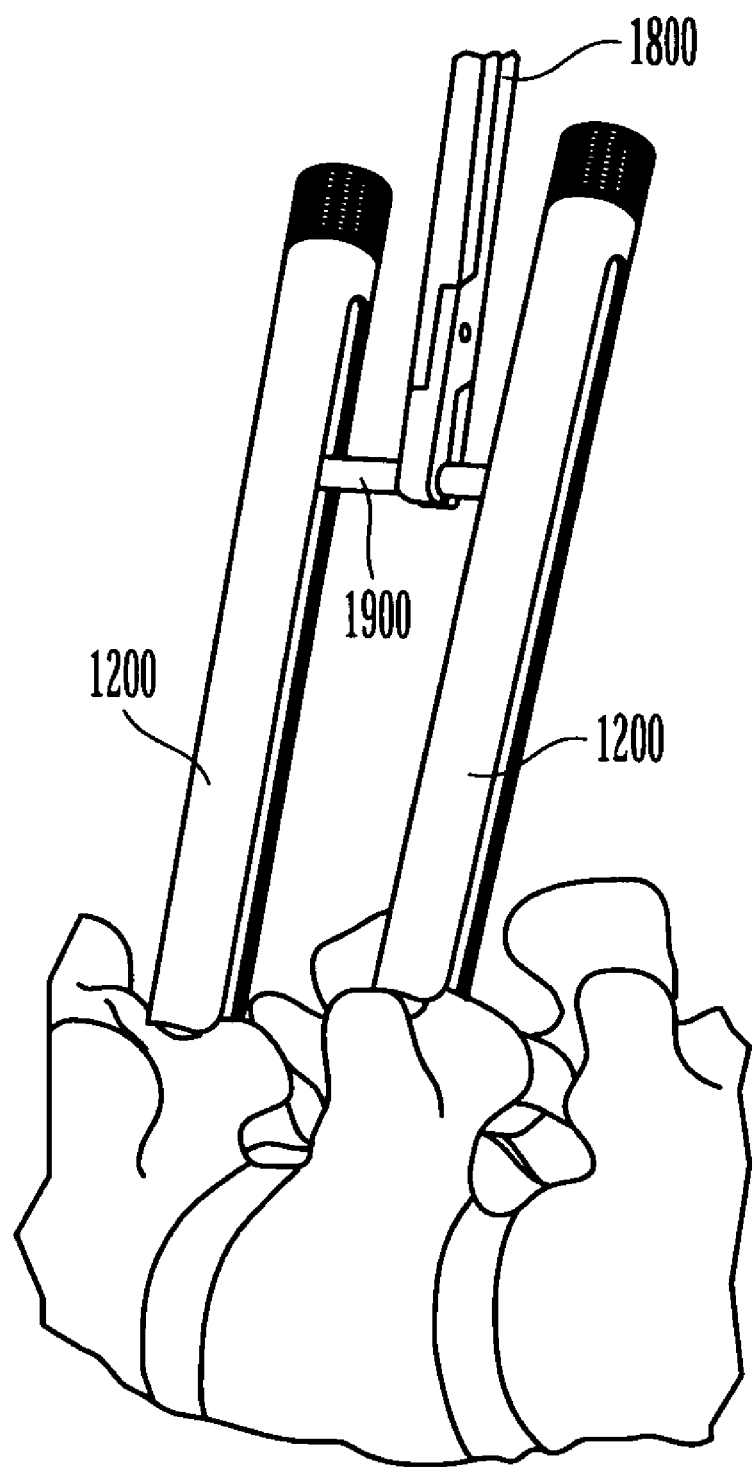
FIG. 19B is a perspective view of another exemplary embodiment of a rod being inserted into the insertion cannulas of FIG. 12A.

In an embodiment using the inserter 1800, a fixation rod may be inserted between the jaw portions 1803 and 1805 into the engagement portion 1807. The jaws 1803 and 1805 may be locked in position onto the fixation rod by engaging the mating teeth 1815 of locking mechanism 1814. As shown in FIGS. 19A and 19B, the inserter 1800 may then be used to position the fixation rod down through cannula 1100 or 1200 and into the head portion 652 of the screw 650. The inserter 1800 may be disengaged from the fixation rod and removed from the patient before or after the rod has been fixed to the screws 650.

In one embodiment, where two or more cannulas 1100, 1200 may be inserted into the body through separate openings in a patient, a fixation rod may be inserted down one cannula 1100, 1200 and rotated, underneath the skin, into at least one other cannula 1100, 1200. Similar to a side insertion technique, such a technique may provide the advantage of allowing a fixation rod to be inserted into the screws 650 underneath the skin and muscle, without the need to make an additional incision through skin and muscle between two or more cannulas 1100, 1200.

A surgeon may be able to directly visualize the rod being inserted through the screw 650 by looking down into the working cannula 475, retractor 500, and/or insertion cannulas. It should be understood, however, that in some techniques, an operator may insert a fixation rod down and/or into the insertion cannulas without the use of any device by using his/her hands and/or fingers. As the fixation rod is being inserted, the insertion cannula may be manipulated to further facilitate introduction of the fixation rod.

Figure 21:
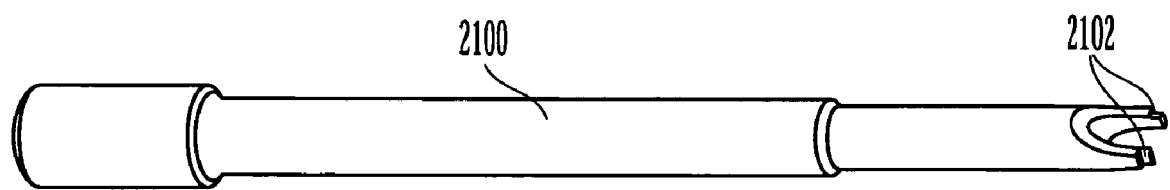
FIG. 21 is a perspective view of an exemplary embodiment of a locking cap screwdriver.
Figure 22:
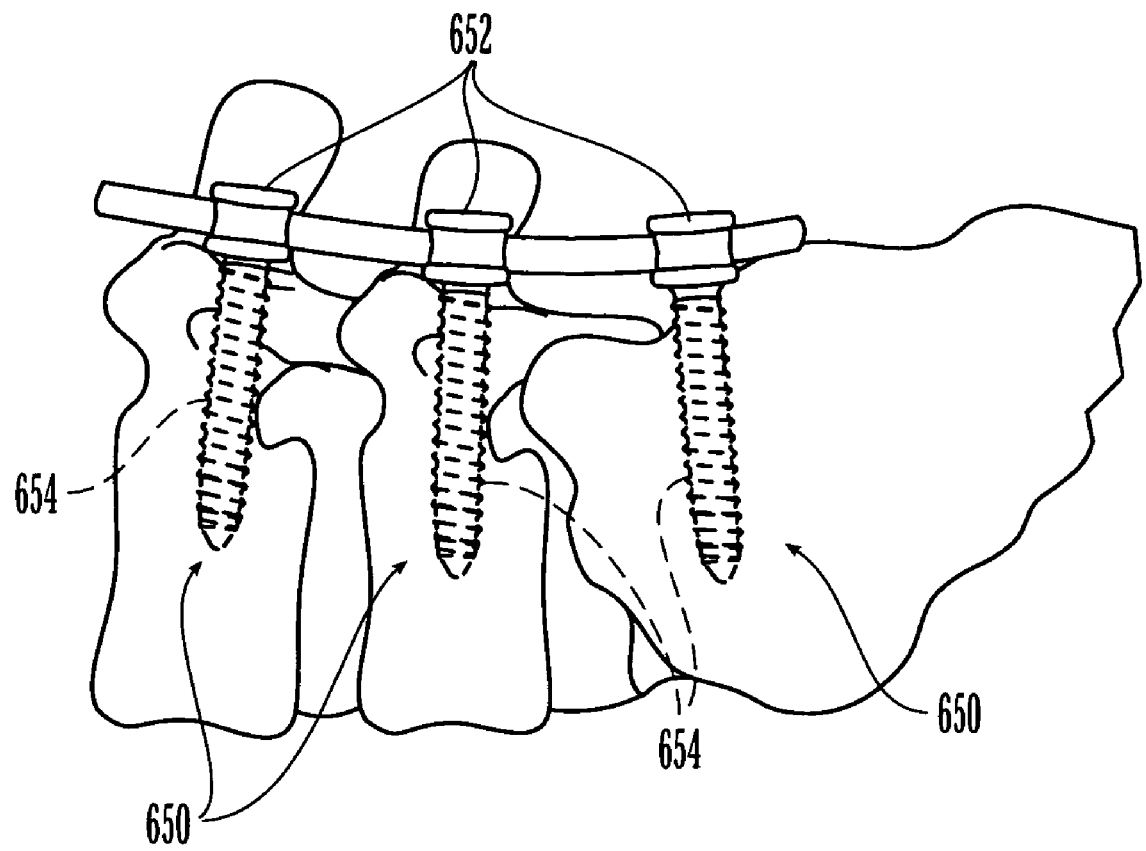
FIG. 22 is a perspective view of an exemplary embodiment of a fixation system attached to the spine.

In order to secure the fixation rod in the channel 666 of bone screw 650, a locking cap 681, such as the one shown in FIG. 6A, may be threaded into the head portion 652. A locking cap screwdriver 2100 (FIG. 21) may be used to move the locking cap 681 down the insertion cannula. The prongs 2102 of the locking cap screwdriver 2100 may engage receiving portions (not shown) on the locking cap 681. The screwdriver 2100 may then be rotated such that the external threaded portion 680 of the locking cap 681 engages the internal threaded portion 672 of the head portion 652. This step may be repeated for each screw 650. It will be appreciated by those skilled in the art that any locking cap (e.g., nut, clip, etc.) may be used so long as it may hold a fixation rod to a screw 650. In some embodiments, for example, where the locking cap may be a nut (not shown) which may be positioned around the head portion 652, the insertion cannulas may be removed from the body prior to engaging the locking cap with the screw 650. Moreover, it will also be appreciated that the locking cap screwdriver may have different orientations to correspond to different shaped locking caps (e.g., the locking cap screwdriver may have a hex portion to engage a corresponding hex recess of a locking cap). In other embodiments, a locking cap screwdriver may be unnecessary (e.g., where the locking cap may be a nut that treads onto the head portion 652). Once all locking caps 681 are positioned in the screws 650, as shown in FIG. 22, the fixation rod may be fixed with respect to the screws 650.

The working cannula 475, retractor 500, and/or insertion cannulas may be disengaged from the screws 650 and removed from the patient. The opening(s) may be closed by methods known by those skilled in the art.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A system for implanting an elongated fixation device into a channel formed in one or more spinal fixation devices through an opening in a patient, the system comprising:

a cannula having a proximal end, a distal end, a passageway from the proximal end to the distal end and at least one slot intersecting the passageway, wherein the at least one slot is sized and configured to receive the elongated fixation device; wherein the cannula includes:

an outer cannulated shaft having a bore therethrough; and an inner cannulated shaft having a bore therethrough, the bore of the inner cannulated shaft defining the passageway, the inner cannulated shaft slidably receivable within the bore of the outer cannulated shaft, the inner cannulated shaft includes diametrically opposed flexible members, each flexible member having a first end portion and a second end portion, the first end portion is operably connected to the inner cannulated shaft and the second end portion is moveable with respect to the inner cannulated shaft, the outer cannulated shaft is slidable on the inner cannulated shaft to and between a first position and a second position, the flexible members positioned in engagement with an outer periphery of the spinal fixation device when the outer cannulated shaft is positioned in the second position, the inner cannulated shaft further includes an arm diametrically opposed to the slot, the arm having a first end portion and a second end portion, the first end portion is operably connected to the inner cannulated shaft and the second end portion is moveable with respect to the inner cannulated shaft such that when the outer cannulated shaft moves from the first position to the second position, the second end portion of the arm moves into the channel formed in thespinal fixation device.

2. The system of claim 1, further comprising a dilation mechanism for increasing the size of an incision to form the opening.

3. The system of claim 2, wherein the dilation mechanism comprises a retractor having at least two blades for being inserted through the incision, wherein the at least two blades are configured to spread apart to form the opening.

4. The system of claim 2, wherein the dilation mechanism comprises at least one dilator having an elongated cylindrical shape with a channel passing therethrough.

5. The system of claim 4, wherein the dilation mechanism further comprises a retractor, the retractor having at least two blades having an opened position and a closed position, wherein the blades are configured to be inserted over the at least one dilator in the closed position and are configured to move to the opened position to create the opening.

6. The system of claim 4, wherein the dilation mechanism further comprises an inserter, the inserter comprising:

an elongated portion, a proximal end and a distal end; and an enlarged portion on the distal end of the elongated portion;

wherein the at least one dilator is configured to receive the inserter therein.

7. The system of claim 6, wherein the dilation mechanism further comprises a working cannula having a proximal end, a distal end, and a channel extending from the proximal end to the distal end, wherein the channel of the working cannula is sized and configured to receive the at least one dilator.

8. The system of claim 2, wherein the dilation mechanism comprises an inserter, the inserter comprising:

an elongated portion, a proximal end and a distal end; and an enlarged portion on the distal end of the elongated portion;

wherein the inserter is sized and configured to be received within the passageway of the cannula.

9. The system of claim 1, wherein the inner cannulated shaft comprises a second slot and the outer cannulated shaft comprises a protrusion engageable with the second slot.

10. The system of claim 9, wherein the second slot has at least one notch, the second slot being sized and configured for positioning the outer cannulated shaft at least one location on the inner cannulated shaft.

11. The system of claim 1, further comprising an implantation mechanism for implanting the spinal fixation device into vertebrae, the implantation mechanism comprising a shaft having a proximal end, a distal end, and an engagement portion on the distal end sized and configured to engage the spinal fixation device, wherein the implantation mechanism is sized and configured to be inserted into the passageway of the cannula.

12. The system of claim 11, wherein the implantation mechanism comprises a protrusion on the engagement portion and the inner cannulated shaft comprises a longitudinal recess, the protrusion being moveable along the recess, and wherein the protrusion and longitudinal recess are configured to align the at least one slot of the cannula relative to the spinal fixation device.

13. The system of claim 1, further comprising an implant positioner sized and configured to be inserted into the passageway of the cannula, the implant positioner having an elongated shaft, a proximal end, a distal end and an engaging portion on the distal end sized and configured to engage the spinal fixation device and manipulate the spinal fixation device relative to the cannula.

14. The system of claim 1, further comprising an implantation mechanism for implanting the spinal fixation device into a vertebrae, the implantation mechanism comprising a shaft having a proximal end, a distal end, and an engagement portion on the distal end sized and configured to engage the spinal fixation device, wherein the implantation mechanism is sized and configured to be inserted into the passageway of the cannula.

15. The system of claim 14, wherein the implantation mechanism further comprises a first sleeve having a proximal end and a distal end, the first sleeve being positionable around the shaft.

16. The system of claim 15, wherein the spinal fixation device comprises a head portion and a shank portion, the head portion including the channel for receiving the elongated fixation device, and wherein the engagement portion of the implantation mechanism comprises a protruding portion and at least one shoulder portion, the protruding portion engages the shank portion of the spinal fixation device and the at least one shoulder portion engages the channel of the head portion of the spinal fixation device.

17. The system of claim 16, wherein the head portion of the spinal fixation device has internal threads and the distal end of the first sleeve has a threaded portion, the threaded portion of the first sleeve being sized and configured to engage the internal threads of the head portion of the spinal fixation device.

18. The system of claim 17, the implantation mechanism further comprising a second sleeve, wherein the first sleeve comprises a recess and the second sleeve comprises a protrusion, the protrusion configured to engage the recess to enable the second sleeve to rotate relative to the first sleeve while preventing the second sleeve from moving axially relative to the first sleeve.

19. The system of claim 18, wherein the implantation mechanism further comprises a connecting portion at the proximal end of the shaft, the connecting portion being attachable to a driving mechanism.

20. The system of claim 1, further comprising a fixation device inserter for inserting the elongated fixation device into the spinal fixation device.

21. The system of claim 20, wherein the fixation device inserter comprises:
an elongated shaft;
a moveable member positioned within the elongated shaft for engaging the elongated fixation rod; and
an actuation mechanism operably associated with the moveable member, the actuation mechanism configured to move the moveable member between a first position and a second position.

22. The system of claim 21, wherein the fixation device inserter further comprises a handle portion.

23. The system of claim 21, wherein the elongated fixation rod comprises an engaging portion configured to be coupled to the moveable member.

24. The system of claim 1, wherein the spinal fixation device comprises a head portion including the channel and a shank portion, and wherein the cannula further comprises a visual indicator designed and configured to enable an operator to align the at least one slot of the cannula with the channel of the head portion of the spinal fixation device.

25. The system of claim 1, wherein the spinal fixation device comprises a head portion including the outer periphery and at least one recess in the outer periphery, the distal end of the cannula being configured to engage the at least one recess of the head portion.

26. The system of claim 1, further comprising a locking cap, wherein the passageway of the cannula is configured to receive the locking cap.

27. The system of claim 26, further comprising a locking cap screwdriver having an elongated shaft, a proximal end, a distal end and a engaging portion at the distal end, the locking cap screwdriver configured to be positioned within the passageway of the cannula, wherein the engaging portion of the locking cap engages the locking screw.

28. A system for implanting an elongated fixation device into a channel formed in one or more spinal fixation devices through an opening in a patient, the system comprising:
a cannula having a proximal end, a distal end and at least one sidewall, the at least one sidewall defining a passageway from the proximal end to the distal end, the cannula having at least one slot in the at least one sidewall communicating with the passageway, and a pair of diametrically opposed flexible members for engaging the spinal fixation device, each of the flexible members comprising a first end portion and a second end portion, the first end portion operably connected to the at least one sidewall of the cannula and the second end portion freely moveable into and out of the passageway of the cannula, the second end portion engageable with the spinal fixation device; and
an arm diametrically opposed from the at least one slot, the arm having a first end portion and a second end portion, the first end portion being operably connected to the at least one sidewall of the cannula and the second end portion being freely moveable into and out of the channel formed in the spinal fixation device.

29. The system of claim 28, further comprising an implantation mechanism for implanting the spinal fixation device into a vertebrae, the implantation mechanism comprising a shaft having a proximal end, a distal end, and an engagement portion on the distal end sized and configured to engage the spinal fixation device, wherein the implantation mechanism is sized and configured to be inserted into the passageway of the cannula.

30. The system of claim 29, wherein the implantation mechanism further comprises a first sleeve having a proximal end and a distal end, the first sleeve being positionable around the shaft.

31. The system of claim 30, wherein the spinal fixation device comprises a head portion and a shank portion, the head portion including the channel for receiving the elongated fixation device, and wherein the engagement portion of the implantation mechanism comprises a protruding portion and at least one shoulder portion, the protruding portion engages the shank portion of the spinal fixation device and the at least one shoulder portion engages the channel of the head portion of the spinal fixation device.

32. The system of claim 31, wherein the head portion of the spinal fixation device has internal threads and the distal end of the first sleeve has a threaded portion, the threaded portion of the first sleeve being sized and configured to engage the internal threads of the head portion of the spinal fixation device.

33. The system of claim 28, wherein the cannula has an inner diameter between about 3 mm and about 20 mm.

34. The system of claim 33, wherein the cannula has an inner diameter between about 12 mm and about 16 mm.

35. The system of claim 33, wherein the cannula has an outer diameter between about 3 mm and about 20 mm.

36. The system of claim 35, wherein the cannula has an outer diameter between about 14 mm and about 17 mm.

37. The system of claim 35, wherein the cannula has a length between about 40 mm and about 200 mm.

38. The system of claim 37, wherein the cannula has a length between about 140 mm and about 160 mm.

39. The system of claim 37, wherein the at least one slot has a width between about 3 mm and about 10 mm, and wherein the at least one slot has a height between about 30 mm and about 160 mm.

40. The system of claim 39, wherein the at least one slot has a width between about 5 mm and about 8 mm, and wherein the at least one slot has a height between about 110 mm and about 130 mm.

* * * * *